US011191823B2

(12) United States Patent
Abraham et al.

(10) Patent No.: US 11,191,823 B2
(45) Date of Patent: Dec. 7, 2021

(54) COMPOSITIONS AND METHODS FOR TREATING ARENAVIRUS INFECTION

(71) Applicants: CHILDREN'S MEDICAL CENTER CORPORATION, Boston, MA (US); DANA-FARBER CANCER INSTITUTE, INC., Boston, MA (US)

(72) Inventors: Jonathan Abraham, Boston, MA (US); Stephen Harrison, Boston, MA (US); Kai Wucherpfennig, Boston, MA (US)

(73) Assignees: CHILDREN'S MEDICAL CENTER CORPORATION, Boston, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/308,318

(22) PCT Filed: Jun. 7, 2017

(86) PCT No.: PCT/US2017/036395
§ 371 (c)(1),
(2) Date: Dec. 7, 2018

(87) PCT Pub. No.: WO2017/214298
PCT Pub. Date: Dec. 14, 2017

(65) Prior Publication Data
US 2019/0255169 A1    Aug. 22, 2019

Related U.S. Application Data

(60) Provisional application No. 62/392,729, filed on Jun. 8, 2016.

(51) Int. Cl.
*A61K 39/12* (2006.01)
*C12N 15/86* (2006.01)
(Continued)

(52) U.S. Cl.
CPC ........ *A61K 39/12* (2013.01); *A61K 39/39516* (2013.01); *A61P 31/14* (2018.01);
(Continued)

(58) Field of Classification Search
None
See application file for complete search history.

(56) References Cited

U.S. PATENT DOCUMENTS

| 2010/0316563 A1 | 12/2010 | Clementi et al. |
| 2014/0249467 A1 | 9/2014 | Broderick et al. |
| 2014/0377740 A1* | 12/2014 | Branco ................ C07K 14/005 435/5 |

FOREIGN PATENT DOCUMENTS

WO    2018204080 A1    11/2018

OTHER PUBLICATIONS

Abraham, J. et al., "Structural basis for receptor recognition by New World Hemorrhagic Fever Arenaviruses," Nature Structural & Molecular Biology, vol. 17, No. 4, pp. 438-444 (2010).
(Continued)

*Primary Examiner* — Agnieszka Boesen
(74) *Attorney, Agent, or Firm* — Melissa Hunter-Ensor; Greenberg Traurig, LLP

(57) ABSTRACT

The invention generally provides compositions and methods of treating or preventing an arenavirus infection, using an agent that inhibits binding of an arenavirus glycoprotein 1 (GP1) polypeptide to transferrin receptor 1 (TfR1). The invention also provides methods of designing or identifying therapeutic agents that bind to or target a GP1 receptor-binding site (RBS) to inhibit arenavirus attachment to a cell, and therapeutic agents identified using the methods.

19 Claims, 21 Drawing Sheets

Figure 1:
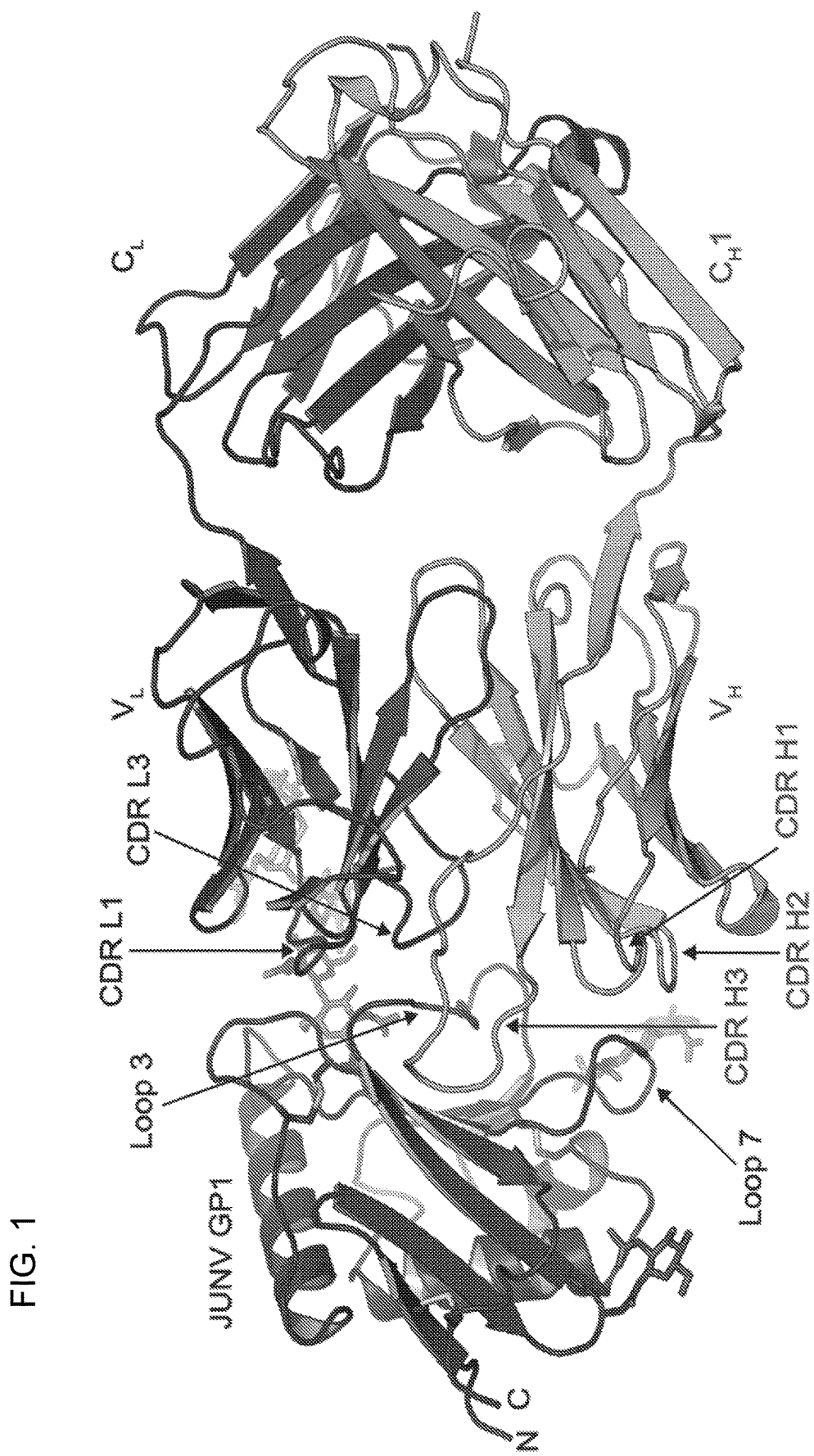

Specification includes a Sequence Listing.

(51) Int. Cl.
| | |
|---|---|
| C07K 16/10 | (2006.01) |
| A61P 31/14 | (2006.01) |
| G16B 15/00 | (2019.01) |
| A61K 39/395 | (2006.01) |
| C07K 14/08 | (2006.01) |
| G01N 33/53 | (2006.01) |
| G01N 33/569 | (2006.01) |

(52) U.S. Cl.
CPC .............. *C07K 14/08* (2013.01); *C07K 16/10* (2013.01); *C12N 15/86* (2013.01); *G01N 33/53* (2013.01); *G01N 33/56983* (2013.01); *G16B 15/00* (2019.02); *C07K 2317/21* (2013.01); *C07K 2317/33* (2013.01); *C07K 2317/55* (2013.01); *C07K 2317/76* (2013.01); *C12N 2760/10022* (2013.01); *C12N 2760/10031* (2013.01); *C12N 2760/10043* (2013.01); *C12N 2760/16134* (2013.01); *G01N 2333/08* (2013.01)

(56) References Cited

OTHER PUBLICATIONS

Hypothetical Protein [*Rhizobium giardinii*], Accession No. WP_018327311, Publication online Jun. 28, 2013.
Sanchez, A. et al., "Junin Virus Monoclonal Antibodies: Characterization and Cross-reactivity with Other Arenaviruses," Journal of General Virology, vol. 70, No. 5, pp. 1125-1132 (1989).
International Search Report and Written Opinion for corresponding PCT Patent Application No. PCT/US17/36395, dated Oct. 27, 2017 (14 pages).
Choe et al., "Transferrin receptor 1 in the zoonosis and pathogenesis of New World hemorrhagic fever arenaviruses," Current Opinion in Microbiology, Jul. 30, 2011; vol. 14, No. 4, pp. 476-482.
Helguera et al., "An Antibody Recognizing the Apical Domain of Human Transferrin Receptor 1 Efficiently Inhibits the Entry of All New World Hemorrhagic Fever Arenaviruses," Journal of Virology, Apr. 1, 2012; vol. 86, No. 7, pp. 4024-4028.
Robinson et al., "Most neutralizing human monoclonal antibodies target novel epitomes requiring both Lassa virus glycoprotein subunits," Nature Communications, May 10, 2016; vol. 7, pp. 1-14.
Extended European Search Report in corresponding European Patent Application No. 17810953.4, dated Dec. 10, 2019 (10 pages).
Abraham et al., "Host-Species Transferrin Receptor 1 Orthologs Are Cellular Receptors for Nonpathogenic New World Clade B Arenaviruses," PLoS Pathogens, Apr. 2009, vol. 5, Iss. 4, e1000358 (10 pages).
Aoki et al., "Structure of rotavirus outer-layer protein VP7 bound with a neutralizing Fab," Science, Jun. 12, 2009, vol. 324, No. 5933, pp. 1444-1447 (9 pages).
Branco et al., "Shedding of soluble glycoprotein 1 detected during acute Lassa virus infection in human subjects," Virology Journal, Nov. 9, 2010, vol. 7, Article No. 306 (11 pages).
Briese et al., "Genetic Detection and Characterization of Lujo Virus, a New Hemorrhagic Fever-Associated Arenavirus from Southern Africa," PLoS Pathogens, May 2009, vol. 5, Iss 5, e1000455 (8 pages).
Burri et al., "Envelope Glycoprotein of Arenaviruses," Viruses, 2012, vol. 4, pp. 2162-2181 (20 pages).
Chandran et al., "Endosomal Proteolysis of the Ebola Virus Glycoprotein is Necessary for Infection," Science, Jun. 10, 2005, vol. 308, pp. 1643-1645 (4 pages).
Demogines et al., "Dual Host-Virus Arms Races Shape an Essential Housekeeping Protein," PLoS Biology, May 2013, vol. 11, Iss. 5, e1001571 (13 pages).
Dias et al., "A Shared Structural Solution for Neutralizing Ebolaviruses," Nature Structural & Molecular Biology, 2011, vol. 18, No. 12, pp. 1424-1427 (9 pages).
Enria et al., "Importance of Dose of Neutralising Antibodies in Treatment of Argentine Haemorrhagic Fever with Immune Plasma," The Lancet, Aug. 4, 1984, vol. 2, pp. 255-256 (2 pages).
Flyak et al., "Mechanism of Human Antibody-Mediated Neutralization of Marburg Virus," Cell, Feb. 26, 2015, vol. 160, pp. 893-903 (12 pages).
Hashiguchi et al., "Structural Basis for Marburg Virus Neutralization by a Cross-Reactive Human Antibody," Cell, Feb. 26, 2015, vol. 160, pp. 904-912 (10 pages).
Lee et al., "Structure of the Ebola virus glycoprotein bound to an antibody from a human survivor," Nature, Jul. 10, 2008, vol. 454, No. 7201, pp. 177-182 (17 pages).
Maiztegui et al., "Efficacy of Immune Plasma in Treatment of Argentine Haemorrhagic Fever and Association Between Treatment and a Late Neurological Syndrome," The Lancet, Dec. 8, 1979, vol. 2, pp. 1216-1217 (2 pages).
Murin et al., "Structures of protective antibodies reveal sites of vulnerability on Ebola virus," Proceedings of the National Academy of Sciences of the United States of America, Dec. 2, 2014, vol. 111, No. 48, p. 17182-17187 (6 pages).
Radoshitzky et al., "Receptor determinants of zoonotic transmission of New World hemorrhagic fever arenaviruses," Proceedings of the National Academy of Sciences of the United States of America, Feb. 19, 2008, vol. 105, No. 7, pp. 2664-2669 (6 pages).
Radoshitzky et al., "Transferrin receptor 1 is a cellular receptor for New World haemorrhagic fever arenaviruses," Nature, Mar. 1, 2007, vol. 446, pp. 92-96 (6 pages).
Schmidt et al., "Viral Receptor-Binding Site Antibodies with Diverse Germline Origins," Cell, May 21, 2015, vol. 161, pp. 1026-1034 (10 pages).
Xu et al., "A recurring motif for antibody recognition of the receptor-binding site of influenza hemagglutinin," Nature Structural & Molecular Biology, Mar. 2013, vol. 20, No. 3, pp. 363-370 (20 pages).
Zhou et al., "Structural Basis for Broad and Potent Neutralization of HIV-1 by antibody VRC01," Science, Aug. 13, 2010, vol. 329, No. 5993, pp. 811-817 (19 pages).

\* cited by examiner

MACV GP1 / TfR1

JUNV GP1 / GD01

```
                β1                       β2              β3
JUNV   PHDLPLICTLNKSHLYIKGGNAS----FKISFDDIAVLLPEYDVIIQHPADMSWQSK------SDDQIWLSQWFMNAVGHDWYLDPPFLCRN
MACV   SNELPSLCMLNSFYYMRGGVNT----FLIEVSDISVLMKEYDVSIYEPEDLGMCLN------KSDSSWAIHWFSNALGHDWLMDPPMLCRN
TCRV   SHELPMICLAKTHLYLKSGRSS----FKINIDSVTVITRSADVFVHSP-KIGSCFE------SDEE-WVAWWIEAIGHRWDQDPGLLCRN
GTOV   FHELPISLCRVNSYSLIRLSHMSNQALSVEYVDVHPVLCSSSPTTLDN--YTQCIK------GSPEFDWILGWTIKGLGHDFLRADPRICCEP
SABV   FEDHPTSCMVHSTYYVHEKNATWCLEVSVTDVTLLMAEHDRQVLNN---LSNCVHPAVEHRSRMVGLLEWIFRALKYDFMHDPTPLCQK
CHAPV  FEDHPISCTVKTLYYTRESENATWCVEIAALDMSVLLSPHDPRVMGN---LSMCVHPDIKHRSELLGLLEWILRALKYDFLNYPPLLCEK
                                                                        *                *

Loop 7        α⁰            β6
JUNV   RTKTEGFI-FQVITSKTGINENYAKKFRTGMHHLYRG----YPDSCLDGK CLMKAQP-------LQCPLDHVNTLH
MACV   KTKKEGSN-IQFHISRADDARVYGKIIRNGMRHLFRG----FHDPCEEGKVCYLTIMQCGDPSSFDYCGVNHLSKCQFDHVNTLH
TCRV   KTKEGKL-IQIHISRADGNVHYGWRLKWGLDHIYRG-----REEPCFEGEQCLLIKIQP-------TDCKADHTNTFR
GTOV   KKTTNAEFTPQLLTDSPETHHYRSKIEVGIRHLFGN-----YITNDSYSKMSVVMRMT-------TWEG-------QCSNSHVNTLR
SABV   QTSTVNETRVQIHITEGFGSHGFEDTILQRLGVLFGSRIAFSNIQDLGKKRFLLIRN------STWKN-------QCEMHVNSMH
CHAPV  VTSSVNETRIQIVSDSAGSHDFKETMLQRLAILFGTKLMPDKTP-------KQFIVIRN------QTWVN-------QCKSNHVNTLH
                                                 *
```

| Survivor | PRNT₈₀ |
|---|---|
| AHF1 | 1:10,240 |
| AHF2 | 1:5,120 |
| AHF3 | 1:2,560 |
| AHF4 | 1:1,280 |
| AHF5 | 1:1,280 |
| AHF6 | 1:640 |
| AHF7 | 1:640 |
| AHF8 | 1:320 |
| AHF9 | 1:40 |
| AHF10 | N.T. |

SEQUENCE LISTING

<160> NUMBER OF SEQ ID NOS: 38

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Gly Phe Thr Phe Gly Thr Ser Ile
1               5

<210> SEQ ID NO 2
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 2

Ile Ser His Asp Glu Ser Arg Lys
1               5

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Lys Asp Leu Ser Pro Pro Tyr Ser Tyr Ala Trp Asp Ile Phe Gln
1               5                   10                  15

Tyr Trp

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Val Leu Tyr Ser Ser Arg Ser Asp Asn Lys Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln Tyr Tyr Ser Ser Pro Pro Thr Phe
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Thr Phe Ser Ser Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Trp Ser Asp Gly Ser Asn Glu
1               5
```

```
<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Thr Asp Lys Thr Tyr Val Ser Gly Tyr Thr Ser Thr Trp Tyr Tyr
1               5                   10                  15

Phe Asn Tyr

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ile Asp Asn Trp
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln His Arg Thr
1

<210> SEQ ID NO 11
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Ser
                20                  25                  30

Ala Met His Trp Val Arg Gln Ala Pro Gly Lys Gly Leu Glu Trp Val
            35                  40                  45

Ala Val Ile Trp Ser Asp Gly Ser Asn Glu Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Thr Asp Lys Thr Tyr Val Ser Gly Tyr Thr Ser Thr Trp Tyr Tyr
                100                 105                 110

Phe Asn Tyr Trp Gly Gln Gly Thr Leu Val Thr Val Ser
            115                 120                 125
```

-continued

<210> SEQ ID NO 12
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asp Asn Trp
            20                  25                  30

Leu Ala Trp Tyr Gln Gln Lys Pro Gly Lys Ala Pro Lys Leu Leu Ile
        35                  40                  45

Tyr Thr Ala Ser Arg Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Arg Thr Phe Gly Gln Gly
                85                  90                  95

Thr Lys Val Glu Ile Lys
            100

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Val Val His Pro Gly Arg
1               5                   10                  15

Ser Leu Arg Leu Ser Cys Ala Ala Ser Gly Phe Thr Phe Gly Thr Ser
            20                  25                  30

Ile Met His Trp Val Arg Gln Ala Pro Gly Lys Gly Met Gln Trp Val
        35                  40                  45

Ala Gln Ile Ser His Asp Glu Ser Arg Lys Phe Tyr Ser Asp Ser Val
    50                  55                  60

Lys Gly Arg Phe Thr Val Ser Arg Asp Asn Ser Lys Asn Thr Leu Phe
65                  70                  75                  80

Leu Glu Met Ser Ser Leu Arg Ile Glu Asp Thr Ala Val Tyr Tyr Cys
                85                  90                  95

Ala Lys Asp Leu Ser Pro Pro Tyr Ser Tyr Ala Trp Asp Ile Phe Gln
            100                 105                 110

Tyr Trp Gly Gln Gly Ser Leu Val Thr Val Ser
        115                 120

<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Ile Val Met Thr Gln Ser Pro Glu Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Arg Ser Asp Asn Lys Asp Tyr Leu Ala Trp Tyr Gln Gln Lys Pro
        35                  40                  45

Gly Gln Ser Pro Lys Leu Leu Ile Tyr Trp Ala Ser Thr Arg Glu Ser
50                  55                  60

Gly Val Pro Glu Arg Phe Thr Gly Ser Gly Ser Gly Thr Asp Phe Thr
65                  70                  75                  80

Leu Ser Ile Ser Ser Leu Gln Ala Glu Asp Val Ala Val Tyr Tyr Cys
                85                  90                  95

Gln Gln Tyr Tyr Ser Ser Pro Pro Thr Phe Gly Gly Gly Thr Lys Val
            100                 105                 110

Glu Leu Lys
        115

<210> SEQ ID NO 15
<211> LENGTH: 141
<212> TYPE: PRT
<213> ORGANISM: Junin mammarenavirus

<400> SEQUENCE: 15

Asp Leu Pro Leu Leu Cys Thr Leu Asn Lys Ser His Leu Tyr Ile Lys
1               5                   10                  15

Gly Gly Asn Ala Ser Phe Lys Ile Ser Phe Asp Asp Ile Ala Val Leu
            20                  25                  30

Leu Pro Glu Tyr Asp Val Ile Ile Gln His Pro Ala Asp Met Ser Trp
        35                  40                  45

Cys Ser Lys Ser Asp Asp Gln Ile Trp Leu Ser Gln Trp Phe Met Asn
50                  55                  60

Ala Val Gly His Asp Trp Tyr Leu Asp Pro Pro Phe Leu Cys Arg Asn
65                  70                  75                  80

Arg Thr Lys Thr Glu Gly Phe Ile Phe Gln Val Asn Thr Ser Lys Thr
                85                  90                  95

Gly Ile Asn Glu Asn Tyr Ala Lys Lys Phe Lys Thr Gly Met His His
            100                 105                 110

Leu Tyr Arg Glu Tyr Pro Asp Ser Cys Leu Asp Gly Lys Leu Cys Leu
        115                 120                 125

Met Lys Ala Gln Pro Thr Ser Trp Pro Leu Gln Cys Pro
130                 135                 140

<210> SEQ ID NO 16
<211> LENGTH: 3412
<212> TYPE: DNA
<213> ORGANISM: Junin mammarenavirus

<400> SEQUENCE: 16
tgcagtaagg ggatcctagg cgattttggt aacgctataa gttgttactg ctttctattt      60
ggacaacatc aaaccatcta ttgtacaatg gggcaattca tcagcttcat gcaagaaata     120
cctacctttt tgcaggaagc tctgaatatt gctcttgttg cagtcagtct cattgccatc     180
attaagggtg tagtaaacct gtacaaaagt ggtttgttcc aattctttgt attcctagca     240
ctcgcaggaa gatcctgcac agaagaagct tttaaaatcg gactgcacac agagttccag     300
actgtgtcct tctcaatggt gggtctcttt tccaacaatc acatgacct gcctctgttg     360
```

-continued

```
tgtaccttaa acaagagcca tctttacatt aagggggggca atgcttcatt caagatcagc    420
tttgatgaca tcgcagtgtt gttaccagaa tatgacgtta taattcagca tccggcagat    480
atgagctggt gttctaaaag tgatgatcaa atttggctgt ctcagtggtt catgaatgct    540
gtggggcatg attggtatct agacccacca tttctgtgta ggaaccgtac aaagacagaa    600
ggcttcatct ttcaagtcaa tacctccaag actggtatca atgaaaacta tgccaagaag    660
tttaagactg gtatgcacca tttatataga gaatacccccg actcttgctt ggatggcaaa    720
ctgtgtttga tgaaggcaca acccaccagt tggcctctcc aatgtccact tgaccatgtc    780
aacacattac atttcctcac aagaggcaag aacattcagc ttccaaggag gtctttaaaa    840
gcattctttt cctggtctct gacagactca tccggcaagg acacccctgg aggctattgt    900
ctagaagagt ggatgctcgt tgcagccaaa atgaagtgtt ttggcaatac tgctgtagca    960
aaatgcaatc tgaatcatga ctctgaattc tgtgacatgc tgaggctttt tgattacaac   1020
aaaaatgcta tcaaaacctt aaatgatgaa actaagaaac aagtaaatct gatgggacag   1080
acaatcaatg cgctgatatc tgacaattta ttgatgaaaa acaaaattag ggaattgatg   1140 agtgtcccctt actgcaatta cacaaaattt tggtatgtca accacacact ttcaggacaa   1200
cactcattac caaggtgctg gttaataaaa acaacagct atttgaacat ttctgacttc   1260
cgtaatgact ggatactaga aagtgacttc ttaatttctg aaatgctaag caaagagtat   1320
tcggacaggc agggcaaaac tcccttgact ttagttgaca tctgtttttg gagcacagta   1380
ttcttcacag cgtccctctt ccttcacttg gtgggcatac ccacccatag gcacatcaga   1440
ggcgaggcat gccctctgcc ccacaggcta aatagcttgg gtggttgcag atgtggtaag   1500
taccccaatc taaagaaacc aacagtttgg cgcagaggac actaagacct cccgaaggtc   1560
cccaccagcc cggcattgc ccgggctggt gtggcccccc agtccgcggc ctggccgcgg   1620
actggggagg cactgcttac agtgcatagg ctgccttcgg gaggaacagc aagctcggtg   1680
gtaatagagg tgtaagttct tcttcataga gcttcccatc caacactgac tgaaacatta   1740
tgcagtctag cagagcacag tgtggctcac tggaggccaa cttaaaggga gcatccttat   1800 ctctctttttt cttgctgaca accactccat tgtgatgttt gcataggtgg ccaaatttct   1860
cccagacctg ttggtcgaac tgcctggctt gttctgatgt aagcctaaca tcaaccagct   1920
taagatctct tcttccatgg aggtcaaaca acttcctgat gtcatcggac ccttgagtgg   1980
tcacaaccat gtccggaggc agcaagccaa tcacgtaact aagaactcct ggcattgcat   2040
cttctatgtc tttcattaag atgccgtgag agtgtctgct accatttta aacccttctt   2100 catcatgtgg ttttctgaag cagtgaatat acttgctacc tgcaggctgg aacaacgcca   2160
tctcaacagg gtcagtagct ggtccttcaa tgtcgagcca aagggtattg gtggggtcga   2220
gtttccccac tgcctctctg atgacagctt cttgtatctc tgtcaagtta gccaatctca   2280
aattctgacc gttcttttcc ggttgtctag gtccagcaac tggtttcctt gtcagatcaa   2340
tacttgtgtt gtcccatgac ctgcctatga tttgtgatct ggaaccaata taaggccaac   2400
catcgccaga aaggcaaagt ttgtacagaa ggttttcata agggtttcta ttgcctggtt   2460
tctcatcaat aaacatgcct tctcttcgtt taacctgaat ggttgatttt atgagggaag   2520
aaaagttatc tggggtgact ctgattgtct ccaacatatt tccatcatca agaatggatg   2580
caccagcctt tactgcagct gaaagactaa agttgtagcc agaaatgttg atggagcttt   2640
catccttagt cacaatctgg aggcagtcat gttcctgagt caatctgtca aggtcactca   2700
agtttggata cttcacagtg tatagaagcc caagagaggt taaagcctgt atgacactgt   2760
```

```
tcattgtctc acctccttga acagtcatgc atgcaattgt caatgcagga acagaaccaa    2820
actgattgtt aagttttgaa ggatctttaa catcccatac cctcaccaca ccatttcccc    2880
cagttccttg ctgttgaaat cccagtgttc tcaatatctc tgatctcttg gccagttgtg    2940
actgagacaa gttacccatg taaacccctt gagagcctgt ctctgctctt ctaaacttgg    3000
tttttaaatt cccaaggcca gacgccaact ccatccgctc aaccctcccc agatctcccg    3060
ccttgaaaac cgtgtttcgt tgaacactcc tcatggacat gagtctgtca acctctttat    3120
tcaggtccct caacttattg aggtcttctt ccccccttt agtctttctg agtgcccgct    3180
gcacctgtgc cacttggttg aagtcaatgc tgtcagcaat tagcttggca tccttcagaa    3240
catccgactt gacagtctga gtaaattgac tcaaacctct ccttaaggac tgagtccatc    3300
taaagcttgg aacctctttg gagtgtgcca tgccagaaga tctggtggtt ttgatctgag    3360
aaaaaattgc tcagtgaaag tgttagacac tatgcctagg atccactgtg cg            3412
```

<210> SEQ ID NO 17
<211> LENGTH: 760
<212> TYPE: PRT
<213> ORGANISM: Homo sapiens

<400> SEQUENCE: 17

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255
```

-continued

Val Arg Ala Gly Lys Ile Thr Phe Ala Glu Lys Val Ala Asn Ala Glu
        260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
        290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
        370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
        450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
        610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro

```
                675                 680                 685
Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 18
<211> LENGTH: 32829
<212> TYPE: DNA
<213> ORGANISM: Homo sapiens

<400> SEQUENCE: 18
ccggttaggg gccgccatcc cctcagagcg tcgggatatc gggtggcggc tcgggacgga       60
ggacgcgcta gtgtgagtgc gggcttctag aactacaccg accctcgtgt cctcccttca      120
tcctgcgggg ctggctggag cggccgctcc ggtgctgtcc agcagccata gggagccgca      180
cggggagcgg gaaagcggtc gcggcccag gcggggcggc cgggatggag cggggccgcg       240
agcctgtggg gaaggggctg tggcggcgcc tcgagcggct gcaggtacac ggggtcggcg      300
gctgtgcgca gaggcgtccc tgcgcctctc gtcccttcgc ctctcgtccc ttcccttctc      360
tctgccttct tgcccgcctc ctcggtcaca gagcgacgaa tgacgagacc aggtgtaccc      420
cactgtcgct ctcagccccg ggacttcggg gtcctcgccc ttgaaggccg caggccctag      480
tgcgccggct ccgggctgcg gtccgggag cgcgggcgca ccaaggtgc agctgcgcgg        540 cgtgcggcgc cggggaaca cgtggctgct ccaggaagtc gccccaggga acggctggga       600
ttcgtgggtg accttgggct cctaaacctt cggttccccg ggctccgggc gggccccgtt      660
ctcactgcgg aaagggacaa agctgtcccc gattcggtta ctagcgtgtt acaggcatta      720
attagatacg ggtttctgta aacttaccct tcggctctgg tacaacctga tcttgccatg      780
ctctgcctgt tcgccttgtg tatggattct gttttctcaa ggcagaatcc gactgaacgc      840
cgcaggtgtt cacattaaga atattgctag cagttctcac tacaagacgg gagccatagg      900
agtgacttat ttgtgaaaga tacttggaga ttagcggtgt ggtcagaggg ctgtgctgga      960
ttgatgggcg ccggagaggc cgattgtgtc acattctgct ggacagttct tttaaggttg     1020
ggagggtggg taagaaaata cattctgatt cggctctttt cggataacgc tttccctctg     1080
cttactgctt gtaagacctc acttacccgg gggactggat tctgcagctt tttccatttt     1140
cttccccgtt gataagagga ttaaagttag gaaattgtat ttggctaccc catgcttata     1200
tgctaagctt actgtgaaaa ttaaggttag gctgtctaga gtacttgtgg accctgctgg     1260 ttcccccgc cccccggccc tgaattttgg gttacaatat gcttctcaag aaaactcaga      1320
gttaagataa tttttgtcat cgattttgca aggttatata tagcatagca tccttcaatt     1380
tcctttggat gttcttatca agtaatggtg gctgtaaacc tagcctgtgt tgaagattgt     1440
tagatagaca gcagtttggc taactccgcc ctaaggcgag gcagttactt gcctctgata     1500
atgtatttaa atgtcatgga gcaagattcc cagctaaacc tgaatcgatc acaatgctag     1560
ttaaaaatga ccctcggctg ggcgcattgg ctcccgcctg taatcccagc actttgggag     1620
```

```
gccaaggcag gcggatcacc taaggtcagg agttcgagtc cagtctgact aacatggtga    1680
aatcctgtct ctactaaaaa cacaaaaatt agccgggcat ggtggctcac gtctgtaatt    1740
ccagcacttt gggaggccga ggcaggtgga tcacttgtgg tgaggagttc gagactagcc    1800
tggccaacat ggtgaaaccc cgtctctacg aaaaatacaa aaattagctg ggcatggtgg    1860
tgcacacctg taatcccagc cactcaggag gctgaggctc gaaagtcgct ttaacctggg    1920
aggcagaggt tgtagtgagc tgagatcgtg ctactgcact ccagcctgcg cgacagcgag    1980
atgccatctc aaaacaaca acaaaaaaac tccctactaa accagaagat gatgggacg     2040 ggaaaagatc ctggtccaat gttttcatta tatttttcat atcatttgga atctcatgca    2100
tcaggcatgc cccagtactg ttaaagacaa tattttact cattatcagg tagttcaata    2160
ccagttatta caggataggg aagtcagtca gagaaggctt catagagatg aagccttgag    2220
ctgagcctgg aagaaatgag gaggacctca aggaacagag aagaatgttg gtgggtaaaa    2280
acaggggctg gattctgtct gattttggag aaaatagagg gtagtgaagt tgttaggcag    2340
tgaatgtgtt ccatttcatg gttcaaaacg tggggctacg ttttgcctac ctgagcttca    2400
ttattaatgt gagaaattga attgttgttt tcagtcacca ttgagaacac caaagataac    2460
acaagtagct tagattatta tttatttatt tattttgac agatttcaca cttgttgccc    2520
aggctgtagt gcaatggtgt gatctcggct ccctgcaacc tccacctccc ccaggttcaa    2580
gtgattctcc tgcctcagcc tcccagtag ctgggattac aggcatgcgc caccatgccc     2640
ggctaatttt gtatttttt ggtagagatg ggatttctcc atgtttggtc aggctagtct     2700
caaactctca acctcaggtg atctgctcgc ctcggcctcc caaagtgttg ctgggattac    2760
aggcgtgagc caccatgccc ggccatcgct ttgtgttctt aaaattaatt taaaacaaga    2820
aaacttgagg aatgatggtt cagatgagtg ttaaaacttg caagatgttt tttcctagaa    2880
aaggatgatt aaaattggtt cagggtgggg ccttccagtt ctggctctaa tgattgggtc    2940
cttactgttc tggtggagtg gtagtgataa gcttttttgta acagaagggg caaaagattg    3000
tgcttctggc tgggcgcagt ggctcacgcc ttcgatttcc ttgggatgtt cttatcaagt    3060
aactaatctt agcactttgg gaggccaggt gggtggatca ccctaggtca gaagttccag    3120
accagcctgg ccaacgtggt aaaatcccgt ctctactaaa aatacaaaaa ttagctgggc    3180
atggtggtgg gcacctgtaa tcccagctac tcggagtctg aggtgggaaa atggcttgaa    3240
cccgggaggg ggaggttgca gtgagccgag atcctgccat tgcactccag cctaggcaac    3300
aagaccgaaa ctctgtctca agaaaaaaaa aaagattatg cttctaagaa tatggtctat    3360
tgcatatgga cactggtttt taaagcttga atttaaaaag aattttttgt aataggtttt    3420
agagcttttt cttttctttt tttattattt ttttgagatg gagtctcact ctgtcaccca    3480
ggctggagtg cagtggtgcc atctcggctc actgcaacct ccacctcccg ggttcaagcg    3540
attctcctgc ctcagcctcc ccagtagctg ggattacagg tgcccaccac cacgcccatc    3600 taattttttgt atttttagta gagatggggt ttcaccacct tggccaggct ggtctcaaac    3660
tcctgacctc gtgatccacc tgcctcggct cccaaagtca gtgttgggat tacaggcatg    3720
agccaccgtg cctggccaga aagcttttc ttaatgccag ttataatacc ctttgcttta    3780
caatttgcgt atacctcaca gcttgctttg tgccgtgtgt gtttaatatg ccctaagtgt    3840
actcgtatat aggaaaagct ttaaaatggt atccaataaa tgtccatttt gcaaatctca    3900
ggataatgtc attttcaagt atctagatgc cctcaaacca aattaactgg aaaattcaga    3960
tttcagttaa ggcctttaac ttaacttagg actttgatta cagagatgta ttttgctttg    4020
```

```
acaaaagtta aggttaatgt cttaaatttc cagagatgat aacacagttt ctataaccca    4080
gtaacccatt taacttcgct tagattatca attttcagcc ttgaacaggc cacttagttt    4140
ctctaataac tggcctcttc atctgtaaaa cagcgtaatc tgtgtttcat gtttcttctt    4200
gtgtcaaaga tcgaatcact tgtaggaact attcattcag tcaggatcag tatttcttcc    4260
ccttcccatt ggagatggtt tgtggtattt gtagcataac tggtcttgtc tgccttagtc    4320
ttaattttgt cttttttgtat gtgtcactttt ctttttttt tgagacagag ttttgctctt    4380
gttttccagg ctggagtgca gtggcgcgat cttggctcac tgcaagctcc acctcctggg    4440
ttcacgccat tctcctgcct caggctcccg agtggctggg attacaggcg cccaccacca    4500
cgtccggcta attttgtat ttttagtaga cagggttt ctccatgttg ccaggctgg      4560 tcttgaactc ctgacctcag gtgatccacc catctcagcc tcccaaagtg ctaggattac    4620
aggtgtgagc cacccgccc agcagtatgt gtcattttgt ctactcagaa catagtggtt    4680
cgtacttata attgcagcac tttgggaggc caaggtggga ggattgtttg aggccaggag    4740
ttcaagacca gcctgggcaa catagggtga ccttgtctct acaaaaagaa aaaaaagaa    4800 ttatgtatat aacaaacttt aaaaaggatc ccacttaatt tagttgtcat gtaaactatg    4860
gttaaatacc ttttctagaa aagtgataat gtattttaaa aatttaatgt atcatttagc    4920
ctggtaatag aaagctcact aatctgatac agtagtatct ttttcaataa ttctctattc    4980
tgatacctga ggttcttctg tgtggcagtt cagaatgatg gatcaagcta gatcagcatt    5040
ctctaacttg gtaagatatt tcagttgtat ttctgtgtct gcaagaatgt gaaatataca    5100
agcatgactt taactgagta agcatgaaat aataacccca atctattatc aggtattcat    5160
ttacatttga ttggtagtct tgaggcataa ctgatctcac aaagagttca gccttcagta    5220
gggttaatta tggaaagtct tggaagaatt ctcagagtgg ttctgggtgt ggtagacggg    5280
gacagcttag tagataagac gaattaaagc cctgatcaaa atgttttagt aggagaagta    5340
aaaagcaaag gcttgcgggg cgctgtggct cacgcctgta atcccagcac tttgggaggc    5400
tgaggtgggt ggatcacctg tggtcaggag ttcaagacca gcctgaccaa catggtgaaa    5460
ctcggtctct actaaaaata caaaaaaaaa aaaattagct gagtgtcatg gcgcatgcct    5520
gtagtcccag ctacttggga ggctgaggca ggagaattgc ttgaacccgg gaggcggagg    5580
ttgcaatgag ctgagatcac gccattgcac tccagcctgg gcaacagagt gagactccgt    5640
ctcaaaaaaa aaaaagcaa aggctgaatg aggccaagtg tggtggctca ctcccgcaat    5700
cccagcagtt tgggaggtga ggcaggagga tcacttgagg agtttgagac ttgcctgggc    5760
aacatagcaa gcccatctct attaaaaaaa aatgaaattt taagaaacat tgagtagaca    5820
gtatgagtga aagctgaaag aacatacaaa aaaacagcc atccaggcca tgacgagaag    5880
gagcctaact cttaacactc tgtctagacc tcaattctct cttatttgta tttatttatt    5940
tatttatttt tattttattt tttgagatgg agtctcagcc tgggctctgt tgcccaggct    6000
ggaatgcagt gtgcaatctt agctcactgt aacctccgcc tcccgagttc aagcgatttt    6060
cctgcctcag cctcctgggt ggctgagatt acaggcgtgc gacaccaagc ccagctagtg    6120 gtttttttt ttgaaatttt agtgagaggg gatttcacca tgttggtcag gcttgtctca    6180
aacttctgac cataaatgat ctgtgtgcct cggcccccc ccagagtgct gggattacag    6240
gcatgagcca ctgtgtctgg tctattctct cttttctgtc ttctatctta tgcttagtca    6300
gaatttctgc ttatttataa ctttgtttta ttcttgctcc cttgctccca ccaacatcat    6360
```

```
ggtctgggtt actgcatagt atcctgaact gatttgtgcc cctagtccca gctactcagg   6420
aggctgaggt gggggaatca gtagagccca ggattttgag gctgcagtga gctgtgatca   6480
caccactgta ctccatcctg ggagagagag ggagaccttg tctcaaaaaa aaaaaaaatt   6540
tacaaaaagg gagagactga ctgagaagac cagtgtgaac tagcccttga ctgggcccag   6600
ggaagaatgt tggtttgaaa ggagaacacc ctaaggaata tatagcaagt tatagtaatg   6660
gcccaataac aagcatatac ctaaacgagc ttttcctaaa cattcccgtg cctgttcttc   6720
atcatgcctt tttccgcaac acagtttggt ggagaaccat tgtcatatac ccggttcagc   6780
ctggctcggc aagtagatgg cgataacagt catgtggaga tgaaacttgc tgtagatgaa   6840
gaagaaaatg ctgacaataa cacaaaggcc aatgtcacaa aaccaaaaag gtgtagtgga   6900
agtatctgct atgggactat tgctgtgatc gtcttttcct tgattggtga gaatgaccat   6960
tccaaacttc aatgttttct ataaccaact ctgggaagtc tgttatgtca gctcagcata   7020
tagttatttt gtaccttttt tttttttttt ttttggaga cagaggctta ctctcttgcc   7080
taggctagag tgcagtggca ccatgttggc tcactgcaac ctcagcctcc caggtttaag   7140
cgattctctg ccttagcctc ctgagtagct gggactatag gcgcccacga ccacacctgg   7200
ctaatttttt tttttttttt tgagttggag tctcactctg tggctcaggc tggagtgcag   7260
tggcgtgatt tcggctcact gcaatctccg cctcccaggt tcaagcgatt cttctgcctc   7320
agcctcctga ggagctggga ctacaggcgt gcaccaccac acctggctaa tttttgtatt   7380
tttagtagag acggggtttc accatgttgg tcaggctggt ctctaactcc tgacctcgtg   7440
atctgcccgc ctcagcctcc cagagtgctg ggattacagg catgagccac tttcccgtcc   7500
actttatgcc ttttttaagtg ccactaggaa gacaatcatg agtagattct atacctgtca   7560
ttgaatttaa tctggttgga aagagagacc catgaattat ttcaatacga cgtgcaagtg   7620
ttttctttt atttatgtat ttttttgttt gctcccactc caccaggaag caaatgctac   7680
gctagaaaat atccgcagga cactggcggt gcagcagctc agtctcatgt ttcaagggggg   7740
tcttttggaa aaaactacct atgttttgaa taggtagcta tttgaaataa agctagtata   7800
taatttatta agtggtttaa agtatacaaa actgagatgc attatatact ttaaaactac   7860
ttagaatttg atgaaaacca gtattttcaa ggcttacctg aaaatattaa cagattaaca   7920
gggatagatt acaaatgaaa ttctgagttc agctctggaa cttgtctct ttaggattta   7980
tgattggcta cttgggctat tgtaaagggg tagaaccaaa aactgagtgt gagagactgg   8040
caggaaccga gtctccagtg agggaggagc caggagagga cttccctgca gcacgtcgct   8100
tatattggga tgacctgaag agaaagttgt cggagaaact ggacagcaca gacttcaccg   8160
gcaccatcaa gtgagtgcca gctgctgtgc aagtatctag acaagtaatt caagaattat   8220
gataggccac ggggaaacaa taatggtgac actgtgggga atggcttgtt agagaagaca   8280
agacttgtca tgtttagcta aagagggggaa ggggcctgta aaaaactgaa actatactgg   8340
tagggaaaaa ggtagaactt ctctggggag tctccttttt cttaaaaaat taataggccc   8400
ttgatgtttt ccccatcttt gtagcttatt gcttgctgtc attctctggc tctgattttt   8460
cttcttaacc tcttgtaacg ttgtactaag ctctgctttg ctgacaagga catcagtagc   8520
ttttctctgt tttaggaagc aacacatgcc agaagtagcc ttttcatct ccttgatcat   8580
gggtaactgc ctgccttaag tctctagtgc ttcttaattt ctgtgatact cacccattaa   8640
ccccctaggcc agtcagtatc cagagacaat gtctccctct ggtggaggct ggaatacggt   8700
ggcgtgctct catctcaccg cagcttcatc cccctaccat agcctcctga gtagctggga   8760
```

```
ctataagcac gcagcaccac acccagctaa tttttttttt ttttttttaag agatggagtc    8820
tcaccatgtc tcccaggccg gtctgttctt agatttttat ttatttactt atttattttg    8880
agatggagtc ttacgtgttg cccaggctgg agtgcagtgg cacgatttca gctcagtgca    8940
acctctgtct cccaggttta agcaattctc ctacctcagt ctcctgagta gctgagatca    9000
caggcttgta ccaccatgct ctgctaattt ttgtgggttt ttttttttgtt tgtttgtttt    9060
ttttttttgc agaaacggga tttcaccatg ttggccaggc tggtgtctaa ctcctgacct    9120
cagatgatcc tcctgtcttg gctcccaaag tgctgggaat taacaggatg gaggcactgc    9180
acctggccaa aatttctaat tttatattta tttatttatt ttaatttgta atgggctttt    9240
ctggcaaaaa ctagaaagca tgctagacaa attctaaaag agctgtaaca cttgtccata    9300
gagttttact atctttgcac atacatgcct ctgtgcaaag aataaattta tcttttcctt    9360
tttgcaagct tcctacactt acagtggtac tataattctt tagtcttaag ttatggcatt    9420
ttctacttca tctagttgat gcttttgtgt ttatttactg tacaccagac cttatggtta    9480
aagtgagagt atagtccacc ccacaaaaat gtaagaacta atatgctgag taaatagaaa    9540
gaagtatggg agatcggacc aaggagcagt tctgcttcag ggtattcaga tgcttcacaa    9600
gtaggtgaga attgaaacta tgcactctgt tcagcacagt attactatct tagattttat    9660
agtagatctg gaagctactc atttccccta aaactatcct aagcagatac attgtgttat    9720
gatgaggctc ttgaaggagt gctttgtagt gggtaaagaa gctttgaagt tacaagattt    9780
ggggcaaaat ttttttttctt ttgtgatatt ctggtcagtc tagaagtttt gggtcacagt    9840
tcatttatct gaactatgag ggataatatt ttgctttcaa aacaatttgt ttaatccttg    9900
acttaaatgt ttatttttaaa gtaaacttaa gttcatttaa aaggcatttt ctcctccagg    9960
ctgctgaatg aaaattcata tgtccctcgt gaggctggat ctcaaaaaga tgaaaatctt    10020
gcgttgtatg ttgaaaatca atttcgtgaa tttaaactca gcaaagtctg gcgtgatcaa    10080
cattttgtta agattcaggt caaagacagg tatgttgaaa gatggtaaac ttattttttat    10140
acaagtagct attttcaggt gtgctaaata tagcaaagac ttttttgttag tgttgttggc    10200
ttttttttga aatggagtct cgctctgttg cccaggctgg agtgcagtgg cacaatctct    10260
gctcactgca gcctttgcct tctgggttca agtgattctc ctgccttagc ctccagagca    10320
gctgggatta caggcgcacg ccaccacgcc cagctaattt ttgtattttt agtagaggtg    10380
ggatggtctc gaacttttga cctcaggtga tcagcccgcc tgggcctccc aaagtgctgg    10440
gattacaggc gtgagccacc gcatgcggcc caaaggcttt taaaataaaa atcaagctta    10500
agatttagag gtaaatttcc tcaagccaaa taatgcaaga catactaaat gtaagctatt    10560
gtgtttttg gaaggatgac cttaggctta ttttaactta atcttttaa cagcgctcaa    10620
aactcggtga tcatagttga taagaacggt agacttgttt acctggtgga gaatcctggg    10680
ggttatgtgg cgtatagtaa ggctgcaaca gttactgtaa gtaaggcaaa acagtgcatg    10740
agactcttcc ctattgaatc attcaaaact catcttttct gttcttagga gttataaatt    10800
tacctgtaaa atgtaaatga tcatgagata ttttggtttt caaccctcta atgcacagt    10860
caacatgcat tgtcttctct ctctaatcac tttcccatg tcctgtttta ttttttcttt    10920
atagtactgc tagcagctga cattatctat gcctttgttt ccattagaat gtgagccaga    10980
tgaagaatca tgggttagtt ctatttactg ccatgttgca gagctttgga gaatgcctga    11040
catacatagt agtatttgct aaacaaatgc atatcctccc tgtggggaca gatgtaaata    11100
```

-continued

```
tccatcttgg ctggggccta gtcttagctt gattcgttaa tgcttgatct tttctatttt    11160
ttgttttgag acagggtgtc actctgttgc cctagctgga gtgcagtggc gtgagcttgg    11220
ctcactgcat tctccaccac cacccaggct caagtgagcc tcttgagtag ctgagatgtc    11280
cagttaattt ttattttta ttttattatt attattatta ttattattat tattattatt    11340
tggtagagac agggttttgc catgttggcc aggctggtct tcaattgaaa ctcctgggct    11400
caggtgattc accaccctca gcctcccaaa gtgctgggat tacaggagga agctgcttcg    11460
cccagccctt gatcttttta aatttaggca aatatagtca aattaacaca gaaatagaga    11520
acagatagat agaataattt tcagcttaaa aatcacattt gtggctgggc gtggtggctc    11580
acgcctgtaa tcccagcact ttgggagtcc aaggtgggtg gatcacctaa ggtcagagct    11640
accagcctgg ccaacatggt gaactctatt aaaaatacaa aaattagcca ggcgtggtgg    11700
tgggtgcctg taatcccagc tacttgggag gctggggcag gagaatcgct tgaagccagg    11760
aggtggaggt tgcagtgagc ggatattgcg ccattgcact ccagcctgag caacaaaagc    11820
gaaattccat ctcaaaaaaa aaaaaatcac atttgtaagt caggcgtatc tctagtggat    11880
acctttcggg gctggtgcag ttctgtgttg attccttgcc tttctggata cttgtgcttt    11940 atcccttgc ctggctgcct ataagccagg agtttagaga tgggtaggtt gttctgttaa    12000
agaacattga agattttgt tcaacttcaa gctttctgta ttgagggctt ggttgttagt    12060
gtcagtttat ggctgttcat ctggactctt atgagcttag gaacatcatg acacatctaa    12120
agttggtgta tgcaagtcac tttgttgtaa tagatggtgt tttaattttg ggacagattt    12180
attatcagac ctttcagtta aaacctattt ctatgatgtc ctcaaggcta agattgttcc    12240
aggcctccag tcccatgacc agcctacata ggcctcttta atctaaatgc ccttcagatg    12300
aaaggcagca tgggataaaa gcatgaaaga cataggaggc caaaaatctt gatttattc    12360 caatagctct gacctaaaag ttgtaaagtt tttagaact catgtctttt ttaggccttg    12420
gcctcctttt atctcttact tgggttgcct gtcttaggtt tgatctataa cactcttctg    12480
tctcaagatt ttagagctgt tccgatacca taatgctcat taaatctaat gtctttgttc    12540
tagggtaaac tggtccatgc taattttggt actaaaaaag attttgagga tttatacact    12600
cctgtgaatg gatctatagt gattgtcaga gcagggaaaa tcacctttgc agaaaaggtg    12660
agtatgagtt attataatat taaatacagt acttttggta tcttactctt caggtaagtg    12720
atatttcttg ttaatattct tacattctga aaatcagcaa tcttaaactc tcataccaga    12780
taatataatt tattaaaatg ctcaacaaat gaagtaagtt ccacttacct aatcagaagt    12840
gcttaagttg aaagctattt ctctgtataa ctcagtttta cgcatataca gaattcagcc    12900 taaaagcat gtttataaaa agggaaaatt aatagccaaa acatacacaa ggaactagag    12960
tggaacatat caaaagacag tggtgatttc tgcattttta aaaaagtgg cagggctcac    13020 acctgtaatc ccaacacttt aggaggctga ggtgggagga ctgcttgagc cctggaggtt    13080
gtgagatgtg actcgtgcca ctccagcctg agtgacagtg agactcaaaa aagtggttgt    13140
cttagatggg tttttgttat tttcctttt tttttttttt tttttttgag acggagtctc    13200
ttgtcaccct ggctggagtg cagtggcgtg atctcagctc actgcaacct ccgcctccca    13260
ggttcaagtg atgctcctgc ctcagccttc tgagtagctg ggattacagg tgcccaccac    13320
caccatgcct ggctaatttt tgcattttta gtagagacag gtttcacga cgttggcctg    13380 gctggtcttg aactcctgac gtcaggtgat ccacctgcct tggcctccca gattgctggg    13440
attacaggtg tgagccacca ctcctggcct ttgttattct ttttttttt tttttttt    13500
```

```
gagagggagt tttgctctttt tgtccaggct ggagtgcagt ggcgcaattt tggctcactg    13560
caacctctgc cttatggttt caagcgattc tcctgcctca gcttcccaaa tagctgggaa    13620
tacaggcgcc agccactgcg cccagttaat ttttgtattt ttagtagaga cagggtttca    13680
ccatgttggc caggctggtc tcgaactcct gagcttgtga tccccctgcc tcagccttgc    13740
aaggtgttgg gattacaggc gtgagccacc actcctggcc cgttactctt attttgcaaa    13800
caagtgagtt aatttttcag gaagcaatta ataaattacc agataaacaa tttgaaatat    13860
ttggaagtat tataagttta gtcctctgta accatttggc ctttagcata atgtccagga    13920
tgtattctca tttcgtatga tcagatcttc attttctgag ctttatatgt tttcttttag    13980
gttgcaaatg ctgaaagctt aaatgcaatt ggtgtgttga tatacatgga ccagactaaa    14040
tttcccattg ttaacgcaga actttcattc tttggacatg tgagttattt cttgagtaaa    14100
tcaccgtttt gagttccttg agttgttctt ggattcctgt attagcagaa atagcactgt    14160
gtcttcctta actgctcttt tttctgggag ggcgttagca gtaagcaaga agatagatta    14220
cattgacttt gaggctttat tatttgttgc taaaagtact ttgtcaatag tgccttgaat    14280
ttgagaattt ccatatgcca tgaaaacagg agtcacattg tagagccact cagattttg    14340
aggcttcaag ttggtaaact aaggttgggc tgcagcctta taccaaacct gaatcttaca    14400
gagaagtttt gaggaagtat gtgatggagt gaattgctct tttgtttcc taggctcatc     14460
tggggacagg tgacccttac acacctggat tcccttcctt caatcacact cagtttccac    14520
catctcggtc atcaggattg cctaatatac ctgtccagac aatctccaga gctgctgcag    14580
aaaagctgtt tgggtaagtt tttatttgaa agcggtcttg catagtgagg ttttatgatt    14640
agggaagaac ggtaatatgt tgattaaaat gttaaacatg atgataattt tccacatttg    14700
ggaatttgga ggatggttag ctgttacctt ggtacagata taaatgaatt tttctctata    14760
aagagatctt aataatggac tttggactta taaacacagg agaataagga gacttataaa    14820
cccagtgaat tccttgtgca agattcctgg catagcttct gctcaagtac ttctgtgctg    14880
aagcacgatg cctatagcag cccattcagt tagtagagag aatctgttag aattcatatt    14940
gggataaaat cctattcccc gaaacatcca tttgtctgga ttttcttct aagcaatacg     15000
gtatgattcc agttaccttg tctatagatt gagaagcctt gcttcttatg atggtttcca    15060
gagaaaccat ttatggttgt ggctcgctcc tctggatatc ctccctgtaa cgttagtgtc    15120
tctctttaaa aacagagccc agttccatta gagtacgtag cattaatttt gatttggatg    15180
tggacatatt tatcatttcc tgttattaca ggatggagat ctagtttcag gcctttatga    15240
aagcatttat ctcctgtatg acataggttc tctgatcctg tttctttaac ataattggat    15300
agtgaaaata tattctactt gatagtctca aatgaagaac atctgtatat aaggagtata    15360
tgaaatacca tgactgttga tcatgctgag aggcctttag cataggggag tgtgtaacat    15420
accatgacta ttgataacgc taagaggcat ttagcatagg tgattttttt gactcattct    15480
acctaccacc tacaaatcgt aaccaacctg tgaagccagc gtcccatctt atccttatgt    15540
agtagggag taataatgtt tcaacctata tttatgtaag taagccgcct taggagcagc     15600
tattatttgg gtaacacaga ggaattagat aggggaagca caagattttt ttttattt      15660
gacagtctca ctctgttgcc caggcaggag tgcagtggca tgatcctggc tcactgcaac    15720
ctccacctcc tgggttcaag gaattctgcc tcggccttcc aaagtgctgg gattacaggc    15780
gtgagccacc gcacccagct gaggaatatt ttttataact gagctaagaa tgtgtactat    15840
```

```
ccttgttagt ggtgacagtt gggaaacata aaagtgtatt aatattcttt tatatattag    15900
aagaacttca ttttgagtcc atcttggtat gtattccaaa tataaactac gtaagtatgt    15960
ctggcagaaa ggcatagtta gagaagtgtt ttaaaatatt gcttaattaa tggtttccaa    16020
ttggctgcct gcagatcaaa gtaagacgca aatggttcac cactagagag taagtttttt    16080
tttgttttta ttttgttttg ttttgttttg ttttttttg agacaggact tgtgctctgt    16140
tgcccaggct ggagtgcagt ggcgtgatct cggctcactg cagcctccgc ctcccaggtt    16200
caagcgattc tcctcctcat cctccttagt agctgggatt acaggcgcat gccaccatgc    16260
ccagttaatt tttgtatttt tagtagagtc ggggtttcac catgtcggtc aggctggtct    16320
tgaactcctg accttgtgat ccacctgcct cagcctccca aagtgctggg attacagggg    16380
tgagccactt cgccgggctg agagtaagtt ttgtttatat gtcctcttaa tctgtaactt    16440
cactggacag gagtaaaccc tgggcaagga acaataactc agaacttacg cctgctttct    16500
gattctagga atatggaagg agactgtccc tctgactgga aaacagactc tacatgtagg    16560
atggtaacct cagaaagcaa gaatgtgaag ctcactgtga gcaatgtgct gaaagagata    16620
aaaattctta acatctttgg agttattaaa ggctttgtag aaccaggtaa agaccgcccc    16680
ccccccccgc cccgcttttt ttttgtttt cttttctgtt cctaaggatg tggctagaga    16740
aggagcgagt gtaggaatgc tggcttggct tggttttatg aagtgctcaa tcttgtctgt    16800
cctaaagtta attgtttatg tgttagtttc tttttttttt tttgagaaag agtttcactc    16860
ttgttgccca ggctggagtg cagtggtgtg atctcggctc actgcaattt ccgcctccca    16920
ggttcaagcc attctcctgc ctcagcctcc ccagtagctg ggattacagg catgcgccac    16980
cacgcctggc taattttgta ttttagtag agacagggt tctccatgtt ggtcaggctc    17040
catgaggtca gagctcctga cctcaggtga tctgcctccc tcagcctccc aaagtgctgg    17100
gattacaggc atgagccacc gcgcccagcc tatgtgtcag ttttattggg aggtaataag    17160
gccctaggaa attcttgtta aaaattgacc attatgacta gaaaatctat tctaagttat    17220
tgactagacc agtgataagc aaatttctta aggggcaga taataaacct tttgccaggc    17280
tatacagtct ctctttttagc tgttcaactc tgtgggagca agaaaacagg cacagactgt    17340
gcgtagtgaa tgggcatgcg ggctgtagtt tgccagtccc tggagttaac tttaaatgca    17400
atcaaacagc caacacttac taagaaataa gtccttggac ttaagtagtc agtaaattta    17460
attagtagtg taggaaaaaa gtagctctac tagtaaggta aaattaatat tctcatgtga    17520
atttttaatt cccagagttt ttagtcagat ttgaagtaag gctctttat ccttaataca    17580 tatactgtgc ttttaccttt ctactgatgt gctaattcta gaaaagttta gaagctgatt    17640
atataagttc tttcttcctc ttttttcttt tttaaagatc actatgttgt agttggggcc    17700
cagagagatg catgggcccc tggagctgca aaatccggtg taggcacagc tctcctattg    17760
aaacttgccc agatgttctc agatatggtc ttaaaggta gagtacaaat tttgattctt    17820
ttgaatattg gtgcactgca tacagttcta gatgttatac tgtgctttgc tcactttgcc    17880
tgcattcctg tggttctcat gctagactct agttcttaaa tacaaggcag attgtctttt    17940
gttgtagctg ccttttcctt tgaaacagct ttccataaag tgtcttaact gtgctagaaa    18000
tcaccagttt ctttgagaca gtggagttac tgagccctag tgcttagtgt ggtggatcca    18060
gagtgataag gtggatcata gtccctaagc aatctatttg aaagcagtag catacctctc    18120
tactcatgta ctgaggccta acagctattg aaatttgtt ctgttattc atttattcat    18180 tttttgagac agagtttcac tctgttgccc aggctggagt gcagtggtgt gatctcactt    18240
```

```
agctcactgc aacctctgcc tcccgacttc aagcaattct cctgcctcag cctcctgagt    18300
agctgggatt acaggcaccc acaaccacac ccggccaatt tttgtatttt tactagagac    18360
agggtttcgc catgttggcc aggctagtct cctgacctca agtgattcac ccgcctcagc    18420
ctcccaaaat gctgctagtg agccaccgtg ccctgcctct tttgtttatt tttgagcctt    18480
tctgtcctac tttccactct ttcacactcc tacccaccca cacattcaaa atcacgtcac    18540
attcttgaat ctttgggtct tagggcaaac tgcaatgctt aactttaata cagagtacat    18600
taatggagaa aaagatacag tgagggaagt gggagggatg gagggcagtg tgatacatgt    18660
aacctcaaaa ggtgctgtca caaatatagt ttctctgcaa actcttcttg taacttaaat    18720
ttgtgaattt ttattttatt ttagaattat tttttttaaaa atccaatgtt tggatttacc    18780
tctgaagatt tttctcaaga tgtgcatcat catgcttaca ctgttttcaa tgatctctgg    18840
gtccagaagt taaggaactc caagaatgaa attgtgaaag ggtgactact ggcccctgct    18900
atgtactcaa atcttatttt gcagatctcc tatcttgctc tttgtaggtt acttaaaaaa    18960
aaattattcc tattctttta ttcttttacc tggggtctca aaaaaagatt ttgttagttt    19020
ttttttttct ttttggctc agaaaaaaaa gattttggaa tctgctatct tggaattaga    19080
ccttctgatt catcttaagt gggatacctt ccatccttgt ctgtgtataa cctttcctca    19140
ggtaaagcta acttttttct ctttcagatg ggtttcagcc cagcagaagc attatctttg    19200
ccagttggag tgctggagac tttggatcgg ttggtgccac tgaatggcta gaggtattct    19260
ttatcatccc ttcccatatt ggacacgagc ttgtgggctt aggctgttgt ccagaagtga    19320
tgtttttata ggtttgattt taccactttt gcctttgcgt ttagtctcag tagagtccag    19380
aattgaaaat gaatccctaa tgctactgta tgtgataaat aaacagattt atacttatta    19440
gtgttttccc ttctcttcta gggatacctt tcgtccctgc atttaaaggc tttcacttat    19500
attaatctgg ataaagcggt tcttggtaag tatccctttc attagctgtt tatgaattca    19560
ggtaaacttt tttgagatgg agttttgctc ttgtcgccca gactggagtg caatggcacg    19620
atctcggctc actgcaacct ctgtctccca gattcaagcg attctcctgc cttagcctcc    19680
tgagtagctg ggattacagg tgctcactac cacacccagc taatttttg tatttttagt    19740
agagacaggg cttcactatg ttggccagat ggtctcgaac tcctgacctc aggcgatctg    19800
cctgccttgg cctgggatta cagatgtggg ccactgtgcc tggccagata aactacttga    19860
agtggaagaa agcttttttt ttttttgagac agagtctcac tgtattgccc aggctagagt    19920
gcagtggcac aatcttggct tcactgcagc cttgacctcc tgggtcagg tgatcctccc    19980
acttcagcca cctggctaat tttttttgta gagatggggt tttgccatgt tgcccaggct    20040
ggtgtcaaac tcctgagttc aagcattcta tgtcagctgc ccaaaatgct gcggttacag    20100
gcatgagcca ttgccctcag cctgtatctt aaccttcctt taaatagtct gtcaagttac    20160
acagtgagca caattgcttg tctagaacag tgggtagttc tcagtgtggc ccccagatga    20220
gtagcattag gaactgttac gaaatgcaaa ctgtcatgtc taccccagac ctttgagtca    20280
gaaatgggag tgttggtcta aaaactgggc ttttttgggct gggcgcagtg gtgcacgcct    20340
gtaatcccag cacttgggag gccaaggcag gcggatcacc tgaggtcagg agttcgagac    20400
cagcctggcc aacatggtga aaccccgtct ctactaaaaa taccaaaatt agccgggtgt    20460
ggtggcgagt acctgtaatc ccagctactc aggaggctga ggtaggagaa tcacttgaac    20520
ccgggaggca gaggttgcag tgagccaaga tggcgccatt gccctccagc ctgggcgaca    20580
```

```
gagcgagact cctctcaaaa aaacaaacaa aaaaactggg cttttttttt ggcaacccTt    20640
ggggaataaa aacctattat tttcttaagg acaaagtatc ctgaagcaaa aaaacccaaa    20700
caaagaaaca aaaaacttta acaagcacta caggtaattc tgatggacta aagttttagg    20760
accataagtc tggactatat tgaggtgaga agaaactaaa ctatgccata tagaatggta    20820
cttagagagt aattcacatc ctgttacgtt gtggcatcac tgatagaaat attggataat    20880
gaaacttcta gaagagtttg aatgttcact ggcagcagaa aattgacaaa agggtttgaa    20940
tgttatttaa agtgcagctg tccattcaac aggaatgggg taaaaaagaa agtgcagatg    21000
tagctgatga gctgagaata gtgaaatgtc tacatggggg aaaaaaggaa agagttacaa    21060
ttaaacctct ctaggttagt tatttccctg ttgtatgttt gccgcagaat gtgctgagta    21120
tagcaagcat actatgtata gctctaacct gggtgaacca gaaagttaaa catgaaattg    21180
ctaatggggg aggctgcaca tgtgtggggg cagtggattt atgggacctc taggtacctt    21240
tctcttaatt ttgctgctga acctaaaact ggtctgattt tttttttttt tttttttttt    21300
tttgagatgg agtctcgctt tgtcacccag gctggagtgc agtggcgcca tcccagctca    21360
ctgcaagctc cgcctcccgg gttcatgcca ttctcctgcc tcagcctccc gagtagctgg    21420
gactacaggt gcccgccacc acacccggct aattttttgt attttagta gagacggggt    21480 ttcaactgtg ccagccaaga tggtctcgat ctcctggacc ttgtgatcca cccgtctggg    21540
cctcccaaag tcctgggatt acaggcgtga gccaccgtgc ccggcctaac tgctctgata    21600
tttttaaaaa aggtgacttg gattaaagta tgcaaactca aggagtagta cgagcccact    21660
tgagtgaagt tagcttagtt gctaaagagc ttgataccaa aattattttg tttattgatg    21720
aatgggatag ttgttgcaca gggccactga tctagattac tgtcttattt gtcaagtact    21780
tatagttgta gaagtagcag tgtgaaaatt atcggaatgg agaaggggca atgataaaac    21840
aatttatttt caggtaccag caacttcaag gtttctgcca gcccactgtt gtatacgctt    21900
attgagaaaa caatgcaaaa tgtgagtata tacctcatta caaaaatgta tgacttaatt    21960
tttgttgaat caacctgaga taaaaaacac tgatatgtaa accgtagtca gtaacaaaaa    22020
ataggaattg agaataaatt ttatagcagc gttatttaag ggatacttgc ctattgaacc    22080
atatgagatg agggctccaa tcttaaagaa tatgttgttt atttaggaat atataacaaa    22140
atgccatgag gcctaagctg tagtgcaggg gcccacaggg gattgtctat agagtcacaa    22200
tgctaaggaa ggcttaaatc aacttgaact atactttgag aaggccggag gaaatattca    22260
ttgaataaac aattaccata gttttgaatg agggagagca tgtgaaagaa atatttgcc    22320 tatgtggggt ggggggaggg gagagggata gcattgggag atatacctaa cgctagatga    22380
cgagttagtg ggtgcagtgc accagcatgg cacatgtata catatgtaac taacctgcac    22440
aatgtgcaca tgtaccctaa aatttaaagt ataattaaaa aataaataaa taaataaata    22500
aaaaagaaaa tatttgccta atgggattag aggctgtata ttggagtgag taaagttaga    22560
aacaggtcag atagcagaca ttggccttga tccaagagat actagggatt ataggatctc    22620
aagcaaggtg atcatgaatt tgccagttag gttggtggca taagatgcac tagaaggaag    22680
aaaccagaaa caagataggc atagtgtgaa gcccagagag ggcttttaca attgtgggta    22740
agccaccatg gttttgtttg tttgtttgtt tgttttgag atggagtctt cctctgtctt    22800
cctccagcac tcaggctgga gtgcaatggt gcgatcttgg ctcactgcag cctccacctc    22860
ctgggttcaa gcgattctcc tgcctcagcc tcctgaggag ctgggactac aggtgcacac    22920
caccacacct ggctaatttt tgtattttta gtagagacgg ggtttcacca tgttggccag    22980
```

```
gatggtctca atcccttgac ctcatgatct cttgaccttg gcctcccaaa atgctgggat   23040
tacaggtgtg agccaccgcg cccagctttt attcattttt ttttccttt ttttttttaa    23100 gagataaagt cttgctgtgt tgcccaggct agtctcaaac ttctgggctc aagtgatcct   23160
cccagctcgg cctcccaaag tgttgggatt gcagttgtga actacccac ccggcctagg    23220 cccactttta aaatgttaat taagaagaaa acattttttc ctcaccataa ctaaaggaac   23280
tgacaacatg agcctagtta gtaataactt aaagttgaga ttgttttaac tatcataaat   23340
aatttctttt caagaagata taatacaagt tttttattta aaaattgtta tagagtaaca   23400
tgttagtgac tagcctgaat aaataagttc caaaaggtta gttttaatga aatttctta    23460 tcttacaggt gaagcatccg gttactgggc aatttctata tcaggacagc aactgggcca   23520
gcaaagtgta agttgagaaa agtgaatgaa caaactaata gaaaagcaga gattctacct   23580
actacattag gtagaatcta aatctgtcct tgcattgaac ttacttacac ctaaagatat   23640
tcagctaaag aatttatttt ggatgggggg actagcacga tagaacagtc tattcttaa    23700 aacactttct aaagacacat tctttgtctt tgcagtgaga aactcacttt agacaatgct   23760
gctttccctt tccttgcata ttctggaatc ccagcagttt ctttctgttt ttgcgaggta   23820
agtctgttca tttaaatgac aaatggagag aggctctcta aaaggaagtg atctgtattt   23880
gggaataggg cattgcaatg ggaatgcctg tgctatagtc aactatgtac atattcagag   23940
gagtaaagga aaacaagttt ttaaggacaa atgatgagga ttacaaaatt actttgaggt   24000
aattattctt ggctaccaag atcaataaca aggatgacac cagtccaagg ttgacaggca   24060
gttgctaggc agattttctc acgagagaag ttttttggtg caaggttgca gtggcctttg   24120
tgtaaggttg tagttttgt aaaaggaaa aaaaaccct taatccttgt tatcagacat       24180
acaagggtga gacccttctc ttcagggttg cattttgtt aacactagtg actccatttt     24240
gattttgaca acttgcacat atcttagttg ttgggttttt tttgtttgtt tttgttttg    24300 tttttttttt ttttttgaca atggtgactt gctctgtcac ccaggctggg gttgcagtgg   24360
cccgatcatg gctcactgca gcctcaagca gtcctccccc ttcagcctcc aaactgtttg   24420
gattataggc aagagctact tactacacct ggccatggat cttcttgtgt caactttgag   24480
accaaattta ctgcagtgct taaaatgttt taagaattat acacatgtgc tggatgtggt   24540
agctcacgcc tgtaatcctg tagcaggaca agccgcagac aaatcccctc agacaccgag   24600
ttaaagaagg aagggcttta tttggctggg agctttggca agactcacgt ctccaaaaac   24660
tgagctcccc gagtgagcaa ttcctgacct ttttaagggc ttacaactaa gggagtctgc   24720
gtgagagggt cgtgatcaat tgggcaagca gggggtacat gactggggt tgcatgtacc    24780 ggtaattaga acagaacaga acaggacggg attttcacag tgcttttcta tacaatgtct   24840
ggaatctata gataacataa ctggttaggt cagggctcga tctttaacca ggtccagggt   24900
gcggcagcgc tggctgtcc acctctgcct tttagttttt acttcttctt tctttggagg     24960
cagaaattgg gcataagaca atatgagggg tggtctcctc ccttaatccc agcactttgg   25020
gaggccaagg aaggcggatt acgaagtcag gagtttgaga ctagcctgac caaaatggtg   25080
aaaccccgtc tctgctaaaa atacaaaaat tagtcggaca tagtggcgtt gtgcctgtaa   25140
ccccagctac tcaggaggct gagcaggaga atcgcttgaa cctgggaagc agagttgcag   25200
tgagcctgag aatggaccac tgcactgcag ctggggttta gggtgacaga cgcttgggtg   25260
acagagcaag accctgtctc caaaaaaaaa agttatacac atgtaattat tgcatgttcc   25320
```

```
ttcattatta gttttaacaa ctagacttgt taatctcaat agcttaatta gcatttgagt    25380
ttattgctaa aattctttat gagttttaat aatgaggctt ggccgagtgt ggtgggtcat    25440
acctgtaatc ccagcatttg ggaggccaag gcgggtagat cacttgaggt caggagttca    25500
agaccagcct ggccaacatg gttaaacccc atctctacta aaaatacaaa aaattagct     25560 gggcatggtg gcacatgcct ataatcccag ctgctcagga ggctgaggtg aagaatcgc     25620 ttgaacccag ggggcagagg ttgcagtgag ccgagatcgt gccattgcac tctagcctgg    25680
gcaacagagc aagatcgtct aacaacaaca acaaaaaaac caaggctgaa tttcttgagt    25740
gattgagcag tggctatcta ttggacagtc cagctgaaca gtattttcc tcaggctggg     25800 tgcagtaact ctcacctata ttccggcaca ttgggtggct gaggtgggca gatcacttga    25860
ggccaggagt gagaccagcc tgggtaacgt gcctagacta tatctctaca aaaaattttt    25920
taaataaagc tgcccagtg gccagctgta gtcccaactc cttgggaggc tgaggcaggg     25980
gggtcacttg agctaggagc ttaaggctgt ggggagccat gattgcatca ccacgctcca    26040
gcctgggtga cagagtgact cgtctcaagg ctgcaggag ccatgattgc atcactgcac     26100
tccagcctgg gtgacagaga gaggcctcgt ctcaaggctg cggggagctg tgattgcatc    26160
actgcactct agcctgggtg acagagtgac ctcgtctcaa ggctagaggg agccatgatt    26220
gcatcactgc actccagcct gggtgacaga gagagacctc gtctcaaggc tgcagggagt    26280
catgattgca tcgctgcact ctagcctggg tgacagagac cttgtctcaa ggctgcgggg    26340
agtcatgatt gcattgctgc actctagcct gggtgacaga gagaccttgt ctcaaggctg    26400
tggggagtcg tgattgcatc actgcactct agcctgggtg acagagagac ctcgtctcaa    26460
ggtatgtttc atgtatcttc tcttttttca ttgataaagg cccaaacttc ccagagagaa    26520
aaacatacag ccttaaggaa tttggctaga agtctattca gggcatatga tacgatagaa    26580
cagggattct gtagaacctg gaagaaagta gtcaactcta ggagtaggtt agcttgagag    26640
aagtagcaag aatgtactta aagcagcaga taatgagata gaattggggt aaattgcggt    26700
aggaatatgt tagaagcaag ggtggaactg tcgtcactgt tacctcgatg gcgaagccag    26760
aatgtgaggc tcttgctctt agaactcacg tgagtaccat agcctcgcat tgtctcacag    26820
gacacagatt atccttattt gggtaccacc atggacacct ataaggaact gattgagagg    26880
attcctgagt tgaacaaagt ggcacgagca gctgcagagg tcgctggtca gttcgtgatt    26940
aaactaaccc atgatgttga attgaacctg gactatgaga ggtacaacag ccaactgctt    27000
tcatttgtga gggatctgaa ccaatacaga gcagacataa aggtgagcac tgattccaat    27060
tacgttttta ttttgctgaa tgtcaagtat tttgaaatgt gatgtgttcc tgtgtgttcc    27120
tgttggaagg gtgattgtag ccatagtaca ttttaaagtg aactgaggta taattgtatg    27180
tagaattggt aacttgtttg agagaagtcg ggaggctgtg gattagagac ctaggacaga    27240
gctcagcagg tgtttcagaa tccagagcag tgtcaggttt tctgtcactc atgtctccca    27300
ggcagcccgt cagtaggaca cggaatatga agatctcagc aaggagttgg gctgtgtgcc    27360
tctcgggcgt gacccggatg gaaagacagc acagctagca ggattccatc tcgtagtgat    27420
ctgcgcatct aaaagtcaaa tattctatta acgaaactg ataagcaggg tgaggtggtg     27480
catacccgta gccccagcta cttctgctga ggcaggagga ttgctggagt ccagcccagg    27540
caacatagca aaatcccatc tctaaataaa ttaataaaac taatattaaa gtagcttcca    27600
gattgtttta tggtactagg agttgatttt taacagatct cttaattgaa gtaaatcact    27660
gacaaccgaa tcttttata tcttttttat ttttattttt attttatttt ttttgagaga    27720
```

```
tgaagtctcg ctcttgtccc ccaggctgga atgcaatgac atgatctcgg ctcactgcaa   27780
cctccacctc ccggctttaa gcgattctcc tgcctcggct ccccaggtag ctgggattac   27840
aggcgtgtgc caccatgccc agatagtttt tgtgttttta agtagaagcc ggggttttac   27900
catgttggcc aggctgaagt gcagtggcga gatctcggct cactgtaaga tgcgcctccc   27960
gggttcacgc cattctcctg cctaagcctc ccgagtagct gggactacag gtgccggcca   28020
ccacgcccgg ctaattttt gtattttag tagagccggg gttttaccat gttggccagg   28080
ctggtcttga actcctgacc tcaggtgatc cacccacctc ggcctcccaa agtgctggga   28140
tcacaggcat gagccaccac gcccggcatc ttatgtcttt cttgaaacta attgtaactg   28200
ttgaaaatgg aacttaccag gtggaaataa ctaaatcctg aagtaccttg aaccaaaatg   28260
ttttccccta tagggacatt ttcctccaaa aggagaattg aactggaaac aatatagtac   28320
ataggattat ataattatgt tcaatttctt aatgagaatg gttttcttac atgctgggct   28380
caaatatgag tgtatatcac agtccataga gcttggaacc cctgtgcaag gtgctttcgg   28440
agtcttgagc ttatctgcga gttccttta tcagaatctt acttaacgca cgttaaatta   28500
gaaaggcata caaagaatg tccttagaaa taaaacttct catagcgaat aatgtctgtt   28560
tcaggaaatg ggcctgagtt tacagtggct gtattctgct cgtggagact tcttccgtgc   28620
tacttccaga ctaacaacag atttcgggaa tgctgagaaa acagacagat ttgtcatgaa   28680
gaaactcaat gatcgtgtca tgagagtaag tgaacttttg ggaaaggagg aactaaagta   28740
tgtgtaaaat aaccgataaa tcttacactt ctgcaaagtg gacaaactct aggagtctag   28800
aattccttta agaagggagc attaatggtt tagctgtcat tttctgtttc tgctgtctaa   28860
ttcagaactt agtcaaacct agtcttttg gaagagactt gctgtaaaac ttccatgtat   28920
gctccaatgg ggaaaagatc tgaacacatt taaagttttc ctttgtaaaa tgaatcagtt   28980
tcctttaaaa aaaattttt tttttgaga cagagtttca ctgttgttgc ccaagctgga   29040
gtgcaatggc acggtctcgg ctcactgcac cctccacctc ccaggttcaa gtgattctcc   29100
tgccttagcc tcccgagttg ctgtgattac aggtgcccaa caccacgccc ggctcatttt   29160
ttgtattttt agtagaaacg gagtttcacc atgttagcca ggccggtctc gaactcccaa   29220
cctcaagtga tccacctgcc ttggcctccc aaagtactgg tattacaagc gtgagccgct   29280
gtgcccagcc tccttagaa ttttaacctt agaagattag cattagcctg attctcagca   29340 ttctttttc cttactctgc tatagaaagt ctgatcagct ggctgggtac agtggctcat   29400
gcctgtaatt ccagtacttt gggaggccga ggcaagcgga tcacctgagg tcaggagttc   29460
aagaccagcc tgaccaacat ggagaaaccc catctctact aaaaatacaa aaattagctg   29520
ggcgtggtgg tgcatgcctg taattccagc tgctcaggag gctgaggcag gagaattact   29580
tgaacccggg aggtggaggt tgcagtgagc tgagatcgcg ccattgtact ccagcctggg   29640
caacaagagc gaaactctgt ctcaacaaca acaaaaagcc gggcacggtg gctcacacct   29700
gtaatcccag catgaattgc ttgaactcgg gaggtggagg gtaccagtga gccgagatag   29760
cgctgttgca ctccagtctg ggcaacaaga gcgaaactct gtgtcaaaaa aaaaaaaaa   29820 aaaaaagtct gatcggcatt cttaaatttg gacatttta catttgaagt gaactgttgt   29880
tttactacaa aagtcacagg gctgtgtaaa ttgccttgtg tgttgttttc gtaggtggag   29940
tatcacttcc tctctcccta cgtatctcca aaagagtctc cttttccgaca tgtcttctgg   30000 ggctccggct ctcacacgct gccagcttta ctggagaact tgaaactgcg taaacaaaat   30060
```

| | | | | | |
|---|---|---|---|---|---|
| aacggtgctt | ttaatgaaac | gctgttcaga | aaccagttgg | ctctagctac | ttggactatt | 30120 |
| cagggagctg | caaatgccct | ctctggtgac | gtttgggaca | ttgacaatga | gttttaaatg | 30180 |
| tgatacccat | agcttccatg | agaacagcag | ggtagtctgg | tttctagact | tgtgctgatc | 30240 |
| gtgctaaatt | ttcagtaggg | ctacaaaacc | tgatgttaaa | attccatccc | atcatcttgg | 30300 |
| tactactaga | tgtctttagg | cagcagcttt | taatacaggg | tagataacct | gtacttcaag | 30360 |
| ttaaagtgaa | taaccactta | aaaaatgtcc | atgatggaat | attcccctat | ctctagaatt | 30420 |
| ttaagtgctt | tgtaatggga | actgcctctt | tcctgttgtt | gttaatgaaa | atgtcagaaa | 30480 |
| ccagttatgt | gaatgatctc | tctgaatcct | aagggctggt | ctctgctgaa | ggttgtaagt | 30540 |
| ggtcgcttac | tttgagtgat | cctccaactt | catttgatgc | taaataggag | ataccaggtt | 30600 |
| gaaagacctt | ctccaaatga | gatctaagcc | tttccataag | gaatgtagct | ggtttcctca | 30660 |
| ttcctgaaag | aaacagttaa | cttcagaag | agatgggctt | gttttcttgc | caatgaggtc | 30720 |
| tgaaatggag | gtccttctgc | tggataaaat | gaggttcaac | tgttgattgc | aggaataagg | 30780 |
| ccttaatatg | ttaacctcag | tgtcatttat | gaaaagaggg | gaccagaagc | caaagactta | 30840 |
| gtatattttc | ttttcctctg | tcccttcccc | cataagcctc | catttagttc | tttgttattt | 30900 |
| ttgtttcttc | caaagcacat | tgaaagagaa | ccagtttcag | gtgtttagtt | gcagactcag | 30960 |
| tttgtcagac | tttaaagaat | aatatgctgc | caaattttgg | ccaaagtgtt | aatcttaggg | 31020 |
| gagagctttc | tgtcctttg | gcactgagat | atttattgtt | tatttatcag | tgacagagtt | 31080 |
| cactataaat | ggtgttttt | taatagaata | taattatcgg | aagcagtgcc | ttccataatt | 31140 |
| atgcacagtta | tactgtcggt | tttttttaaa | taaaagcagc | atctgctaat | aaaacccaac | 31200 |
| agatcctgga | agttttgcat | ttatggtcaa | cacttaaggg | ttttagaaaa | cagccgtcag | 31260 |
| ccaaatgtaa | ttgaataaag | ttgaagctaa | gatttagaga | tgaattaaat | ttaattaggg | 31320 |
| gttgctaaga | agcgagcact | gaccagataa | gaatgctggt | tttcctaaat | gcagtgaatt | 31380 |
| gtgaccaagt | tataaatcaa | tgtcacttaa | aggctgtggt | agtactcctg | caaaatttta | 31440 |
| tagctcagtt | tatccaaggt | gtaactctaa | ttcccatttt | gcaaaatttc | cagtacctt | 31500 |
| gtcacaatcc | taacacatta | tcgggagcag | tgtcttccat | aatgtataaa | gaacaaggta | 31560 |
| gttttacct | accacagtgt | ctgtatcgga | gacagtgatc | tccatatgtt | acactaaggg | 31620 |
| tgtaagtaat | tatcgggaac | agtgtttccc | ataattttct | tcatgcaatg | acatcttcaa | 31680 |
| agcttgaaga | tcgttagtat | ctaacatgta | tcccaactcc | tataattccc | tatcttttag | 31740 |
| ttttagttgc | agaaacattt | tgtggcatta | agcattgggt | gggtaaattc | aaccactgta | 31800 |
| aaatgaaatt | actacaaaat | ttgaaattta | gcttgggttt | ttgttacctt | tatggtttct | 31860 |
| ccaggtcctc | tacttaatga | gatagtagca | tacatttata | atgttgcta | ttgacaagtc | 31920 |
| atttttaactt | tatcacatta | tttgcatgtt | acctcctata | aacttagtgc | ggacaagttt | 31980 |
| taatccagaa | ttgaccttt | gacttaaagc | aggggactt | tgtatagaag | gtttgggggc | 32040 |
| tgtggggaag | gagagtcccc | tgaaggtctg | acacgtctgc | ctacccattc | gtggtgatca | 32100 |
| attaaatgta | ggtatgaata | agttcgaagc | ttcgtgagtg | aaccatcatt | ataaacgtga | 32160 |
| tgatcagctg | tttgtcatag | gcagttgga | aacggcctc | tagggaaaag | ttcatagggt | 32220 |
| ctcttcaggt | tcttagtgtc | acttacctag | atttacagcc | tcacttgaat | gtgtcactac | 32280 |
| tcacagtctc | tttaatcttc | agttttatct | ttaatctcct | cttttatctt | ggactgacat | 32340 |
| ttagcgtagc | taagtgaaaa | ggtcatagct | gagattcctg | gttcgggtgt | tacgcacacg | 32400 |
| tacttaaatg | aaagcatgtg | gcatgttcat | cgtataacac | aatatgaata | cagggcatgc | 32460 |

```
attttgcagc agtgagtctc ttcagaaaac ccttttctac agttagggtt gagttacttc    32520
ctatcaagcc agtaccgtgc taacaggctc aatattcctg aatgaaatat cagactagtg    32580
acaagctcct ggtcttgaga tgtcttctcg ttaaggagat gggccttttg gaggtaaagg    32640
ataaaatgaa tgagttctgt catgattcac tattctagaa cttgcatgac ctttactgtg    32700
ttagctcttt gaatgttctt gaaattttag actttctttg taaacaaatg atatgtcctt    32760
atcattgtat aaaagctgtt atgtgcaaca gtgtggagat tccttgtctg atttaataaa    32820
atacttaaa                                                            32829
```

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Tyr Trp Met Gln
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Val Tyr Pro Gly Asp Gly Asp Thr Arg Phe Ser Gln Lys Phe Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Arg Arg Arg Val Tyr Tyr Gly Ser Asn Tyr Ile Tyr Ala Leu Asp
1               5                   10                  15

Tyr

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Asn Val Gly Ser Ala
1               5

<210> SEQ ID NO 23
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 23

Gln Gln Tyr Ser Ser Tyr Pro Leu Ala Phe
1               5                   10

<210> SEQ ID NO 24
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Lys Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Val Tyr Pro Gly Asp Gly Asp Thr Arg Phe Ser Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ser Ser Glu Asp Ser Ala Val Tyr Phe Cys
                85                  90                  95

Ala Arg Arg Arg Val Tyr Tyr Gly Ser Asn Tyr Ile Tyr Ala Leu Asp
            100                 105                 110

Tyr Trp Gly Gln Gly Thr Ser Val Thr Val Ser Ala Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Val Pro Lys Gly Glu Phe Gln His Thr Gly Gly Arg Tyr
225                 230                 235

<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Met Thr Gln Ser Gln Lys Phe Met Ser Thr Ser Ile Gly
1               5                   10                  15

```
Asp Arg Val Ser Ile Thr Cys Lys Ala Ser Gln Asn Val Gly Ser Ala
        20                  25                  30

Val Ala Trp Tyr Gln Lys Pro Gly Gln Ser Pro Lys Leu Leu Ile
            35                  40                  45

Tyr Ser Ala Ser Asn Arg Tyr Thr Gly Val Pro Asp Arg Phe Ile Gly
 50                  55                  60

Ser Glu Ser Gly Thr Asp Phe Thr Leu Thr Ile Ser Asn Met Gln Ser
 65                  70                  75                  80

Glu Asp Leu Ala Asp Tyr Phe Cys Gln Gln Tyr Ser Tyr Pro Leu
                85                  90                  95

Ala Phe Gly Ala Gly Thr Lys Leu Glu Leu Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Leu Asn Asp Ile Phe Glu Ala Gln Lys Ile Glu Trp His Glu
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

Gly Thr Gly Ser Gly Thr Gly
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Ser Gly
1

<210> SEQ ID NO 30
<211> LENGTH: 151
<212> TYPE: PRT
<213> ORGANISM: Junin mammarenavirus

<400> SEQUENCE: 30

Pro His Asp Leu Pro Leu Cys Thr Leu Asn Lys Ser His Leu Tyr
1               5                   10                  15

Ile Lys Gly Gly Asn Ala Ser Phe Lys Ile Ser Phe Asp Asp Ile Ala
                20                  25                  30

Val Leu Leu Pro Glu Tyr Asp Val Ile Ile Gln His Pro Ala Asp Met
            35                  40                  45

Ser Trp Cys Ser Lys Ser Asp Asp Gln Ile Trp Leu Ser Gln Trp Phe
    50                  55                  60

Met Asn Ala Val Gly His Asp Trp Tyr Leu Asp Pro Pro Phe Leu Cys
65                  70                  75                  80

Arg Asn Arg Thr Lys Thr Glu Gly Phe Ile Phe Gln Val Asn Thr Ser
                85                  90                  95

Lys Thr Gly Ile Asn Glu Asn Tyr Ala Lys Lys Phe Lys Thr Gly Met
            100                 105                 110

His His Leu Tyr Arg Glu Tyr Pro Asp Ser Cys Leu Asp Gly Lys Leu
        115                 120                 125

Cys Leu Met Lys Ala Gln Pro Thr Ser Trp Pro Leu Gln Cys Pro Leu
    130                 135                 140

Asp His Val Asn Thr Leu His
145                 150

<210> SEQ ID NO 31
<211> LENGTH: 162
<212> TYPE: PRT
<213> ORGANISM: Machupo mammarenavirus

<400> SEQUENCE: 31

Ser Asn Glu Leu Pro Ser Leu Cys Met Leu Asn Asn Ser Phe Tyr Tyr
1               5                   10                  15

Met Arg Gly Gly Val Asn Thr Phe Leu Ile Arg Val Ser Asp Ile Ser
                20                  25                  30

Val Leu Met Lys Glu Tyr Asp Val Ser Ile Tyr Glu Pro Glu Asp Leu
            35                  40                  45

Gly Asn Cys Leu Asn Lys Ser Asp Ser Ser Trp Ala Ile His Trp Phe
        50                  55                  60

Ser Asn Ala Leu Gly His Asp Trp Leu Met Asp Pro Pro Met Leu Cys
65                  70                  75                  80

Arg Asn Lys Thr Lys Lys Glu Gly Ser Asn Ile Gln Phe Asn Ile Ser

```
                    85                  90                  95
Lys Ala Asp Asp Ala Arg Val Tyr Gly Lys Lys Ile Arg Asn Gly Met
                100                 105                 110

Arg His Leu Phe Arg Gly Phe His Asp Pro Cys Glu Glu Gly Lys Val
                115                 120                 125

Cys Tyr Leu Thr Ile Asn Gln Cys Gly Asp Pro Ser Ser Phe Asp Tyr
                130                 135                 140

Cys Gly Val Asn His Leu Ser Lys Cys Gln Phe Asp His Val Asn Thr
145                 150                 155                 160

Leu His

<210> SEQ ID NO 32
<211> LENGTH: 149
<212> TYPE: PRT
<213> ORGANISM: Tacaribe mammarenavirus

<400> SEQUENCE: 32

Ser His Glu Leu Pro Met Leu Cys Leu Ala Asn Lys Thr His Leu Tyr
1               5                   10                  15

Leu Lys Ser Gly Arg Ser Ser Phe Lys Ile Asn Ile Asp Ser Val Thr
                20                  25                  30

Val Leu Thr Arg Ser Ala Asp Val Phe Val His Ser Pro Lys Leu Gly
                35                  40                  45

Ser Cys Phe Glu Ser Asp Glu Glu Trp Val Val Ala Trp Trp Ile Glu
        50                  55                  60

Ala Ile Gly His Arg Trp Asp Gln Asp Pro Gly Leu Leu Cys Arg Asn
65                  70                  75                  80

Lys Thr Lys Thr Glu Gly Lys Leu Ile Gln Ile Asn Ile Ser Arg Ala
                85                  90                  95

Asp Gly Asn Val His Tyr Gly Trp Arg Leu Lys Asn Gly Leu Asp His
                100                 105                 110

Ile Tyr Arg Gly Arg Glu Glu Pro Cys Phe Glu Gly Gln Gln Cys Leu
                115                 120                 125

Ile Lys Ile Gln Pro Glu Asp Trp Pro Thr Asp Cys Lys Ala Asp His
                130                 135                 140

Thr Asn Thr Phe Arg
145

<210> SEQ ID NO 33
<211> LENGTH: 153
<212> TYPE: PRT
<213> ORGANISM: Guanarito mammarenavirus

<400> SEQUENCE: 33

Phe His Glu Leu Pro Ser Leu Cys Arg Val Asn Asn Ser Tyr Ser Leu
1               5                   10                  15

Ile Arg Leu Ser His Asn Ser Asn Gln Ala Leu Ser Val Glu Tyr Val
                20                  25                  30

Asp Val His Pro Val Leu Cys Ser Ser Pro Thr Ile Leu Asp Asn
                35                  40                  45

Tyr Thr Gln Cys Ile Lys Gly Ser Pro Glu Phe Asp Trp Ile Leu Gly
        50                  55                  60

Trp Thr Ile Lys Gly Leu Gly His Asp Phe Leu Arg Asp Pro Arg Ile
65                  70                  75                  80

Cys Cys Glu Pro Lys Lys Thr Thr Asn Ala Glu Phe Thr Phe Gln Leu
                85                  90                  95
```

```
Asn Leu Thr Asp Ser Pro Glu Thr His His Tyr Arg Ser Lys Ile Glu
            100                 105                 110

Val Gly Ile Arg His Leu Phe Gly Asn Tyr Ile Thr Asn Asp Ser Tyr
        115                 120                 125

Ser Lys Met Ser Val Val Met Arg Asn Thr Thr Trp Glu Gly Gln Cys
130                 135                 140

Ser Asn Ser His Val Asn Thr Leu Arg
145                 150

<210> SEQ ID NO 34
<211> LENGTH: 161
<212> TYPE: PRT
<213> ORGANISM: Sabia mammarenavirus

<400> SEQUENCE: 34

Phe Glu Asp His Pro Thr Ser Cys Met Val Asn His Ser Thr Tyr Tyr
1               5                   10                  15

Val His Glu Asn Lys Asn Ala Thr Trp Cys Leu Glu Val Ser Val Thr
            20                  25                  30

Asp Val Thr Leu Leu Met Ala Glu His Asp Arg Gln Val Leu Asn Asn
        35                  40                  45

Leu Ser Asn Cys Val His Pro Ala Val Glu His Arg Ser Arg Met Val
    50                  55                  60

Gly Leu Leu Glu Trp Ile Phe Arg Ala Leu Lys Tyr Asp Phe Asn His
65                  70                  75                  80

Asp Pro Thr Pro Leu Cys Gln Lys Gln Thr Ser Thr Val Asn Glu Thr
                85                  90                  95

Arg Val Gln Ile Asn Ile Thr Glu Gly Phe Gly Ser His Gly Phe Glu
            100                 105                 110

Asp Thr Ile Leu Gln Arg Leu Gly Val Leu Phe Gly Ser Arg Ile Ala
        115                 120                 125

Phe Ser Asn Ile Gln Asp Leu Gly Lys Lys Arg Phe Leu Leu Ile Arg
    130                 135                 140

Asn Ser Thr Trp Lys Asn Gln Cys Glu Met Asn His Val Asn Ser Met
145                 150                 155                 160

His

<210> SEQ ID NO 35
<211> LENGTH: 157
<212> TYPE: PRT
<213> ORGANISM: Chapare mammarenavirus

<400> SEQUENCE: 35

Phe Glu Asp His Pro Ile Ser Cys Thr Val Asn Lys Thr Leu Tyr Tyr
1               5                   10                  15

Ile Arg Glu Ser Glu Asn Ala Thr Trp Cys Val Glu Ile Ala Ala Leu
            20                  25                  30

Asp Met Ser Val Leu Leu Ser Pro His Asp Pro Arg Val Met Gly Asn
        35                  40                  45

Leu Ser Asn Cys Val His Pro Asp Ile Lys His Arg Ser Glu Leu Leu
    50                  55                  60

Gly Leu Leu Glu Trp Ile Leu Arg Ala Leu Lys Tyr Asp Phe Leu Asn
65                  70                  75                  80

Tyr Pro Pro Leu Leu Cys Glu Lys Val Thr Ser Ser Val Asn Glu Thr
                85                  90                  95
```

-continued

```
Arg Ile Gln Ile Asn Val Ser Asp Ser Ala Gly Ser His Asp Phe Lys
                100                 105                 110

Glu Thr Met Leu Gln Arg Leu Ala Ile Leu Phe Gly Thr Lys Leu Met
        115                 120                 125

Phe Asp Lys Thr Pro Lys Gln Phe Ile Val Ile Arg Asn Gln Thr Trp
    130                 135                 140

Val Asn Gln Cys Lys Ser Asn His Val Asn Thr Leu His
145                 150                 155

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Ala Ser
1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ala Ser
1

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ala Ser
1
```

COMPOSITIONS AND METHODS FOR TREATING ARENAVIRUS INFECTION

CROSS-REFERENCE TO RELATED APPLICATION

This application is the U.S. national phase application, pursuant to 35 U.S.C. § 371, of PCT International Application Ser. No.: PCT/US2017/036395, filed Jun. 7, 2017, designating the United States and published in English, which claims priority under 35 U.S.C. § 119(e) to U.S. Provisional Patent Application No. 62/392,729, filed Jun. 8, 2016, the entire contents of which are hereby incorporated by reference herein.

STATEMENT OF RIGHTS TO INVENTIONS MADE UNDER FEDERALLY SPONSORED RESEARCH

This invention was made with government support under Grant Numbers CA013202 and AI109740 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Sep. 29, 2020, is named 167705_010302_US_SL.txt and is 77,649 bytes in size.

BACKGROUND OF THE INVENTION

In the Western hemisphere, there are at least five arenaviruses that cause human viral hemorrhagic fevers with high case fatality rates. The pathogenic New World arenaviruses include the Junin (JUNV), Machupo (MACV), Guanarito (GTOV), and Sabia (SBAV) viruses, which, respectively, cause Argentine (AHF), Bolivian, Venezuelan, and "Brazilian" hemorrhagic fever, as well as the most recently described member, Chapare virus (CHPV). Of these, Junin virus (JUNV) is the only hemorrhagic fever virus for which transfusion of JUNV survivor immune plasma containing JUNV neutralizing antibodies ('passive immunity') is an established treatment. At present, no treatments exist for MACV, GTOV, and SBAV arenavirus infection, and no therapeutic strategies are available to address the threat of future emerging arenaviruses or arenavirus weaponization.

Accordingly, compositions and methods for treating or preventing arenavirus infection are urgently required, and methods for identifying therapeutic agents for treating or preventing arenavirus infection are urgently needed.

SUMMARY OF THE INVENTION

The invention generally provides compositions and methods of treating or preventing an arenavirus infection, including inhibiting binding of an arenavirus glycoprotein 1 (GP1) polypeptide to transferrin receptor 1 (TfR1) and inhibiting attachment of an arenavirus to a cell. Also provided are methods of designing or identifying therapeutic agents useful for inhibiting binding of an arenavirus glycoprotein 1 (GP1) polypeptide to transferrin receptor 1 (TfR1) by targeting a GP1 receptor-binding site (RBS), and therapeutic agents identified using the methods.

In one aspect, the invention provides a method of inhibiting or preventing binding of a transferrin receptor 1 (TfR1) and a glycoprotein 1 (GP1) of one species of New World arenavirus involving contacting a TfR1 with an antibody or antigen-binding fragment thereof generated by an immune response to a glycoprotein 1 (GP1) of a second species of New World arenavirus.

In another aspect, the invention provides a method of treating or preventing a New World arenavirus infection involving administering to a subject infected or at risk of infection with one species of New World arenavirus an antibody or antigen-binding fragment thereof generated by an immune response to a second species of New World arenavirus.

In another aspect, the invention provides a method of treating or preventing a New World arenavirus infection, involving administering to a subject in need thereof the isolated antibody or antigen-binding fragment thereof according to any aspect delineated herein.

In another aspect, the invention provides a method of inhibiting or preventing binding of a transferrin receptor 1 (TfR1) and an arenavirus glycoprotein 1 (GP1), involving contacting a TfR1 with the isolated antibody or antigen-binding fragment thereof according to any aspect delineated herein.

In one aspect, the invention provides an isolated antibody or antigen-binding fragment thereof that specifically binds arenavirus glycoprotein 1 (GP1), the antibody having one or more complementary determining regions (CDR) selected from

```
                                            (SEQ ID NO: 1)
CDR H1 sequence GFTFGTSI (e.g., CR1-07 CDR H1)

(SEQ ID NO: 2)
CDR H2 sequence ISHDESRK (e.g., CR1-07 CDR H2)

(SEQ ID NO: 3)
CDR H3 sequence AKDLSPPYSYAWDIFQYW (e.g., CR1-07 CDR H3)

(SEQ ID NO: 4)
CDR L1 sequence QSVLYSSRSDNKY (e.g., CR1-07 CDR L1)

(SEQ ID NO: 36)
CDR L2 sequence WAS (e.g., CR1-07 CDR L2)

(SEQ ID NO: 5)
CDR L3 sequence QQYYSSPPTF (e.g., CR1-07 CDR L3)

(SEQ ID NO: 6)
CDR H1 sequence GFTFSSA (e.g., CR1-28 CDR H1)

(SEQ ID NO: 7)
CDR H2 sequence IWSDGSNE (e.g., CR1-28 CDR H2)

(SEQ ID NO: 8)
CDR H3 sequence ATDKTYVSGYTSTWYYFNY (e.g., CR1-28 CDR H3)

(SEQ ID NO: 9)
CDR L1 sequence QSIDNW (e.g., CR1-28 CDR L1)

(SEQ ID NO: 37)
CDR L2 sequence KAS (e.g., CR1-28 CDR L2),
and (SEQ ID NO: 10)
CDR L3 sequence QHRT (e.g., CR1-28 CDR L3).
```

In another aspect, the invention provides an isolated polynucleotide encoding one or more sequences of an isolated antibody or antigen-binding fragment thereof according to any aspect delineated herein.

In another aspect, the invention provides an isolated vector containing the polynucleotide according to any aspect delineated herein.

In another aspect, the invention provides an isolated cell containing the vector according to any aspect delineated herein (e.g., expressing an antibody or antigen-binding fragment thereof according to any aspect delineated herein).

In another aspect, the invention provides an immunogenic composition containing a polypeptide having a TfR1 binding site of a New World arenavirus GP1, wherein the TfR1 binding site includes amino acids 87-235 of JUNV GP1 or corresponding amino acids of an arenavirus GP1.

In another aspect, the invention provides a vaccine containing a polypeptide having a TfR1 binding site of a New World arenavirus GP1, wherein the TfR1 binding site includes amino acids 87-235 of JUNV GP1 or corresponding amino acids of an arenavirus GP1.

In another aspect, the invention provides a method of generating an immune response in a subject involving administering to the subject the immunogenic composition or vaccine according to any aspect delineated herein.

In another aspect, the invention provides an in silico method for identifying an agent that inhibits binding of a New World arenavirus GP1 to a transferrin receptor involving a) generating a three-dimensional representation of a transferrin receptor structural binding pocket using the atomic coordinates of a New World arenavirus surface envelope glycoprotein amino acid residues in the sequence; and b) employing the three-dimensional structure to design or select an agent that inhibits binding, including for example, the atomic coordinates provided at Protein Database (PDB) ID 3KAS; and at PDB ID 5EN2. The atomic coordinates for the antibody CR1-10/JUNV GP1/antibody CR1-28 complex are provided at Protein Database (PDB) ID 5W1K; and the atomic coordinates for the antibody MACV GP1/antibody CR1-07 complex are provided at Protein Database (PDB) ID 5W1M. The atomic coordinates of the protein structure of an unliganded Fab fragment of CR1-07 is provided at Protein Database (PDB) ID 5W1G. The atomic coordinates provided at PDB ID 5W1K and at PDB ID 5W1M were previously described and set forth in 'pdb' and 'txt' files as Appendices A and B presented in compact discs (CDs), incorporated by reference into the disclosure of priority application number U.S. 62/392,729, filed Jun. 8, 2016, the entire contents of which are incorporated by reference herein.

In another aspect, the invention provides a kit containing the antibody or antigen-binding fragment thereof according to any aspect delineated herein, the polynucleotide according to any aspect delineated herein, the vector according to any aspect delineated herein, the cell according to any aspect delineated herein, the immunogenic composition according to any aspect delineated herein or the vaccine according to any aspect delineated herein.

In various embodiments of any aspect delineated herein, the antibody or antigen-binding fragment thereof has one or more complementary determining regions (CDR) selected from

```
                                            (SEQ ID NO: 1)
CDR H1 sequence GFTFGTSI (e.g., CR1-07 CDR H1)

(SEQ ID NO: 2)
CDR H2 sequence ISHDESRK (e.g., CR1-07 CDR H2)

(SEQ ID NO: 3)
CDR H3 sequence AKDLSPPYSYAWDIFQYW (e.g., CR1-07 CDR H3)

(SEQ ID NO: 4)
CDR L1 sequence QSVLYSSRSDNKY (e.g., CR1-07 CDR L1)

(SEQ ID NO: 36)
CDR L2 sequence WAS (e.g., CR1-07 CDR L2)

(SEQ ID NO: 5)
CDR L3 sequence QQYYSSPPTF (e.g., CR1-07 CDR L3)

(SEQ ID NO: 6)
CDR H1 sequence GFTFSSA (e.g., CR1-28 CDR H1)

(SEQ ID NO: 7)
CDR H2 sequence IWSDGSNE (e.g., CR1-28 CDR H2)

(SEQ ID NO: 8)
CDR H3 sequence ATDKTYVSGYTSTWYYFNY (e.g., CR1-28 CDR H3)

(SEQ ID NO: 9)
CDR L1 sequence QSIDNW (e.g., CR1-28 CDR L1)

(SEQ ID NO: 37)
CDR L2 sequence KAS (e.g., CR1-28 CDR L2),
and (SEQ ID NO: 10)
CDR L3 sequence QHRT (e.g., CR1-28 CDR L3).
```

In various embodiments of any aspect delineated herein, the antibody or antigen-binding fragment thereof has a heavy chain sequence

```
                                           (SEQ ID NO: 11)
QVQLVESGGGVVQPGRSLRLSCAASGFTFSSSAMHWVRQAPGKGLE

WVAVIWSDGSNENYADSVKGRFTISRDNSKNTLYLQMSSLRAEDTA

VYYCATDKTYVSGYTSTWYYFNYWGQGTLVTVS
``` and a light chain sequence

```
                                           (SEQ ID NO: 12)
DIQMTQSPSTLSASVGDRVTITCRASQSIDNWLAWYQQKPGKAPKLL

IYTASRLESGVPSRFSGSGSGTEFTLTISSLQPDDFATYYCQHRTFGQG

TKVEIK
``` or the antibody has a heavy chain sequence (SEQ ID NO: 13)
QVQLVESGGGVVHPGRSLRLSCAASGFTFGTSIMHWVRQAPGKGMQ

WVAQISHDESRKFYSDSVKGRFTVSRDNSKNTLFLEMSSLRIEDTAVY

YCAKDLSPPYSYAWDIFQYWGQGSLVTVS and a light chain sequence (SEQ ID NO: 14)
DIVMTQSPESLAVSLGERATINCKSSQSVLYSSRSDNKDYLAWYQQK

PGQSPKLLIYWASTRESGVPERFTGSGSGTDFTLSISSLQAEDVAVYY

CQQYYSSPPTFGGGTKVELK.

In various embodiments of any aspect delineated herein, the antibody or antigen-binding fragment thereof inhibits binding of GP1 and a transferrin receptor 1 (TfR1). In various embodiments of any aspect delineated herein, the antibody or antigen-binding fragment thereof binds a TfR1 receptor binding site of GP1. In various embodiments of any aspect delineated herein, the TfR1 receptor binding site includes amino acids 87-235 of JUNV GP1 or the corresponding amino acids of an arenavirus GP1 (see e.g., FIG. 8A). In various embodiments of any aspect delineated herein, the TfR1 receptor binding site includes one or more of amino acids Serine 111, Aspartate 113, Isoleucine 115, and Lysine 216, amino acids 113-124 (JUNV GP1 loop 3), and amino acids 166-174 (JUNV GP1 loop 3) of JUNV GP1. In various embodiments of any aspect delineated herein, the antibody or antigen-binding fragment thereof the TfR1 receptor binding site interacts with Tyr211 of TfR1. In various embodiments of any aspect delineated herein, the antibody or antigen-binding fragment thereof, has a Tyr in CDR H3 that forms a corresponding interaction with GP1 as Tyr211 of TfR1. In various embodiments of any aspect delineated herein, the antibody or antigen-binding fragment thereof has neutralizing activity in the subject. In certain embodiments, the antibody is one or more of CR1-07, CR1-28, and GD01.

In various embodiments of any aspect delineated herein, the arenavirus is a mammarenavirus or New World arenavirus. In various embodiments, the New World arenavirus is one or more of Junin (JUNV), Machupo (MACV), Guanarito (GTOV), Sabia (SBAV), Chapare virus (CHPV), Tacaribe virus (TCRV), or White Water Arroyo virus (WWAV).

In various embodiments of any aspect delineated herein, the isolated antibody or antigen-binding fragment thereof is administered to a subject. In various embodiments, the subject is human. In various embodiments of any aspect delineated herein, the subject is infected or at risk of infection with a New World arenavirus (e.g., Junin (JUNV), Machupo (MACV), Guanarito (GTOV), Sabia (SBAV), Chapare virus (CHPV), Tacaribe virus (TCRV), or White Water Arroyo virus (WWAV)). In various embodiments of any aspect delineated herein, the subject has or is at risk of having viral hemorrhagic fever.

In various embodiments of any aspect delineated herein, the method is in vivo or in vitro. In various embodiments of any aspect delineated herein, the method is performed in a subject (e.g., a subject in need thereof). In various embodiments of any aspect delineated herein, the arenavirus or arenavirus infection is neutralized in the subject. In various embodiments of any aspect delineated herein, the antibody or antigen-binding fragment thereof is administered as plasma or serum. In various embodiments of any aspect delineated herein, the antibody or antigen-binding fragment thereof is obtained from blood, plasma, or serum (e.g., from a survivor of an arenavirus infection).

In various embodiments of any aspect delineated herein, the first and second species of New World arenavirus are different species. In various embodiments of any aspect delineated herein, the first arenavirus is naturally occurring or genetically engineered to have enhanced virulence. In various embodiments of any aspect delineated herein, the first species of New World arenavirus is Junin (JUNV), Machupo (MACV), Guanarito (GTOV), Sabia (SBAV), Chapare virus (CHPV), Tacaribe virus (TCRV), or White Water Arroyo virus (WWAV). In various embodiments of any aspect delineated herein, the second species of New World arenavirus is Junin (JUNV), Machupo (MACV), Guanarito (GTOV), Sabia (SBAV), Chapare virus (CHPV), Tacaribe virus (TCRV), or White Water Arroyo virus (WWAV).

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "arenavirus glycoprotein 1 polypeptide (GP1)" is meant a polypeptide or fragment thereof having at least about 85% or greater amino acid identity to one or more of the amino acid sequences provided at GenBank accession nos. EU260463 (CHPV 810419), NC_005077 (GTOV strain INH 95551), D10072 (JUNV MC2), NC_005078 (MACV Carvallo), NC_006317 (SABV SPH114202), NC_004HEK293 (TRVL 11573), or AF228063 (WWAV 9310135) and having arenavirus GP1 biological activity. Exemplary arenavirus GP1 biological activities include binding to transferrin receptor 1, arenavirus cell attachment, arenavirus cell entry, and/or arenavirus infectivity. In various embodiments, the GP1 polypeptide comprises a GP1-receptor binding site comprising residues 87-235 (JUNV numbering; see also alignments in FIG. 8A). An exemplary arenavirus GP1 polypeptide sequence for Junin virus (JUNV) is provided below:

(SEQ ID NO: 15)
1 dlpllctlnk shlyikggna sfkisfddia vllpeydvii qhpadmswcs ksddqiwlsq 61 wfmnavghdw yldppflcrn rtktegfifq vntsktgine nyakkfktgm hhlyreypds 121 cldgklclmk aqptswplqc p By "arenavirus GP1 polynucleotide" is meant a polynucleotide encoding an arenavirus GP1 polypeptide. An exemplary arenavirus polynucleotide sequence for Junin virus is provided at GenBank Accession No. D10072, which is provided below.

(SEQ ID NO: 16)

```
   1 tgcagtaagg ggatcctagg cgattttggt aacgctataa gttgttactg ctttctattt
  61 ggacaacatc aaaccatcta ttgtacaatg gggcaattca tcagcttcat gcaagaaata
 121 cctacctttt tgcaggaagc tctgaatatt gctcttgttg cagtcagtct cattgccatc
 181 attaagggtg tagtaaacct gtacaaaagt ggtttgttcc aattctttgt attcctagca
 241 ctcgcaggaa gatcctgcac agaagaagct tttaaaatcg gactgcacac agagttccag
 301 actgtgtcct tctcaatggt gggtctcttt tccaacaatc cacatgacct gcctctgttg
 361 tgtaccttaa acaagagcca tctttacatt aaggggggca atgcttcatt caagatcagc
 421 tttgatgaca tcgcagtgtt gttaccagaa tatgacgtta taattcagca tccggcagat
 481 atgagctggt gttctaaaag tgatgatcaa atttggctgt ctcagtggtt catgaatgct
 541 gtggggcatg attggtatct agacccacca tttctgtgta ggaaccgtac aaagacagaa
 601 ggcttcatct ttcaagtcaa tacctccaag actggtatca atgaaaacta tgccaagaag
 661 tttaagactg gtatgcacca tttatataga gatacccccg actcttgctt ggatggcaaa
 721 ctgtgtttga tgaaggcaca acccaccagt tggcctctcc aatgtccact tgaccatgtc
 781 aacacattac atttcctcac aagaggcaag aacattcagc ttccaaggag gtctttaaaa
 841 gcattctttt cctggtctct gacagactca tccggcaagg acaccctgg aggctattgt
 901 ctagaagagt ggatgctcgt tgcagccaaa atgaagtgtt ttggcaatac tgctgtagca
 961 aaatgcaatc tgaatcatga ctctgaattc tgtgacatgc tgaggctttt tgattacaac
1021 aaaaatgcta tcaaaacctt aaatgatgaa actaagaaac aagtaaatct gatgggacag
1081 acaatcaatg cgctgatatc tgacaattta ttgataaaaa acaaaattag ggaattgatg
1141 agtgtcccct actgcaatta cacaaaattt tggtatgtca accacacact ttcaggacaa
1201 cactcattac caaggtgctg gttaataaaa acaacagct atttgaacat ttctgacttc
1261 cgtaatgact ggatactaga aagtgacttc ttaatttctg aaatgctaag caaagagtat
1321 tcggacaggc agggcaaaac tcccttgact ttagttgaca tctgttttg gagcacagta
1381 ttcttcacag cgtccctctt ccttcacttg gtgggcatac ccacccatag gcacatcaga
1441 ggcgaggcat gccctctgcc ccacaggcta aatagcttgg gtggttgcag atgtggtaag
1501 taccccaatc taaagaaacc aacagtttgg cgcagaggac actaagacct cccgaaggtc
1561 cccaccagcc cgggcattgc ccgggctggt gtggcccccc agtccgcggc ctggccgcgg
1621 actggggagg cactgcttac agtgcatagg ctgccttcgg gaggaacagc aagctcggtg
1681 gtaatagagg tgtaagttct tcttcataga gcttcccatc caacactgac tgaaacatta
1741 tgcagtctag cagagcacag tgtggctcac tggaggccaa cttaaaggga gcatccttat
1801 ctctcttttt cttgctgaca accactccat tgtgatgttt gcataggtgg ccaaatttct
1861 cccagacctg ttggtcgaac tgcctggctt gttctgatgt aagcctaaca tcaaccagct
1921 taagatctct tcttccatgg aggtcaaaca acttcctgat gtcatcggac ccttgagtgg
1981 tcacaaccat gtccggaggc agcaagccaa tcacgtaact aagaactcct ggcattgcat
2041 cttctatgtc tttcattaag atgccgtgag agtgtctgct accattttta aacccttcct
2101 catcatgtgt ttttctgaag cagtgaatat acttgctacc tgcaggctgg aacaacgcca
2161 tctcaacagg gtcagtagct ggtccttcaa tgtcgagcca aagggtattg gtggggtcga
```

```
2221 gtttccccac tgcctctctg atgacagctt cttgtatctc tgtcaagtta gccaatctca
2281 aattctgacc gttcttttcc ggttgtctag gtccagcaac tggtttcctt gtcagatcaa
2341 tacttgtgtt gtcccatgac ctgcctatga tttgtgatct ggaaccaata taaggccaac
2401 catcgccaga aaggcaaagt ttgtacagaa ggttttcata agggtttcta ttgcctggtt
2461 tctcatcaat aaacatgcct tctcttcgtt taacctgaat ggttgatttt atgagggaag
2521 aaaagttatc tggggtgact ctgattgtct ccaacatatt tccatcatca agaatggatg
2581 caccagcctt tactgcagct gaaagactaa agttgtagcc agaaatgttg atggagcttt
2641 catccttagt cacaatctgg aggcagtcat gttcctgagt caatctgtca aggtcactca
2701 agtttggata cttcacagtg tatagaagcc aagagaggt taaagcctgt atgacactgt
2761 tcattgtctc acctccttga acagtcatgc atgcaattgt caatgcagga acagaaccaa
2821 actgattgtt aagttttgaa ggatctttaa catcccatac cctcaccaca ccatttcccc
2881 cagttccttg ctgttgaaat cccagtgttc tcaatatctc tgatctcttg gccagttgtg
2941 actgagacaa gttacccatg taaaccctt gagagcctgt ctctgctctt ctaaacttgg
3001 tttttaaatt cccaaggcca gacgccaact ccatccgctc aaccctcccc agatctcccg
3061 ccttgaaaac cgtgtttcgt tgaacactcc tcatggacat gagtctgtca acctctttat
3121 tcaggtccct caacttattg aggtcttctt ccccccttttt agtctttctg agtgccgct
3181 gcacctgtgc cacttggttg aagtcaatgc tgtcagcaat tagcttggca tccttcagaa
3241 catccgactt gacagtctga gtaaattgac tcaaacctct ccttaaggac tgagtccatc
3301 taaagcttgg aacctctttg gagtgtgcca tgccagaaga tctggtggtt ttgatctgag
3361 aaaaaattgc tcagtgaaag tgttagacac tatgcctagg atccactgtg cg
```

By "transferrin receptor 1 polypeptide (TfR1)" is meant a polypeptide or fragment thereof having at least about 85% or greater amino acid identity to the amino acid sequence provided at GenBank Accession No. AF187320 and having arenavirus GP1 binding activity. An exemplary human TfR1 polypeptide sequence is provided below:

(SEQ ID NO: 17)
MMDQARSAFSNLFGGEPLSYTRFSLARQVDGDNSHVEMKLAVDEEENAD

NNTKANVTKPKRCSGSICYGTIAVIVFFLIGFMIGYLGYCKGVEPKTEC

ERLAGTESPVREEPGEDFPAARRLYWDDLKRKLSEKLDSTDFTGTIKLL

NENSYVPREAGSQKDENLALYVENQFREFKLSKVWRDQHFVKIQVKDSA

QNSVIIVDKNGRLVYLVENPGGYVAYSKAATVTGKLVHANFGTKKDFED

LYTPVNGSIVIVRAGKITFAEKVANAESLNAIGVLIYMDQTKFPIVNAE

LSFFGHAHLGTGDPYTPGFPSFNHTQFPPSRSSGLPNIPVQTISRAAAE

KLFGNMEGDCPSDWKTDSTCRMVTSESKNVKLTVSNVLKEIKILNIFGV

IKGFVEPDHYVVVGAQRDAWGPGAAKSGVGTALLLKLAQMFSDMVLKDG

FQPSRSIIFASWSAGDFGSVGATEWLEGYLSSLHLKAFTYINLDKAVLG

TSNFKVSASPLLYTLIEKTMQNVKHPVTGQFLYQDSNWASKVEKLTLDN

AAFPFLAYSGIPAVSFCFCEDTDYPYLGTTMDTYKELIERIPELNKVAR

AAAEVAGQFVIKLTHDVELNLDYERYNSQLLSFVRDLNQYRADIKEMGL

SLQWLYSARGDFFRATSRLTTDFGNAEKTDRFVMKKLNDRVMRVEYHFL

SPYVSPKESPFRHVFWGSGSHTLPALLENLKLRKQNNGAFNETLFRNQL

ALATWTIQGAANALSGDVWDIDNEF

By "TfR1 polynucleotide" is meant a polynucleotide encoding a TfR1 polypeptide. An exemplary human TfR1 polynucleotide sequence is provided at GenBank Accession No. AF187320, which is provided below.

(SEQ ID NO: 18)
```
  1 ccggttaggg gccgccatcc cctcagagcg tcgggatatc gggtggcggc tcgggacgga
 61 ggacgcgcta gtgtgagtgc gggcttctag aactacaccg accctcgtgt cctcccttca
121 tcctgcgggg ctggctggag cggccgctcc ggtgctgtcc agcagccata gggagccgca
181 cggggagcgg gaaagcggtc gcggcccag gcggggcggc cgggatggag cggggccgcg
241 agcctgtggg gaaggggctg tggcggcgcc tcgagcggct gcaggtacac ggggtcggcg
301 gctgtgcgca gaggcgtccc tgcgcctctc gtcccttcgc ctctcgtccc ttcccttctc
```

-continued

```
 361 tctgccttct tgcccgcctc ctcggtcaca gagcgacgaa tgacgagacc aggtgtaccc
 421 cactgtcgct ctcagccccg gggacttcgg gtcctcgccc ttgaaggccg caggccctag
 481 tgcgccggct ccgggctgcg ggtccgggag cgcgggcgca gccaaggtgc agctgcgcgg
 541 cgtgcggcgc cgggggaaca cgtggctgct ccaggaagtc gccccaggga acggctggga
 601 ttcgtgggtg accttgggct cctaaacctt cggttccccg gctccgggc gggccccgtt
 661 ctcactgcgg aaagggacaa agctgtcccc gattcggtta ctagcgtgtt acaggcatta
 721 attagatacg ggtttctgta aacttaccct tcggctctgg tacaacctga tcttgccatg
 781 ctctgcctgt tcgccttgtg tatggattct gttttctcaa ggcagaatcc gactgaacgc
 841 cgcaggtgtt cacattaaga atattgctag cagttctcac tacaagacgg gagccatagg
 901 agtgacttat ttgtgaaaga tacttggaga ttagcggtgt ggtcagaggg ctgtgctgga
 961 ttgatgggcg ccggagaggc cgattgtgtc acattctgct ggacagttct tttaaggttg
1021 ggagggtggg taagaaaata cattctgatt cggctctttt cggataacgc tttccctctg
1081 cttactgctt gtaagacctc acttacccgg gggactggat tctgcagctt tttccatttt
1141 cttccccgtt gataagagga ttaaagttag gaaattgtat ttggctaccc catgcttata
1201 tgctaagctt actgtgaaaa ttaaggttag gctgtctaga gtacttgtgg accctgctgg
1261 ttccccccgc ccccggccc tgaattttgg gttacaatat gcttctcaag aaaactcaga
1321 gttaagataa ttttttgtcat cgatttttgca aggttatata tagcatagca tccttcaatt
1381 tcctttggat gttcttatca agtaatggtg gctgtaaacc tagcctgtgt tgaagattgt
1441 tagatagaca gcagtttggc taactccgcc ctaaggcgag gcagttactt gcctctgata
1501 atgtattaa atgtcatgga gcaagattcc cagctaaacc tgaatcgatc acaatgctag
1561 ttaaaaatga ccctcggctg ggcgcattgg ctcccgcctg taatcccagc actttgggag
1621 gccaaggcag gcggatcacc taaggtcagg agttcgagtc cagtctgact aacatggtga
1681 aatcctgtct ctactaaaaa cacaaaaatt agccgggcat ggtggctcac gtctgtaatt
1741 ccagcacttt gggaggccga ggcaggtgga tcacttgtgg tgaggagttc gagactagcc
1801 tggccaacat ggtgaaaccc cgtctctacg aaaaatacaa aaattagctg gcatggtggg
1861 tgcacacctg taatcccagc cactcaggag gctgaggctc gaaagtcgct ttaacctggg
1921 aggcagaggt tgtagtgagc tgagatcgtg ctactgcact ccagcctgcg cgacagcgag
1981 atgccatctc aaaaacaaca acaaaaaaac tccctactaa accagaagat gatggggacg
2041 ggaaaagatc ctggtccaat gttttcatta tattttcat atcatttgga atctcatgca
2101 tcaggcatgc cccagtactg ttaaagacaa tattttact cattatcagg tagttcaata
2161 ccagttatta caggataggg aagtcagtca gagaaggctt catagagatg aagccttgag
2221 ctgagcctgg aagaaatgag gaggacctca aggaacagag aagaatgttg gtgggtaaaa
2281 acaggggctg gattctgtct gattttggag aaaatagagg gtagtgaagt tgttaggcag
2341 tgaatgtgtt ccatttcatg gttcaaaacg tggggctacg ttttgcctac ctgagcttca
2401 ttattaatgt gagaaattga attgttgttt tcagtcacca ttgagaacac caaagataac
2461 acaagtagct tagattatta tttatttatt tattttttgac agatttcaca cttgttgccc
2521 aggctgtagt gcaatggtgt gatctcggct ccctgcaacc tccacctccc ccaggttcaa
2581 gtgattctcc tgcctcagcc tccccagtag ctgggattac aggcatgcgc caccatgccc
2641 ggctaatttt gtatttttttt ggtagagatg ggatttctcc atgtttggtc aggctagtct
2701 caaactctca acctcaggtg atctgctcgc ctcggcctcc caaagtgttg ctgggattac
```

-continued

```
2761 aggcgtgagc caccatgccc ggccatcgct ttgtgttctt aaaattaatt taaaacaaga
2821 aaacttgagg aatgatggtt cagatgagtg ttaaaacttg caagatgttt tttcctagaa
2881 aaggatgatt aaaattggtt cagggtgggg ccttccagtt ctggctctaa tgattgggtc
2941 cttactgttc tggtggagtg gtagtgataa gcttttttgta acagaagggg caaaagattg
3001 tgcttctggc tgggcgcagt ggctcacgcc ttcgatttcc ttgggatgtt cttatcaagt
3061 aactaatctt agcactttgg gaggccaggt gggtggatca ccctaggtca gaagttccag
3121 accagcctgg ccaacgtggt aaaatcccgt ctctactaaa aatacaaaaa ttagctgggc
3181 atggtggtgg gcacctgtaa tcccagctac tcggagtctg aggtgggaaa atggcttgaa
3241 cccgggaggg ggaggttgca gtgagccgag atcctgccat tgcactccag cctaggcaac
3301 aagaccgaaa ctctgtctca agaaaaaaaa aaagattatg cttctaagaa tatggtctat
3361 tgcatatgga cactggtttt taaagcttga atttaaaaag aattttttgt aataggtttt
3421 agagcttttt ctttttcttt tttattattt ttttgagatg gagtctcact ctgtcaccca
3481 ggctggagtg cagtggtgcc atctcggctc actgcaacct ccacctcccg ggttcaagcg
3541 attctcctgc ctcagcctcc ccagtagctg ggattacagg tgcccaccac cacgcccatc
3601 taattttgt attttagta gagatggggt ttcaccacct ggccaggct ggtctcaaac
3661 tcctgacctc gtgatccacc tgcctcggct cccaaagtca gtgttgggat tacaggcatg
3721 agccaccgtg cctggccaga aagcttttc ttaatgccag ttataatacc ctttgcttta
3781 caatttgcgt atacctcaca gcttgctttg tgccgtgtgt gtttaatatg ccctaagtgt
3841 actcgtatat aggaaaagct ttaaaatggt atccaataaa tgtccatttt gcaaatctca
3901 ggataatgtc attttcaagt atctagatgc cctcaaacca aattaactgg aaaattcaga
3961 tttcagttaa ggcctttaac ttaacttagg actttgatta cagagatgta ttttgctttg
4021 acaaaagtta aggttaatgt cttaaatttc cagagatgat aacacagttt ctataaccca
4081 gtaacccatt taacttcgct tagattatca attttcagcc ttgaacaggc cacttagttt
4141 ctctaataac tggcctcttc atctgtaaaa cagcgtaatc tgtgtttcat gtttcttctt
4201 gtgtcaaaga tcgaatcact tgtaggaact attcattcag tcaggatcag tatttcttcc
4261 ccttcccatt ggagatggtt tgtggtattt gtagcataac tggtcttgtc tgccttagtc
4321 ttaattttgt ctttttgtat gtgtcacttt ctttttttt tgagacagag ttttgctctt
4381 gttttccagg ctggagtgca gtggcgcgat cttggctcac tgcaagctcc acctcctggg
4441 ttcacgccat tctcctgcct caggctcccg agtggctggg attacaggcg cccaccacca
4501 cgtccggcta atttttgtat ttttagtaga cagggtttt ccatgttg gccaggctgg
4561 tcttgaactc ctgacctcag gtgatccacc catctcagcc tcccaaagtg ctaggattac
4621 aggtgtgagc caccccgccc agcagtatgt gtcattttgt ctactcagaa catagtggtt
4681 cgtacttata attgcagcac tttgggaggc caaggtggga ggattgtttg aggccaggag
4741 ttcaagacca gcctgggcaa catagggtga ccttgtctct acaaaaagaa aaaaaagaa
4801 ttatgtatat aacaaacttt aaaaaggatc ccacttaatt tagttgtcat gtaaactatg
4861 gttaaatacc ttttctagaa aagtgataat gtattttaaa aatttaatgt atcatttagc
4921 ctggtaatag aaagctcact aatctgatac agtagtatct ttttcaataa ttctctattc
4981 tgatacctga ggttcttctg tgtggcagtt cagaatgatg gatcaagcta gatcagcatt
5041 ctctaacttg gtaagatatt tcagttgtat ttctgtgtct gcaagaatgt gaaatataca
5101 agcatgactt taactgagta agcatgaaat aataaccca atctattatc aggtattcat
5161 ttacatttga ttggtagtct tgaggcataa ctgatctcac aaagagttca gccttcagta
```

-continued

```
5221 gggttaatta tggaaagtct tggaagaatt ctcagagtgg ttctgggtgt ggtagacggg 5281 gacagcttag tagataagac gaattaaagc cctgatcaaa atgttttagt aggagaagta 5341 aaaagcaaag gcttgcgggg cgctgtggct cacgcctgta atcccagcac tttgggaggc 5401 tgaggtgggt ggatcacctg tggtcaggag ttcaagacca gcctgaccaa catggtgaaa 5461 ctcggtctct actaaaaata caaaaaaaaa aaaattagct gagtgtcatg gcgcatgcct 5521 gtagtcccag ctacttggga ggctgaggca ggagaattgc ttgaacccgg gaggcggagg 5581 ttgcaatgag ctgagatcac gccattgcac tccagcctgg gcaacagagt gagactccgt 5641 ctcaaaaaaa aaaaagcaa aggctgaatg aggccaagtg tggtggctca ctcccgcaat 5701 cccagcagtt tgggaggtga ggcaggagga tcacttgagg agtttgagac ttgcctgggc 5761 aacatagcaa gcccatctct attaaaaaaa aatgaaattt taagaaacat tgagtagaca 5821 gtatgagtga aagctgaaag aacatacaaa aaaaacagcc atccaggcca tgacgagaag 5881 gagcctaact cttaacactc tgtctagacc tcaattctct cttatttgta tttatttatt 5941 tatttatttt tatttttattt tttgagatgg agtctcagcc tgggctctgt tgcccaggct 6001 ggaatgcagt gtgcaatctt agctcactgt aacctccgcc tcccgagttc aagcgatttt 6061 cctgcctcag cctcctgggt ggctgagatt acaggcgtgc gacaccaagc ccagctagtg 6121 gtttttttt ttgaaatttt agtgagaggg gatttcacca tgttggtcag gcttgtctca 6181 aacttctgac cataaatgat ctgtgtgcct cggcccccc ccagagtgct gggattacag 6241 gcatgagcca ctgtgtctgg tctattctct cttttctgtc ttctatctta tgcttagtca 6301 gaatttctgc ttatttataa ctttgtttta ttcttgctcc cttgctccca ccaacatcat 6361 ggtctgggtt actgcatagt atcctgaact gatttgtgcc cctagtccca gctactcagg 6421 aggctgaggt gggggaatca gtagagccca ggattttgag gctgcagtga gctgtgatca 6481 caccactgta ctccatcctg ggagagagag ggagaccttg tctcaaaaaa aaaaaaaatt 6541 tacaaaaagg gagagactga ctgagaagac cagtgtgaac tagcccttga ctgggcccag 6601 ggaagaatgt tggtttgaaa ggagaacacc ctaaggaata tatagcaagt tatagtaatg 6661 gcccaataac aagcatatac ctaaacgagc ttttcctaaa cattcccgtg cctgttcttc 6721 atcatgcctt tttccgcaac acagtttggt ggagaaccat tgtcatatac ccggttcagc 6781 ctggctcggc aagtagatgg cgataacagt catgtggaga tgaaacttgc tgtagatgaa 6841 gaagaaaatg ctgacaataa cacaaaggcc aatgtcacaa aaccaaaaag gtgtagtgga 6901 agtatctgct atgggactat tgctgtgatc gtcttttct tgattggtga gaatgaccat 6961 tccaaacttc aatgttttct ataaccaact ctgggaagtc tgttatgtca gctcagcata 7021 tagttatttt gtacctttttt tttttttttt ttttggaga cagaggctta ctctcttgcc 7081 taggctagag tgcagtggca ccatgttggc tcactgcaac ctcagcctcc caggtttaag 7141 cgattctctg ccttagcctc ctgagtagct gggactatag gcgcccacga ccacacctgg 7201 ctaatttttt ttttttttttt tgagttggag tctcactctg tggctcaggc tggagtgcag 7261 tggcgtgatt tcggctcact gcaatctccg cctcccaggt tcaagcgatt cttctgcctc 7321 agcctcctga ggagctggga ctacaggcgt gcaccaccac acctggctaa ttttttgtatt 7381 tttagtagag acggggtttc accatgttgg tcaggctggt ctctaactcc tgacctcgtg 7441 atctgcccgc ctcagcctcc cagagtgctg ggattacagg catgagccac tttcccgtcc 7501 actttatgcc ttttaagtg ccactaggaa gacaatcatg agtagattct atacctgtca 7561 ttgaatttaa tctggttgga aagagagacc catgaattat ttcaatacga cgtgcaagtg
```

-continued

```
7621 ttttcttttt atttatgtat ttttttgttt gctcccactc caccaggaag caaatgctac
7681 gctagaaaat atccgcagga cactggcggt gcagcagctc agtctcatgt ttcaaggggg
7741 tcttttggaa aaaactacct atgttttgaa taggtagcta tttgaaataa agctagtata
7801 taatttatta agtggtttaa agtatacaaa actgagatgc attatatact ttaaaactac
7861 ttagaatttg atgaaaacca gtattttcaa ggcttacctg aaaatattaa cagattaaca
7921 gggatagatt acaaatgaaa ttctgagttc agctctggaa ctttgtctct ttaggattta
7981 tgattggcta cttgggctat tgtaaagggg tagaaccaaa aactgagtgt gagagactgg
8041 caggaaccga gtctccagtg agggaggagc caggagagga cttccctgca gcacgtcgct
8101 tatattggga tgacctgaag agaaagttgt cggagaaact ggacagcaca gacttcaccg
8161 gcaccatcaa gtgagtgcca gctgctgtgc aagtatctag acaagtaatt caagaattat
8221 gataggccac ggggaaacaa taatggtgac actgtgggga atggcttgtt agagaagaca
8281 agacttgtca tgtttagcta aagaggggaa ggggcctgta aaaaactgaa actatactgg
8341 taggggaaaa ggtagaactt ctctggggag tctccttttt cttaaaaaat taataggccc
8401 ttgatgtttt ccccatcttt gtagcttatt gcttgctgtc attctctggc tctgattttt
8461 cttcttaacc tcttgtaacg ttgtactaag ctctgctttg ctgacaagga catcagtagc
8521 ttttctctgt tttaggaagc aacacatgcc agaagtagcc ttttcatct ccttgatcat
8581 gggtaactgc ctgccttaag tctctagtgc ttcttaattt ctgtgatact cacccattaa
8641 ccctaggcc agtcagtatc cagagacaat gtctccctct ggtggaggct ggaatacggt
8701 ggcgtgctct catctcaccg cagcttcatc cccctaccat agcctcctga gtagctggga
8761 ctataagcac gcagcaccac acccagctaa tttttttttt ttttttttaag agatggagtc
8821 tcaccatgtc tcccaggccg gtctgttctt agattttat ttatttactt atttattttg
8881 agatggagtc ttacgtgttg cccaggctgg agtgcagtgg cacgatttca gctcagtgca
8941 acctctgtct cccaggttta agcaattctc ctacctcagt ctcctgagta gctgagatca
9001 caggcttgta ccaccatgct ctgctaattt ttgtgggttt tttttttgtt tgtttgtttt
9061 tttttttttgc agaaacggga tttcaccatg ttggccaggc tggtgtctaa ctcctgacct
9121 cagatgatcc tcctgtcttg gctcccaaag tgctgggaat taacaggatg gaggcactgc
9181 acctggccaa aatttctaat tttatattta tttatttatt taatttgta atgggctttt
9241 ctggcaaaaa ctagaaagca tgctagacaa attctaaaag agctgtaaca cttgtccata
9301 gagttttact atctttgcac atacatgcct ctgtgcaaag aataaattta tcttttcctt
9361 tttgcaagct tcctacactt acagtggtac tataattctt tagtcttaag ttatggcatt
9421 ttctacttca tctagttgat gcttttgtgt ttatttactg tacaccagac cttatggtta
9481 aagtgagagt atagtccacc ccacaaaaat gtaagaacta atatgctgag taaatagaaa
9541 gaagtatggg agatcggacc aaggagcagt tctgcttcag ggtattcaga tgcttcacaa
9601 gtaggtgaga attgaaacta tgcactctgt tcagcacagt attactatct tagatttat
9661 agtagatctg gaagctactc atttccccta aaactatcct aagcagatac attgtgttat
9721 gatgaggctc ttgaaggagt gctttgtagt gggtaaagaa gctttgaagt tacaagattt
9781 ggggcaaaat tttttttctt ttgtgatatt ctggtcagtc tagaagtttt gggtcacagt
9841 tcatttatct gaactatgag ggataatatt ttgctttcaa acaatttgt ttaatccttg
9901 acttaaatgt ttattttaaa gtaaacttaa gttcatttaa aaggcatttt ctcctccagg
9961 ctgctgaatg aaaattcata tgtccctcgt gaggctggat ctcaaaaaga tgaaaatctt
10021 gcgttgtatg ttgaaaatca atttcgtgaa tttaaactca gcaaagtctg gcgtgatcaa
```

```
10081  cattttgtta agattcaggt caaagacagg tatgttgaaa gatggtaaac ttattttat 10141  acaagtagct attttcaggt gtgctaaata tagcaaagac ttttgttag tgttgttggc 10201  ttttttttga aatggagtct cgctctgttg cccaggctgg agtgcagtgg cacaatctct 10261  gctcactgca gcctttgcct tctgggttca agtgattctc ctgccttagc ctccagagca 10321  gctgggatta caggcgcacg ccaccacgcc cagctaattt ttgtattttt agtagaggtg 10381  ggatggtctc gaacttttga cctcaggtga tcagcccgcc tgggcctccc aaagtgctgg 10441  gattacaggc gtgagccacc gcatgcggcc caaaggcttt taaaataaaa atcaagctta 10501  agatttagag gtaaatttcc tcaagccaaa taatgcaaga catactaaat gtaagctatt 10561  gtgttttttg gaaggatgac cttaggctta ttttaactta atcttttaa cagcgctcaa 10621  aactcggtga tcatagttga taagaacggt agacttgttt acctggtgga gaatcctggg 10681  ggttatgtgg cgtatagtaa ggctgcaaca gttactgtaa gtaaggcaaa acagtgcatg 10741  agactcttcc ctattgaatc attcaaaact catcttttct gttcttagga gttataaatt 10801  tacctgtaaa atgtaaatga tcatgagata ttttggtttt caaccctcta atgacacagt 10861  caacatgcat tgtcttctct ctctaatcac tttccccatg tcctgtttta ttttttcttt 10921  atagtactgc tagcagctga cattatctat gcctttgttt ccattagaat gtgagccaga 10981  tgaagaatca tgggttagtt ctatttactg ccatgttgca gagctttgga gaatgcctga 11041  catacatagt agtatttgct aaacaaatgc atatcctccc tgtggggaca gatgtaaata 11101  tccatcttgg ctggggccta gtcttagctt gattcgttaa tgcttgatct ttttctattt 11161  ttgttttgag acagggtgtc actctgttgc cctagctgga gtgcagtggc gtgagcttgg 11221  ctcactgcat tctccaccac cacccaggct caagtgagcc tcttgagtag ctgagatgtc 11281  cagttaattt ttatttttta tttattatt attattatta ttattatt tattattatt 11341  tggtagagac agggttttgc catgttggcc aggctggtct tcaattgaaa ctcctgggct 11401  caggtgattc accaccctca gcctcccaaa gtgctgggat tacaggagga agctgcttcg 11461  cccagcccct gatctttta aatttaggca aatatagtca aattaacaca gaaatagaga 11521  acagatagat agaataattt tcagcttaaa aatcacattt gtggctgggc gtggtggctc 11581  acgcctgtaa tcccagcact tgggagtcc aaggtgggtg atcacctaa ggtcagagct 11641  accagcctgg ccaacatggt gaactctatt aaaaatacaa aaattagcca ggcgtggtgg 11701  tgggtgcctg taatcccagc tacttgggag gctggggcag gagaatcgct tgaagccagg 11761  aggtggaggt tgcagtgagc ggatattgcg ccattgcact ccagcctgag caacaaaagc 11821  gaaattccat ctcaaaaaaa aaaaaatcac atttgtaagt caggcgtatc tctagtggat 11881  accttttcggg gctggtgcag ttctgtgttg attccttgcc tttctggata cttgtgcttt 11941  atccctttgc ctggctgcct ataagccagg agtttagaga tgggtaggtt gttctgttaa 12001  agaacattga agattttgt tcaacttcaa gctttctgta ttgagggctt ggttgttagt 12061  gtcagtttat ggctgttcat ctggactctt atgagcttag gaacatcatg acacatctaa 12121  agttggtgta tgcaagtcac tttgttgtaa tagatggtgt tttaattttg ggacagattt 12181  attatcagac ctttcagtta aaacctattt ctatgatgtc ctcaaggcta agattgttcc 12241  aggcctccag tcccatgacc agcctacata ggcctctta atctaaatgc ccttcagatg 12301  aaaggcagca tgggataaaa gcatgaaaga cataggaggc caaaaatctt gatttattc 12361  caatagctct gacctaaaag ttgtaaagtt ttttagaact catgtctttt ttaggccttg 12421  gcctcctttt atctcttact tgggttgcct gtcttaggtt tgatctataa cactcttctg
```

```
12481 tctcaagatt ttagagctgt tccgatacca taatgctcat taaatctaat gtctttgttc 12541 tagggtaaac tggtccatgc taattttggt actaaaaaag atttttgagga tttatacact 12601 cctgtgaatg gatctatagt gattgtcaga gcagggaaaa tcacctttgc agaaaaggtg 12661 agtatgagtt attataatat taaatacagt acttttggta tcttactctt caggtaagtg 12721 atatttcttg ttaatattct tacattctga aaatcagcaa tcttaaactc tcataccaga 12781 taatataatt tattaaaatg ctcaacaaat gaagtaagtt ccacttacct aatcagaagt 12841 gcttaagttg aaagctattt ctctgtataa ctcagtttta cgcatataca gaattcagcc 12901 taaaaagcat gtttataaaa agggaaaatt aatagccaaa acatacacaa ggaactagag 12961 tggaacatat caaaagacag tggtgatttc tgcatttttta aaaaaagtgg cagggctcac 13021 acctgtaatc ccaacacttt aggaggctga ggtgggagga ctgcttgagc cctggaggtt 13081 gtgagatgtg actcgtgcca ctccagcctg agtgacagtg agactcaaaa aagtggttgt 13141 cttagatggg tttttgttat tttcctttttc tttttttttt tttttttgag acggagtctc 13201 ttgtcaccct ggctggagtg cagtggcgtg atctcagctc actgcaacct ccgcctccca 13261 ggttcaagtg atgctcctgc ctcagccttc tgagtagctg ggattacagg tgcccaccac 13321 caccatgcct ggctaatttt tgcatttttta gtagagacag ggtttcacga cgttggcctg 13381 gctggtcttg aactcctgac gtcaggtgat ccacctgcct tggcctccca gattgctggg 13441 attacaggtg tgagccacca ctcctggcct tgttattct tttttttttt tttttttttt 13501 gagagggagt tttgctcttt tgtccaggct ggagtgcagt ggcgcaattt tggctcactg 13561 caacctctgc cttatggttt caagcgattc tcctgcctca gcttcccaaa tagctgggaa 13621 tacaggcgcc agccactgcg cccagttaat ttttgtattt ttagtagaga cagggtttca 13681 ccatgttggc caggctggtc tcgaactcct gagcttgtga tcccctgcc tcagccttgc 13741 aaggtgttgg gattacaggc gtgagccacc actcctggcc cgttactctt attttgcaaa 13801 caagtgagtt aattttttcag gaagcaatta ataaattacc agataaacaa tttgaaatat 13861 ttggaagtat tataagttta gtcctctgta accatttggc ctttagcata atgtccagga 13921 tgtattctca tttcgtatga tcagatcttc attttctgag ctttatatgt tttcttttag 13981 gttgcaaatg ctgaaagctt aaatgcaatt ggtgtgttga tatacatgga ccagactaaa 14041 tttcccattg ttaacgcaga actttcattc tttggacatg tgagttattt cttgagtaaa 14101 tcaccgtttt gagttccttg agttgttctt ggattcctgt attagcagaa atagcactgt 14161 gtcttcctta actgctcttt tttctgggag ggcgttagca gtaagcaaga agatagatta 14221 cattgacttt gaggctttat tatttgttgc taaaagtact ttgtcaatag tgccttgaat 14281 ttgagaattt ccatatgcca tgaaaacagg agtcacattg tagagccact cagattttttg 14341 aggcttcaag ttggtaaact aaggttgggc tgcagcctta taccaaacct gaatcttaca 14401 gagaagtttt gaggaagtat gtgatggagt gaattgctct tttgttttcc taggctcatc 14461 tggggacagg tgacccttac acacctggat tcccttcctt caatcacact cagtttccac 14521 catctcggtc atcaggattg cctaatatac ctgtccagac aatctccaga gctgctgcag 14581 aaaagctgtt tgggtaagtt tttatttgaa agcggtcttg catagtgagg ttttatgatt 14641 agggaagaac ggtaatatgt tgattaaaat gttaaacatg atgataattt tccacatttg 14701 ggaattttgga ggatggttag ctgttacctt ggtacagata taaatgaatt tttctctata 14761 aagagatctt aataatggac tttggactta taaacacagg agaataagga gacttataaa 14821 cccagtgaat tccttgtgca agattcctgg catagcttct gctcaagtac ttctgtgctg 14881 aagcacgatg cctatagcag cccattcagt tagtagagag aatctgttag aattcatatt
```

-continued

```
14941 gggataaaat cctattcccc gaaacatcca tttgtctgga ttttcttct aagcaatacg
15001 gtatgattcc agttaccttg tctatagatt gagaagcctt gcttcttatg atggtttcca
15061 gagaaaccat ttatggttgt ggctcgctcc tctggatatc ctccctgtaa cgttagtgtc
15121 tctctttaaa aacagagccc agttccatta gagtacgtag cattaattt gatttggatg
15181 tggacatatt tatcatttcc tgttattaca ggatggagat ctagtttcag gcctttatga
15241 aagcatttat ctcctgtatg acataggttc tctgatcctg tttctttaac ataattggat
15301 agtgaaaata tattctactt gatagtctca aatgaagaac atctgtatat aaggagtata
15361 tgaaatacca tgactgttga tcatgctgag aggcctttag cataggggag tgtgtaacat
15421 accatgacta ttgataacgc taagaggcat ttagcatagg tgattttttt gactcattct
15481 acctaccacc tacaaatcgt aaccaacctg tgaagccagc gtcccatctt atccttatgt
15541 agtaggggag taataatgtt tcaacctata tttatgtaag taagccgcct taggagcagc
15601 tattatttgg gtaacacaga ggaattagat aggggaagca caagattttt tttttatttt
15661 gacagtctca ctctgttgcc caggcaggag tgcagtggca tgatcctggc tcactgcaac
15721 ctccacctcc tgggttcaag gaattctgcc tcggccttcc aaagtgctgg gattacaggc
15781 gtgagccacc gcacccagct gaggaatatt ttttataact gagctaagaa tgtgtactat
15841 ccttgttagt ggtgacagtt gggaaacata aaagtgtatt aatattcttt tatatattag
15901 aagaacttca ttttgagtcc atcttggtat gtattccaaa tataaactac gtaagtatgt
15961 ctggcagaaa ggcatagtta gagaagtgtt ttaaaatatt gcttaattaa tggtttccaa
16021 ttggctgcct gcagatcaaa gtaagacgca aatggttcac cactagagag taagttttt
16081 tttgttttta ttttgttttg ttttgttttg ttttttttg agacaggact tgtgctctgt
16141 tgcccaggct ggagtgcagt ggcgtgatct cggctcactg cagcctccgc ctcccaggtt
16201 caagcgattc tcctcctcat cctccttagt agctgggatt acaggcgcat gccaccatgc
16261 ccagttaatt tttgtatttt tagtagagtc ggggtttcac catgtcggtc aggctggtct
16321 tgaactcctg accttgtgat ccacctgcct cagcctccca aagtgctggg attacagggg
16381 tgagccactt cgccgggctg agagtaagtt tgtttatat gtcctcttaa tctgtaactt
16441 cactggacag gagtaaaccc tgggcaagga acaataactc agaacttacg cctgctttct
16501 gattctagga atatggaagg agactgtccc tctgactgga aaacagactc tacatgtagg
16561 atggtaacct cagaaagcaa gaatgtgaag ctcactgtga gcaatgtgct gaaagagata
16621 aaaattctta acatctttgg agttattaaa ggctttgtag aaccaggtaa agaccgcccc
16681 cccccccgc cccgcttttt tttttgtttt cttttctgtt cctaaggatg tggctagaga
16741 aggagcgagt gtaggaatgc tggcttggct tggttttatg aagtgctcaa tcttgtctgt
16801 cctaaagtta attgtttatg tgttagtttc ttttttttt tttgagaaag agtttcactc
16861 ttgttgccca ggctggagtg cagtggtgtg atctcggctc actgcaattt ccgcctccca
16921 ggttcaagcc attctcctgc ctcagcctcc ccagtagctg ggattacagg catgcgccac
16981 cacgcctggc taatttgta tttttagtag agacagggt tctccatgtt ggtcaggctc
17041 catgaggtca gagctcctga cctcaggtga tctgcctccc tcagcctccc aaagtgctgg
17101 gattacaggc atgagccacc gcgcccagcc tatgtgtcag ttttattggg aggtaataag
17161 gccctaggaa attcttgtta aaaattgacc attatgacta gaaaatctat tctaagttat
17221 tgactagacc agtgataagc aaatttctta aggggcaga taataaacct tttgccaggc
17281 tatacagtct ctcttttagc tgttcaactc tgtgggagca agaaaacagg cacagactgt
```

```
17341 gcgtagtgaa tgggcatgcg ggctgtagtt tgccagtccc tggagttaac tttaaatgca
17401 atcaaacagc caacacttac taagaaataa gtccttggac ttaagtagtc agtaaattta
17461 attagtagtg taggaaaaaa gtagctctac tagtaaggta aaattaatat tctcatgtga
17521 attttttaatt cccagagttt ttagtcagat ttgaagtaag gctcttttat ccttaataca
17581 tatactgtgc ttttaccttt ctactgatgt gctaattcta gaaaagttta gaagctgatt
17641 atataagttc tttcttcctc tttttttcttt tttaaagatc actatgttgt agttgggggcc
17701 cagagagatg catgggggccc tggagctgca aaatccggtg taggcacagc tctcctattg
17761 aaacttgccc agatgttctc agatatggtc ttaaaaggta gagtacaaat tttgattctt
17821 ttgaatattg gtgcactgca tacagttcta gatgttatac tgtgctttgc tcactttgcc
17881 tgcattcctg tggttctcat gctagactct agttcttaaa tacaaggcag attgtctttt
17941 gttgtagctg ccttttcctt tgaaacagct ttccataaag tgtcttaact gtgctagaaa
18001 tcaccagttt ctttgagaca gtggagttac tgagccctag tgcttagtgt ggtggatcca
18061 gagtgataag gtggatcata gtccctaagc aatctatttg aaagcagtag catacctctc
18121 tactcatgta ctgaggccta acagctattg aaattttgtt ctgtttattc atttattcat
18181 ttttttgagac agagtttcac tctgttgccc aggctggagt gcagtggtgt gatctcactt
18241 agctcactgc aacctctgcc tcccgacttc aagcaattct cctgcctcag cctcctgagt
18301 agctgggatt acaggcaccc acaaccacac ccggccaatt tttgtatttt tactagagac
18361 agggtttcgc catgttggcc aggctagtct cctgacctca agtgattcac ccgcctcagc
18421 ctcccaaaat gctgctagtg agccaccgtg ccctgcctct tttgtttatt tttgagcctt
18481 tctgtcctac tttccactct ttcacactcc tacccaccca cacattcaaa atcacgtcac
18541 attcttgaat cttttgggtct taggggcaaac tgcaatgctt aactttaata cagagtacat
18601 taatggagaa aaagatacag tgagggaagt gggagggatg gagggcagtg tgatacatgt
18661 aacctcaaaa ggtgctgtca caaatatagt ttctctgcaa actcttcttg taacttaaat
18721 ttgtgaattt ttattttatt ttagaattat ttttttaaaa atccaatgtt tggatttacc
18781 tctgaagatt tttctcaaga tgtgcatcat catgcttaca ctgttttcaa tgatctctgg
18841 gtccagaagt taaggaactc caagaatgaa attgtgaaag ggtgactact ggcccctgct
18901 atgtactcaa aatcttattt gcagatctcc tatcttgctc tttgtaggtt acttaaaaaa
18961 aaattattcc tattctttta ttcttttacc tggggtctca aaaaaagatt ttgttagttt
19021 ttttttttct ttttttggctc agaaaaaaaa gattttggaa tctgctatct tggaattaga
19081 ccttctgatt catcttaagt gggataccttt ccatccttgt ctgtgtataa ccttttcctca
19141 ggtaaagcta acttttttct ctttcagatg ggtttcagcc cagcagaagc attatctttg
19201 ccagttggag tgctggagac tttggatcgg ttggtgccac tgaatggcta gaggtattct
19261 ttatcatccc ttcccatatt ggacacgagc ttgtgggctt aggctgttgt ccagaagtga
19321 tgtttttata ggtttgattt taccactttt gcctttgcgt ttagtctcag tagagtccag
19381 aattgaaaat gaatccctaa tgctactgta tgtgataaat aaacagattt atacttatta
19441 gtgttttccc ttctcttcta gggatacctt tcgtccctgc atttaaaggc tttcacttat
19501 attaatctgg ataaagcggt tcttggtaag tatcccttc attagctgtt tatgaattca
19561 ggtaaacttt tttgagatgg agttttgctc ttgtcgccca gactggagtg caatggcacg
19621 atctcggctc actgcaacct ctgtctccca gattcaagcg attctcctgc cttagcctcc
19681 tgagtagctg ggattacagg tgctcactac cacacccagc taatttttttg tattttttagt
19741 agagacaggg cttcactatg ttggccagat ggtctcgaac tcctgacctc aggcgatctg
```

-continued

```
19801 cctgccttgg cctgggatta cagatgtggg ccactgtgcc tggccagata aactacttga
19861 agtggaagaa agcttttttt tttttgagac agagtctcac tgtattgccc aggctagagt
19921 gcagtggcac aatcttggct tcactgcagc cttgacctcc tgggctcagg tgatcctccc
19981 acttcagcca cctggctaat ttttttgta gagatggggt tttgccatgt tgcccaggct
20041 ggtgtcaaac tcctgagttc aagcattcta tgtcagctgc ccaaaatgct gcggttacag
20101 gcatgagcca ttgccctcag cctgtatctt aaccttcctt taaatagtct gtcaagttac
20161 acagtgagca caattgcttg tctagaacag tgggtagttc tcagtgtggc cccagatga
20221 gtagcattag gaactgttac gaaatgcaaa ctgtcatgtc taccccagac ctttgagtca
20281 gaaatgggag tgttggtcta aaaactgggc tttttgggct gggcgcagtg gtgcacgcct
20341 gtaatcccag cacttgggag gccaaggcag gcggatcacc tgaggtcagg agttcgagac
20401 cagcctggcc aacatggtga accccgtct ctactaaaaa taccaaaatt agccgggtgt
20461 ggtggcgagt acctgtaatc ccagctactc aggaggctga ggtaggagaa tcacttgaac
20521 ccgggaggca gaggttgcag tgagccaaga tggcgccatt gccctccagc ctgggcgaca
20581 gagcgagact cctctcaaaa aaacaaacaa aaaaactggg cttttttttt ggcaacccctt
20641 ggggaataaa aacctattat tttcttaagg acaaagtatc ctgaagcaaa aaaacccaaa
20701 caaagaaaca aaaaacttta acaagcacta caggtaattc tgatggacta aagttttagg
20761 accataagtc tggactatat tgaggtgaga agaaactaaa ctatgccata tagaatggta
20821 cttagagagt aattcacatc ctgttacgtt gtggcatcac tgatagaaat attggataat
20881 gaaacttcta gaagagtttg aatgttcact ggcagcagaa aattgacaaa agggtttgaa
20941 tgttatttaa agtgcagctg tccattcaac aggaatgggg taaaaaagaa agtgcagatg
21001 tagctgatga gctgagaata gtgaaatgtc tacatggggg aaaaaaggaa agagttacaa
21061 ttaaacctct ctaggttagt tatttccctg ttgtatgttt gccgcagaat gtgctgagta
21121 tagcaagcat actatgtata gctctaacct gggtgaacca gaaagttaaa catgaaattg
21181 ctaatggggg aggctgcaca tgtgtggggg cagtggattt atgggacctc taggtaccct
21241 tctcttaatt ttgctgctga acctaaaact ggtctgattt tttttttttt ttttttttt
21301 tttgagatgg agtctcgctt tgtcacccag gctggagtgc agtggcgcca tcccagctca
21361 ctgcaagctc cgcctcccgg gttcatgcca ttctcctgcc tcagcctccc gagtagctgg
21421 gactacaggt gcccgccacc acaccgcct aattttttgt atttttagta gagacggggt
21481 ttcaactgtg ccagccaaga tggtctcgat ctcctggacc ttgtgatcca cccgtctggg
21541 cctcccaaag tcctgggatt acaggcgtga gccaccgtgc ccggcctaac tgctctgata
21601 ttttttaaaaa aggtgacttg gattaaagta tgcaaactca aggagtagta cgagcccact
21661 tgagtgaagt tagcttagtt gctaaagagc ttgataccaa aattattttg tttattgatg
21721 aatgggatag ttgttgcaca gggccactga tctagattac tgtcttattt gtcaagtact
21781 tatagttgta gaagtagcag tgtgaaaatt atcggaatgg agaaggggca atgataaaac
21841 aatttatttt caggtaccag caacttcaag gtttctgcca gcccactgtt gtatacgctt
21901 attgagaaaa caatgcaaaa tgtgagtata acctcatta caaaaatgta tgacttaatt
21961 tttgttgaat caacctgaga taaaaacac tgatatgtaa accgtagtca gtaacaaaaa
22021 ataggaattg agaataaatt ttatagcagc gttatttaag ggatacttgc ctattgaacc
22081 atatgagatg agggctccaa tcttaaagaa tatgttgttt atttaggaat atataacaaa
22141 atgccatgag gcctaagctg tagtgcaggg gcccacaggg gattgtctat agagtcacaa
```

-continued

```
22201 tgctaaggaa ggcttaaatc aacttgaact atactttgag aaggccggag gaaatattca
22261 ttgaataaac aattaccata gttttgaatg agggagagca tgtgaaagaa atatttgcc
22321 tatgtggggt gggggagggg gagagggata gcattgggag atatacctaa cgctagatga
22381 cgagttagtg ggtgcagtgc accagcatgg cacatgtata catatgtaac taacctgcac
22441 aatgtgcaca tgtaccctaa aatttaaagt ataattaaaa aataaataaa taaataaata
22501 aaaaagaaaa tatttgccta atgggattag aggctgtata ttggagtgag taaagttaga
22561 aacaggtcag atagcagaca ttggccttga tccaagagat actagggatt ataggatctc
22621 aagcaaggtg atcatgaatt tgccagttag gttggtggca taagatgcac tagaaggaag
22681 aaaccagaaa caagataggc atagtgtgaa gcccagagag ggcttttaca attgtgggta
22741 agccaccatg gttttgtttg tttgtttgtt tgttttttgag atggagtctt cctctgtctt
22801 cctccagcac tcaggctgga gtgcaatggt gcgatcttgg ctcactgcag cctccacctc
22861 ctgggttcaa gcgattctcc tgcctcagcc tcctgaggag ctgggactac aggtgcacac
22921 caccacacct ggctaatttt tgtattttta gtagagacgg gtttcacca tgttggccag
22981 gatggtctca atcccttgac ctcatgatct cttgaccttg gcctcccaaa atgctgggat
23041 tacaggtgtg agccaccgcg cccagctttt attcattttt ttttcctttt ttttttttaa
23101 gagataaagt cttgctgtgt tgcccaggct agtctcaaac ttctgggctc aagtgatcct
23161 cccagctcgg cctcccaaag tgttgggatt gcagttgtga actaccccac ccggcctagg
23221 cccactttta aaatgttaat taagaagaaa acattttttc ctcaccataa ctaaaggaac
23281 tgacaacatg agcctagtta gtaataactt aaagttgaga ttgttttaac tatcataaat
23341 aatttctttt caagaagata taatacaagt tttttattta aaaattgtta tagagtaaca
23401 tgttagtgac tagcctgaat aaataagttc caaaaggtta gttttaatga aatttctta
23461 tcttacaggt gaagcatccg gttactgggc aatttctata tcaggacagc aactgggcca
23521 gcaaagtgta agttgagaaa agtgaatgaa caaactaata gaaaagcaga gattctacct
23581 actacattag gtagaatcta aatctgtcct tgcattgaac ttacttacac ctaaagatat
23641 tcagctaaag aatttatttt ggatgggggg actagcacga tagaacagtc tattctttaa
23701 aacactttct aaagacacat tctttgtctt tgcagtgaga aactcacttt agacaatgct
23761 gctttcccctt tccttgcata ttctggaatc ccagcagttt ctttctgttt ttgcgaggta
23821 agtctgttca tttaaatgac aaatggagag aggctctcta aaaggaagtg atctgtattt
23881 gggaataggg cattgcaatg ggaatgcctg tgctatagtc aactatgtac atattcagag
23941 gagtaaagga aaacaagttt ttaaggacaa atgatgagga ttacaaaatt actttgaggt
24001 aattattctt ggctaccaag atcaataaca aggatgacac cagtccaagg ttgacaggca
24061 gttgctaggc agattttctc acgagagaag tttttggtg caaggttgca gtggcctttg
24121 tgtaaggttg tagttttttgt aaaaaggaaa aaaaaccct taatccttgt tatcagacat
24181 acaagggtga gacccttctc ttcagggttg catttttgtt aacactagtg actccatttt
24241 gattttgaca acttgcacat atcttagttg ttgggttttt tttgtttgtt ttttgttttg
24301 ttttttttt ttttttgaca atggtgactt gctctgtcac ccaggctggg gttgcagtgg
24361 cccgatcatg gctcactgca gcctcaagca gtcctccccc ttcagcctcc aaactgtttg
24421 gattataggc aagagctact tactacacct ggccatggat cttcttgtgt caactttgag
24481 accaaattta ctgcagtgct taaatgtttt taagaattat acacatgtgc tggatgtggt
24541 agctcacgcc tgtaatcctg tagcaggaca agccgcagac aaatccctc agacaccgag
24601 ttaaagaagg aagggcttta tttggctggg agctttggca agactcacgt ctccaaaaac
```

-continued

```
24661 tgagctcccc gagtgagcaa ttcctgacct ttttaagggc ttacaactaa gggagtctgc
24721 gtgagagggt cgtgatcaat tgggcaagca gggggtacat gactgggggt tgcatgtacc
24781 ggtaattaga acagaacaga acaggacggg attttcacag tgcttttcta tacaatgtct
24841 ggaatctata gataacataa ctggttaggt cagggctcga tctttaacca ggtccagggt
24901 gcggcagcgc tgggctgtcc acctctgcct tttagttttt acttcttctt tctttggagg
24961 cagaaattgg gcataagaca atatgagggg tggtctcctc ccttaatccc agcactttgg
25021 gaggccaagg aaggcggatt acgaagtcag gagtttgaga ctagcctgac caaaatggtg
25081 aaaccccgtc tctgctaaaa atacaaaaat tagtcggaca tagtggcgtt gtgcctgtaa
25141 ccccagctac tcaggaggct gagcaggaga atcgcttgaa cctgggaagc agagttgcag
25201 tgagcctgag aatggaccac tgcactgcag ctggggttta ggtgacaga cgcttgggtg
25261 acagagcaag accctgtctc caaaaaaaaa agttatacac atgtaattat tgcatgttcc
25321 ttcattatta gttttaacaa ctagacttgt taatctcaat agcttaatta gcatttgagt
25381 ttattgctaa aattctttat gagttttaat aatgaggctt ggccgagtgt ggtgggtcat
25441 acctgtaatc ccagcatttg ggaggccaag gcgggtagat cacttgaggt caggagttca
25501 agaccagcct ggccaacatg gttaaacccc atctctacta aaaatacaaa aaattagct
25561 gggcatggtg gcacatgcct ataatcccag ctgctcagga ggctgaggtg gaagaatcgc
25621 ttgaacccag ggggcagagg ttgcagtgag ccgagatcgt gccattgcac tctagcctgg
25681 gcaacagagc aagatcgtct aacaacaaca acaaaaaaac caaggctgaa tttcttgagt
25741 gattgagcag tggctatcta ttggacagtc cagctgaaca gtattttttcc tcaggctggg
25801 tgcagtaact ctcacctata ttccggcaca ttgggtggct gaggtgggca gatcacttga
25861 ggccaggagt gagaccagcc tgggtaacgt gcctagacta tatctctaca aaaaattttt
25921 taaataaagc tggcccagtg gccagctgta gtcccaactc cttgggaggc tgaggcaggg
25981 gggtcacttg agctaggagc ttaaggctgt ggggagccat gattgcatca ccacgctcca
26041 gcctgggtga cagagtgact cgtctcaagg ctgcaggag ccatgattgc atcactgcac
26101 tccagcctgg gtgacagaga gaggcctcgt ctcaaggctg cggggagctg tgattgcatc
26161 actgcactct agcctgggtg acagagtgac ctcgtctcaa ggctagaggg agccatgatt
26221 gcatcactgc actccagcct gggtgacaga gagagacctc gtctcaaggc tgcagggagt
26281 catgattgca tcgctgcact ctagcctggg tgacagagac cttgtctcaa ggctgcgggg
26341 agtcatgatt gcattgctgc actctagcct gggtgacaga gagaccttgt ctcaaggctg
26401 tggggagtcg tgattgcatc actgcactct agcctgggtg acagagagac ctcgtctcaa
26461 ggtatgtttc atgtatcttc tctttttca ttgataaagg cccaaacttc ccagagagaa
26521 aaacatacag ccttaaggaa tttggctaga agtctattca gggcatatga tacgatagaa
26581 cagggattct gtagaacctg gaagaaagta gtcaactcta ggagtaggtt agcttgagag
26641 aagtagcaag aatgtactta aagcagcaga taatgagata gaattggggt aaattgcggt
26701 aggaatatgt tagaagcaag ggtggaactg tcgtcactgt tacctcgatg gcgaagccag
26761 aatgtgaggc tcttgctctt agaactcacg tgagtaccat agcctcgcat tgtctcacag
26821 gacacagatt atccttattt gggtaccacc atggacacct ataaggaact gattgagagg
26881 attcctgagt tgaacaaagt ggcacgagca gctgcagagg tcgctggtca gttcgtgatt
26941 aaactaaccc atgatgttga attgaacctg gactatgaga ggtacaacag ccaactgctt
27001 tcatttgtga gggatctgaa ccaatacaga gcagacataa aggtgagcac tgattccaat
```

-continued

```
27061 tacgttttta ttttgctgaa tgtcaagtat tttgaaatgt gatgtgttcc tgtgtgttcc
27121 tgttggaagg gtgattgtag ccatagtaca tttttaaagtg aactgaggta taattgtatg
27181 tagaattggt aacttgtttg agagaagtcg ggaggctgtg gattagagac ctaggacaga
27241 gctcagcagg tgtttcagaa tccagagcag tgtcaggttt tctgtcactc atgtctccca
27301 ggcagcccgt cagtaggaca cggaatatga agatctcagc aaggagttgg gctgtgtgcc
27361 tctcgggcgt gacccggatg gaaagacagc acagctagca ggattccatc tcgtagtgat
27421 ctgcgcatct aaaagtcaaa tattctatta aacgaaactg ataagcaggg tgaggtggtg
27481 catacccgta gccccagcta cttctgctga ggcaggagga ttgctggagt ccagcccagg
27541 caacatagca aaatcccatc tctaaataaa ttaataaaac taatattaaa gtagcttcca
27601 gattgtttta tggtactagg agttgatttt taacagatct cttaattgaa gtaaatcact
27661 gacaaccgaa tcttttttata tctttttttat ttttattttt attttatttt ttttgagaga
27721 tgaagtctcg ctcttgtccc ccaggctgga atgcaatgac atgatctcgg ctcactgcaa
27781 cctccacctc ccggctttaa gcgattctcc tgcctcggct ccccaggtag ctgggattac
27841 aggcgtgtgc caccatgccc agatagtttt tgtgttttta agtagaagcc ggggttttac
27901 catgttggcc aggctgaagt gcagtggcga gatctcggct cactgtaaga tgcgcctccc
27961 gggttcacgc cattctcctg cctaagcctc ccgagtagct gggactacag gtgccggcca
28021 ccacgcccgg ctaattttt gtattttttag tagagccggg gttttaccat gttggccagg
28081 ctggtcttga actcctgacc tcaggtgatc cacccacctc ggcctcccaa agtgctggga
28141 tcacaggcat gagccaccac gcccggcatc ttatgtcttt cttgaaacta attgtaactg
28201 ttgaaaatgg aacttaccag gtggaaataa ctaaatcctg aagtaccttg aaccaaaatg
28261 ttttcccta tagggacatt ttcctccaaa aggagaattg aactggaaac aatatagtac
28321 ataggattat ataattatgt tcaatttctt aatgagaatg gttttcttac atgctgggct
28381 caaatatgag tgtatatcac agtccataga gcttggaacc cctgtgcaag gtgctttcgg
28441 agtcttgagc ttatctgcga gttcctttta tcagaatctt acttaacgca cgttaaatta
28501 gaaaggcata caaaagaatg tccttagaaa taaaacttct catagcgaat aatgtctgtt
28561 tcaggaaatg ggcctgagtt tacagtggct gtattctgct cgtggagact tcttccgtgc
28621 tacttccaga ctaacaacag atttcgggaa tgctgagaaa acagacagat ttgtcatgaa
28681 gaaactcaat gatcgtgtca tgagagtaag tgaacttttg ggaaaggagg aactaaagta
28741 tgtgtaaaat aaccgataaa tcttacactt ctgcaaagtg gacaaactct aggagtctag
28801 aattcctttta agaagggagc attaatggtt tagctgtcat tttctgtttc tgctgtctaa
28861 ttcagaactt agtcaaacct agtctttttg gaagagactt gctgtaaaac ttccatgtat
28921 gctccaatgg ggaaaagatc tgaacacatt taaagttttc ctttgtaaaa tgaatcagtt
28981 tcctttaaaa aaaattttttt tttttgaga cagagtttca ctgttgttgc ccaagctgga
29041 gtgcaatggc acggtctcgg ctcactgcac cctccacctc ccaggttcaa gtgattctcc
29101 tgccttagcc tcccgagttg ctgtgattac aggtgcccaa caccacgccc ggctcatttt
29161 ttgtattttt agtagaaacg gagtttcacc atgttagcca ggccggtctc gaactcccaa
29221 cctcaagtga tccacctgcc ttggcctccc aaagtactgg tattacaagc gtgagccgct
29281 gtgcccagcc tcctttagaa ttttaaccttt agaagattag cattagcctg attctcagca
29341 ttctttttttc cttactctgc tatagaaagt ctgatcagct ggctgggtac agtggctcat
29401 gcctgtaatt ccagtacttt gggaggccga ggcaagcgga tcacctgagg tcaggagttc
29461 aagaccagcc tgaccaacat ggagaaaccc catctctact aaaaatacaa aaattagctg
```

-continued

```
29521 ggcgtggtgg tgcatgcctg taattccagc tgctcaggag gctgaggcag gagaattact
29581 tgaacccggg aggtggaggt tgcagtgagc tgagatcgcg ccattgtact ccagcctggg
29641 caacaagagc gaaactctgt ctcaacaaca acaaaaagcc gggcacggtg gctcacacct
29701 gtaatcccag catgaattgc ttgaactcgg gaggtggagg gtaccagtga gccgagatag
29761 cgctgttgca ctccagtctg ggcaacaaga gcgaaactct gtgtcaaaaa aaaaaaaaaa
29821 aaaaaagtct gatcggcatt cttaaatttg ggacatttta catttgaagt gaactgttgt
29881 tttactacaa aagtcacagg gctgtgtaaa ttgccttgtg tgttgttttc gtaggtggag
29941 tatcacttcc tctctcccta cgtatctcca aaagagtctc ctttccgaca tgtcttctgg
30001 ggctccggct ctcacacgct gccagcttta ctggagaact tgaaactgcg taaacaaaat
30061 aacggtgctt ttaatgaaac gctgttcaga aaccagttgg ctctagctac ttggactatt
30121 cagggagctg caaatgccct ctctggtgac gtttgggaca ttgacaatga gttttaaatg
30181 tgatacccat agcttccatg agaacagcag ggtagtctgg tttctagact tgtgctgatc
30241 gtgctaaatt ttcagtaggg ctacaaaacc tgatgttaaa attccatccc atcatcttgg
30301 tactactaga tgtcttttagg cagcagcttt taatacaggg tagataacct gtacttcaag
30361 ttaaagtgaa taaccactta aaaaatgtcc atgatggaat attcccctat ctctagaatt
30421 ttaagtgctt tgtaatggga actgcctctt tcctgttgtt gttaatgaaa atgtcagaaa
30481 ccagttatgt gaatgatctc tctgaatcct aagggctggt ctctgctgaa ggttgtaagt
30541 ggtcgcttac tttgagtgat cctccaactt catttgatgc taaataggag ataccaggtt
30601 gaaagacctt ctccaaatga gatctaagcc tttccataag gaatgtagct ggtttcctca
30661 ttcctgaaag aaacagttaa ctttcagaag agatgggctt gttttcttgc caatgaggtc
30721 tgaaatggag gtccttctgc tggataaaat gaggttcaac tgttgattgc aggaataagg
30781 ccttaatatg ttaacctcag tgtcatttat gaaagagggg gaccagaagc caaagactta
30841 gtatatttc ttttcctctg tcccttcccc cataagcctc catttagttc tttgttattt
30901 ttgtttcttc caaagcacat tgaaagagaa ccagtttcag gtgtttagtt gcagactcag
30961 tttgtcagac tttaaagaat aatatgctgc caaattttgg ccaaagtgtt aatcttaggg
31021 gagagctttc tgtccttttg gcactgagat atttattgtt tatttatcag tgacagagtt
31081 cactataaat ggtgtttttt taatagaata taattatcgg aagcagtgcc ttccataatt
31141 atgacagtta tactgtcggt ttttttaaa taaaagcagc atctgctaat aaaacccaac
31201 agatcctgga agttttgcat ttatggtcaa cacttaaggg ttttagaaaa cagccgtcag
31261 ccaaatgtaa ttgaataaag ttgaagctaa gatttagaga tgaattaaat ttaattaggg
31321 gttgctaaga agcgagcact gaccagataa gaatgctggt tttcctaaat gcagtgaatt
31381 gtgaccaagt tataaatcaa tgtcacttaa aggctgtggt agtactcctg caaaattta
31441 tagctcagtt tatccaaggt gtaactctaa ttcccatttt gcaaaatttc cagtaccttt
31501 gtcacaatcc taacacatta tcgggagcag tgtcttccat aatgtataaa gaacaaggta
31561 gtttttacct accacagtgt ctgtatcgga gacagtgatc tccatatgtt acactaaggg
31621 tgtaagtaat tatcgggaac agtgtttccc ataatttttct tcatgcaatg acatcttcaa
31681 agcttgaaga tcgttagtat ctaacatgta tcccaactcc tataattccc tatcttttag
31741 ttttagttgc agaaacattt tgtggcatta agcattgggt gggtaaattc aaccactgta
31801 aaatgaaatt actacaaaat ttgaaattta gcttgggttt ttgttacctt tatggtttct
31861 ccaggtcctc tacttaatga gatagtagca tacatttata atgtttgcta ttgacaagtc
```

```
-continued
31921  attttaactt tatcacatta tttgcatgtt acctcctata aacttagtgc ggacaagttt 31981  taatccagaa ttgacctttt gacttaaagc aggggggactt tgtatagaag gtttgggggc 32041  tgtggggaag gagagtcccc tgaaggtctg acacgtctgc ctacccattc gtggtgatca 32101  attaaatgta ggtatgaata agttcgaagc ttcgtgagtg aaccatcatt ataaacgtga 32161  tgatcagctg tttgtcatag ggcagttgga aacggccttc tagggaaaag ttcatagggt 32221  ctcttcaggt tcttagtgtc acttacctag atttacagcc tcacttgaat gtgtcactac 32281  tcacagtctc tttaatcttc agttttatct ttaatctcct cttttatctt ggactgacat 32341  ttagcgtagc taagtgaaaa ggtcatagct gagattcctg gttcgggtgt tacgcacacg 32401  tacttaaatg aaagcatgtg gcatgttcat cgtataacac aatatgaata cagggcatgc 32461  attttgcagc agtgagtctc ttcagaaaac ccttttctac agttagggtt gagttacttc 32521  ctatcaagcc agtaccgtgc taacaggctc aatattcctg aatgaaatat cagactagtg 32581  acaagctcct ggtcttgaga tgtcttctcg ttaaggagat gggccttttg gaggtaaagg 32641  ataaaatgaa tgagttctgt catgattcac tattctagaa cttgcatgac ctttactgtg 32701  ttagctcttt gaatgttctt gaaattttag actttctttg taaacaaatg atatgtcctt 32761  atcattgtat aaaagctgtt atgtgcaaca gtgtggagat tccttgtctg atttaataaa 32821  atacttaaa
```

By "agent" is meant a peptide, nucleic acid molecule, or small compound.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

The term "antibody," as used herein, refers to an immunoglobulin molecule which specifically binds with an antigen. Methods of preparing antibodies are well known to those of ordinary skill in the science of immunology. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

Antibodies can be made by any of the methods known in the art utilizing a polypeptide of the invention (e.g., an arenavirus GP1 polypeptide), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a polypeptide of the invention or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding the polypeptide, or immunogenic fragments thereof, can be expressed in cells in vitro, followed by isolation of the polypeptide and administration of the polypeptide to a suitable host in which antibodies are raised.

Alternatively, antibodies against the polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to ‘display’ the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

By "anti-GP1 antibody" is meant an antibody that selectively binds an arenavirus GP1 polypeptide, including for example the GP1 polypeptide of a New World arenavirus. In various embodiments, the anti-GP1 antibody specifically binds a GP1 receptor-binding site. Exemplary anti-GP1 antibodies include GD01, CR1-28, and CR1-07. In various embodiments, the anti-GP1 antibody has at least about 85% or greater amino acid identity to a CR1-28 or CR1-07 amino acid sequence provided below.

```
CR1-07 CDR H1 sequence
                                   (SEQ ID NO: 1)
GFTFGTSI CR1-07 CDR H2 sequence
                                   (SEQ ID NO: 2)
ISHDESRK CR1-07 CDR H3 sequence
                                   (SEQ ID NO: 3)
AKDLSPPYSYAWDIFQYW CR1-07 CDR L1 sequence
                                   (SEQ ID NO: 4)
QSVLYSSRSDNKY CR1-07 CDR L2 sequence
                                   (SEQ ID NO: 36)
WAS CR1-07 CDR L3 sequence
                                   (SEQ ID NO: 5)
QQYYSSPPTF CR1-28 VH sequence
                                   (SEQ ID NO: 11)
QVQLVESGGGVVQPGRSLRLSCAASGFTFSSSAMHWVRQAPGKGLE

WVAVIWSDGSNENYADSVKGRFTISRDNSKNTLYLQMSSLRAEDTAVYY

CATDKTYVSGYTSTWYYFNYWGQGTLVTV

S

CR1-28 VL sequence
                                   (SEQ ID NO: 12)
DIQMTQSPSTLSASVGDRVTITCRASQSIDNWLAWYQQKPGKAPKLLIY

TASRLESGVPSRFSGSGSGTEFTLTISSLQPDDFATYYCQHRTFGQ

GTKVEIK

CR1-28 CDR H1 sequence
                                   (SEQ ID NO: 6)
GFTFSSA CR1-28 CDR H2 sequence
                                   (SEQ ID NO: 7)
IWSDGSNE CR1-28 CDR H3 sequence
                                   (SEQ ID NO: 8)
ATDKTYVSGYTSTWYYFNY CR1-28 CDR L1 sequence
                                   (SEQ ID NO: 9)
QSIDNW CR1-28 CDR L2 sequence
                                   (SEQ ID NO: 37)
KAS CR1-28 CDR L3 sequence
                                   (SEQ ID NO: 10)
QHRT CR1-07 VH sequence
                                   (SEQ ID NO: 13)
QVQLVESGGGVVHPGRSLRLSCAASGFTFGTSIMHWVRQAPGKGMQW

VAQISHDESRKFYSDSVKGRFTVSRDNSKNTLFLEMSSLRIEDTAVYYCA

KDLSPPYSYAWDIFQYWGQGSLVTVS

CR1-07 VL sequence
                                   (SEQ ID NO: 14)
DIVMTQSPESLAVSLGERATINCKSSQSVLYSSRSDNKDYLAWYQQKP

GQSPKLLIYWASTRESGVPERFTGSGSGTDFTLSISSLQAEDVAVYYC

QQYYSSPPTFGGGTKVELK
```

In other embodiments, the anti-GP1 antibody has at least about 85% or greater amino acid identity to a GD01 amino acid sequence provided below.

```
GD01 CDR H1 sequence
                                   (SEQ ID NO: 19)
NYWMQ GD01 CDR H2 sequence
                                   (SEQ ID NO: 20)
AVYPGDGDTRFSQKFKG GD01 CDR H3 sequence
                                   (SEQ ID NO: 21)
ARRRVYYGSNYIYALDY GD01 CDR L1 sequence
                                   (SEQ ID NO: 22)
QNVGSA GD01 CDR L2 sequence
                                   (SEQ ID NO: 38)
SAS GD01 CDR L3 sequence
                                   (SEQ ID NO: 23)
QQYSSYPLAF
```

-continued

CR1-07 VH sequence
(SEQ ID NO: 24)
EVKLQQSGAELARPGTSVKLSCKASGYTFTNYWMQWIKQRPGQGLEWIG

AVYPGDGDTRFSQKFKGKATLTADKSSSTAYMQLSSLSSEDSAVYFCAR

RRVYYGSNYIYALDYWGQGTSVTVSAAKTTAPSVYPLAPVCGDTTGSSV

TLGCLVKGYFPEPVTLTWNSGSLSSGVHTFPAVLQSDLYTLSSSVTVTS

STWPSQSITCNVAHPASSTKVDKKIEPRVPKGEFQHTGGRY

CR1-07 VL sequence
(SEQ ID NO: 25)
DIVMTQSQKFMSTSIGDRVSITCKASQNVGSAVAWYQQKPGQSPKLLIY

SASNRYTGVPDRFIGSESGTDFTLTISNMQSEDLADYFCQQYSSYPLAF

GAGTKLELKRADAAPTVSIFPPSSEQLTSGGASVVCFLNNFYPKDINVK

WKIDGSERQNGVLNSWTDQDSKDSTYSMSSTLTLTKDEYERHNSYTCEA

THKTSTSPIVKSFNRNEC

By "biological sample" is meant any liquid, cell, or tissue obtained from a subject. In some embodiments, the biological sample is blood.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. In various embodiments, the disease is a viral hemorrhagic fever.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any clinical indicator, protein, metabolite, or polynucleotide having an alteration associated with a disease or disorder.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence;

for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a murine, bovine, equine, canine, ovine, or feline. In one aspect, the subject is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 depicts the structure of a JUNV GP1-neutralizing antibody complex. Ribbon diagram of JUNV GP1 (left side of structure) bound to the GD01 Fab (heavy chain ($V_H$, $C_H1$) shown below the light chain ($V_L$, $C_L$). $V_H$, $V_L$, $C_H1$, and $C_L$, respectively denote the antibody variable heavy, variable light, constant heavy 1, and constant light chain domains. The antibody CDR loops (CDR L1, CDR L3, CDR H1, CDR H2, and CDR H3) that contact GP1 are labeled. GP1 glycans are shown as sticks. GP1 disulfides are shown in yellow.

FIG. 2 depicts details about the JUNV GP1-GD01 interface. The GD01 variable heavy ($V_H$) and variable light ($V_L$) interacting segments are shown along with JUNV GP1 in ribbon diagram with a semi-transparent surface representation. The color scheme is as presented in FIG. 1. Top left: CDR H3 includes a cluster of three tyrosines that fit into a shallow groove on the concave face of GP1. Bottom left: CDRs H1 and H2 form a network of polar contacts with GP1 Loop 7 and the C-terminal end of loop 3. Top right: CDR L1 contacts the conserved GP1 Asn178 glycan. Bottom right:

CDR L3 provides additional contacts to GP1 loop 3. The asterisk indicates a potential glycan for which density could not be observed.

Figures 3A, 3B:
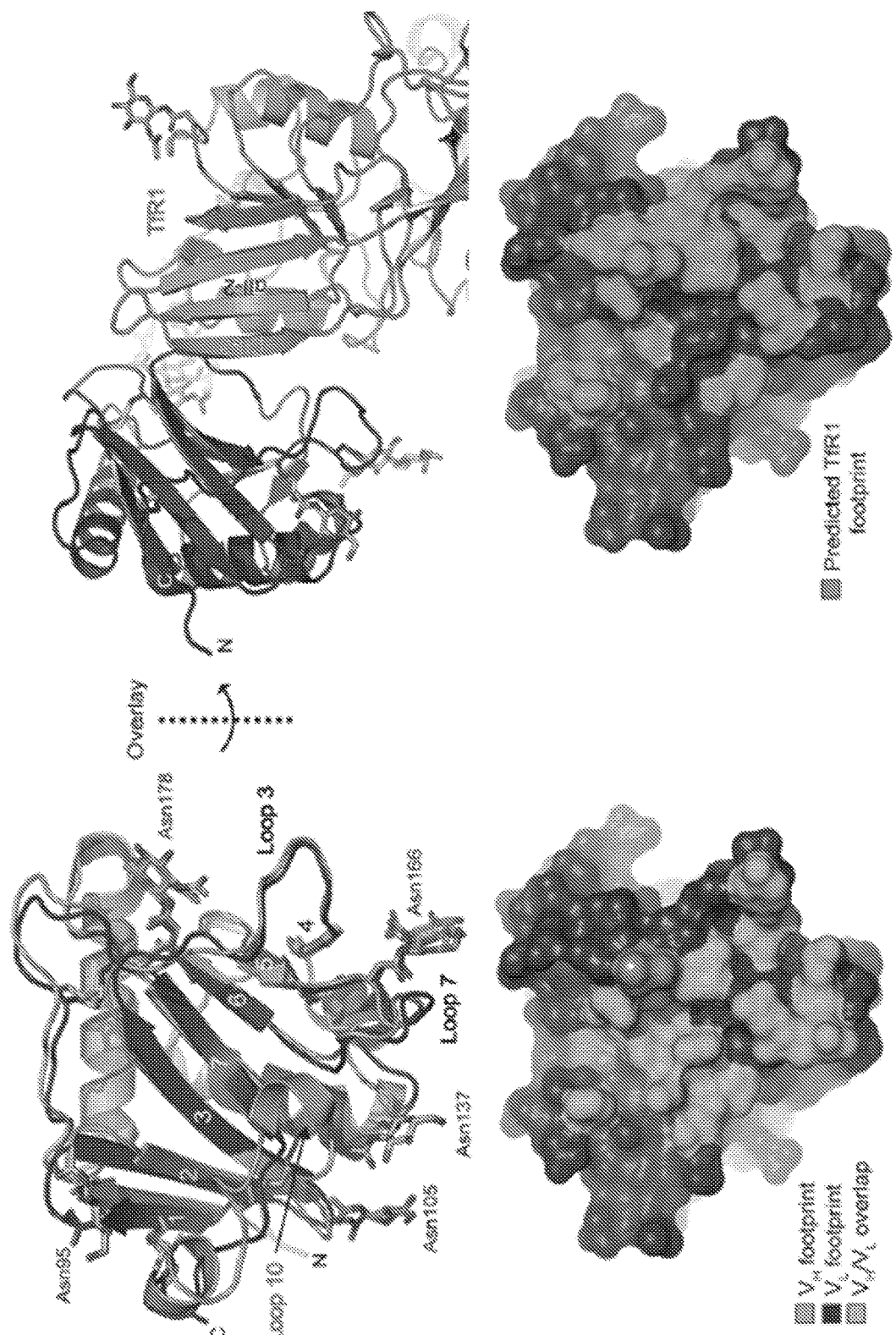
Figure 3C:
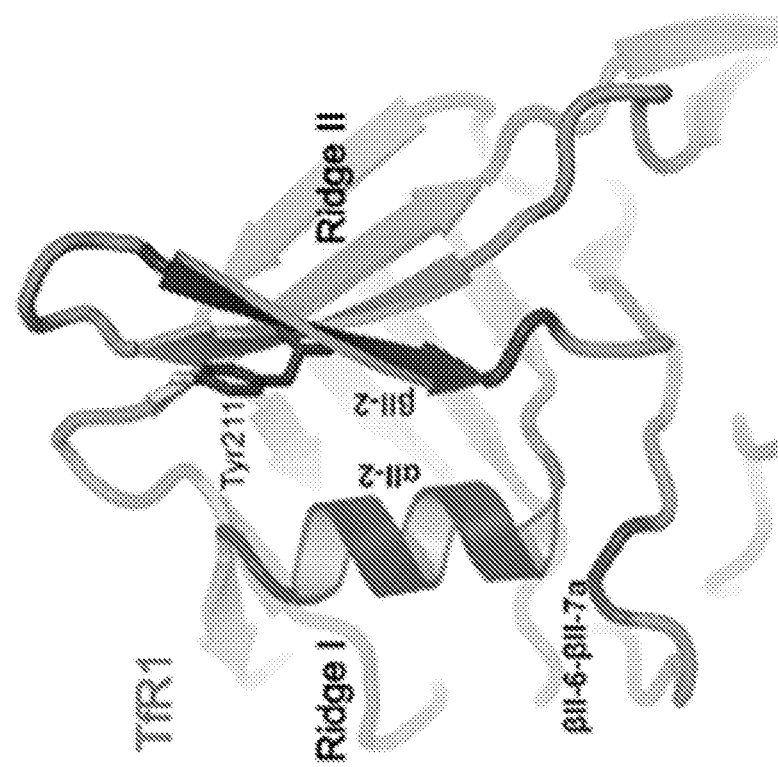
Figure 3C:
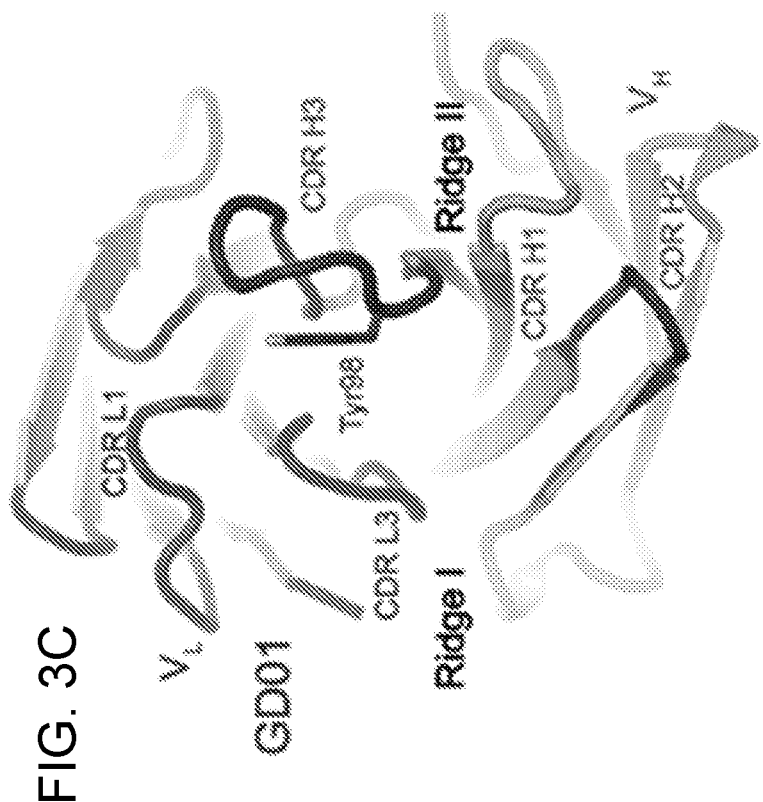

FIGS. 3A-3C depict the overlap of GP1 receptor and GD01 footprints on GP1. FIG. 3A depicts a structural comparison of JUNV GP1 and MACV GP1. Left panel: Overlay of ribbon diagrams of JUNV GP1 and MACV GP1 (from PDB ID: 3KAS). N-linked glycans are shown as sticks (for MACV and JUNV), and disulfides are shown. Right panel: Superposition of JUNV GP1 onto the MACV GP1: TfR1 structure (PDB ID: 3KAS). MACV GP1 is omitted for clarity. FIG. 3B depicts a comparison of the footprint of GD01 and the predicted footprint of GP1 receptor TfR1 on the surface of JUNV GP1. Left panel: Surface representation of JUNV GP1 with the antibody $V_H$ and $V_L$ chain footprints colored in light and dark, respectively. An overlapping contact is shown as indicated. Right panel: Surface representation of JUNV GP1 with predicted TfR1 footprint shown. FIG. 3C depicts a comparison of GD01 CDRs and TfR1. Left panel: GD01 CDRs L1 and L3 and CDRs H1, H2 and H3 form two ridges (shown in red) that the antibody present to GP1. Tyr98 from the antibody heavy chain is shown as sticks. Right panel: TfR1 also presents two ridges to GP1 formed by the helix αII-2, the βII-2 strand, and loop βII-6-βII-7a in its apical domain. Tyr211 in the βII-2 strand of the receptor is shown as sticks.

Figure 4A:
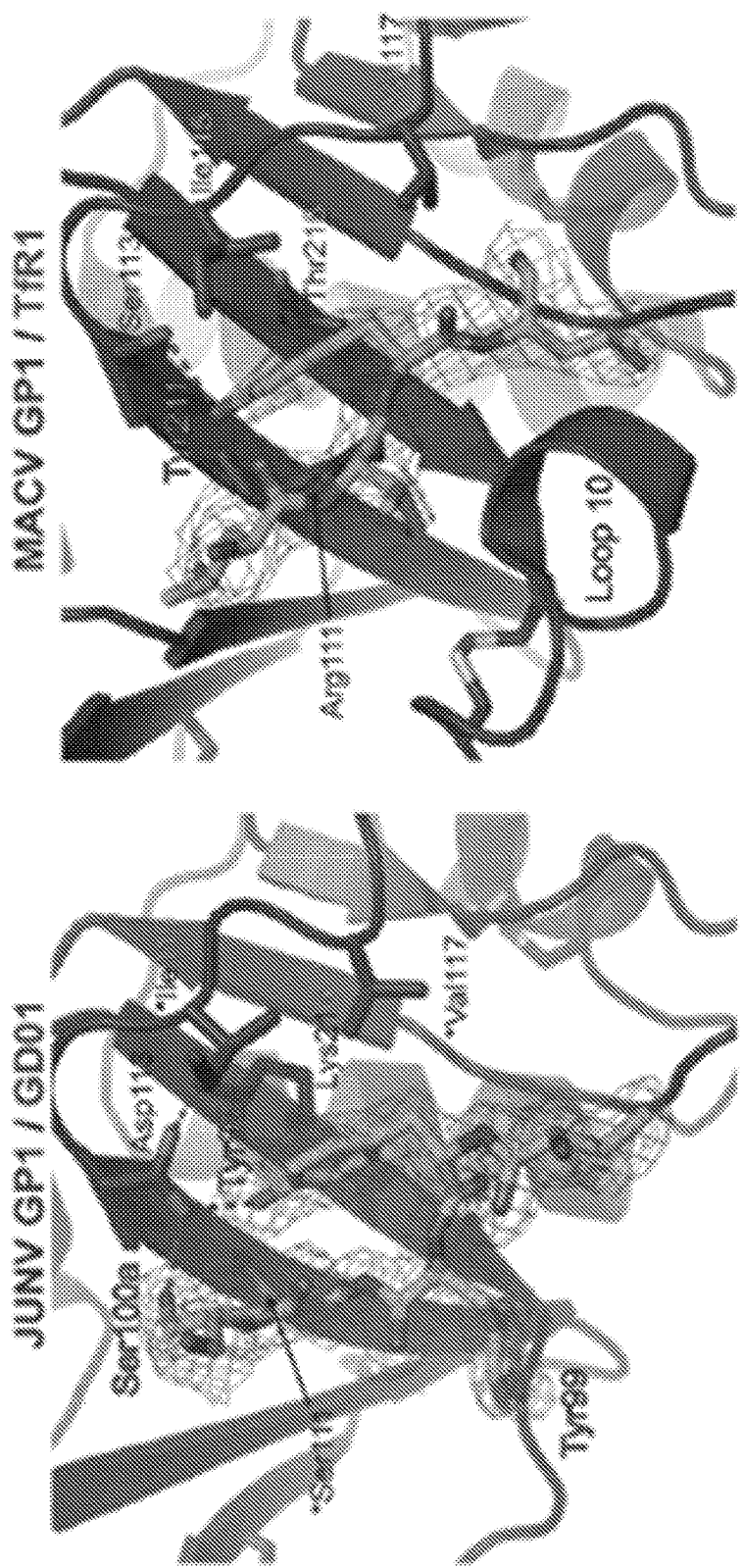
Figure 4B:
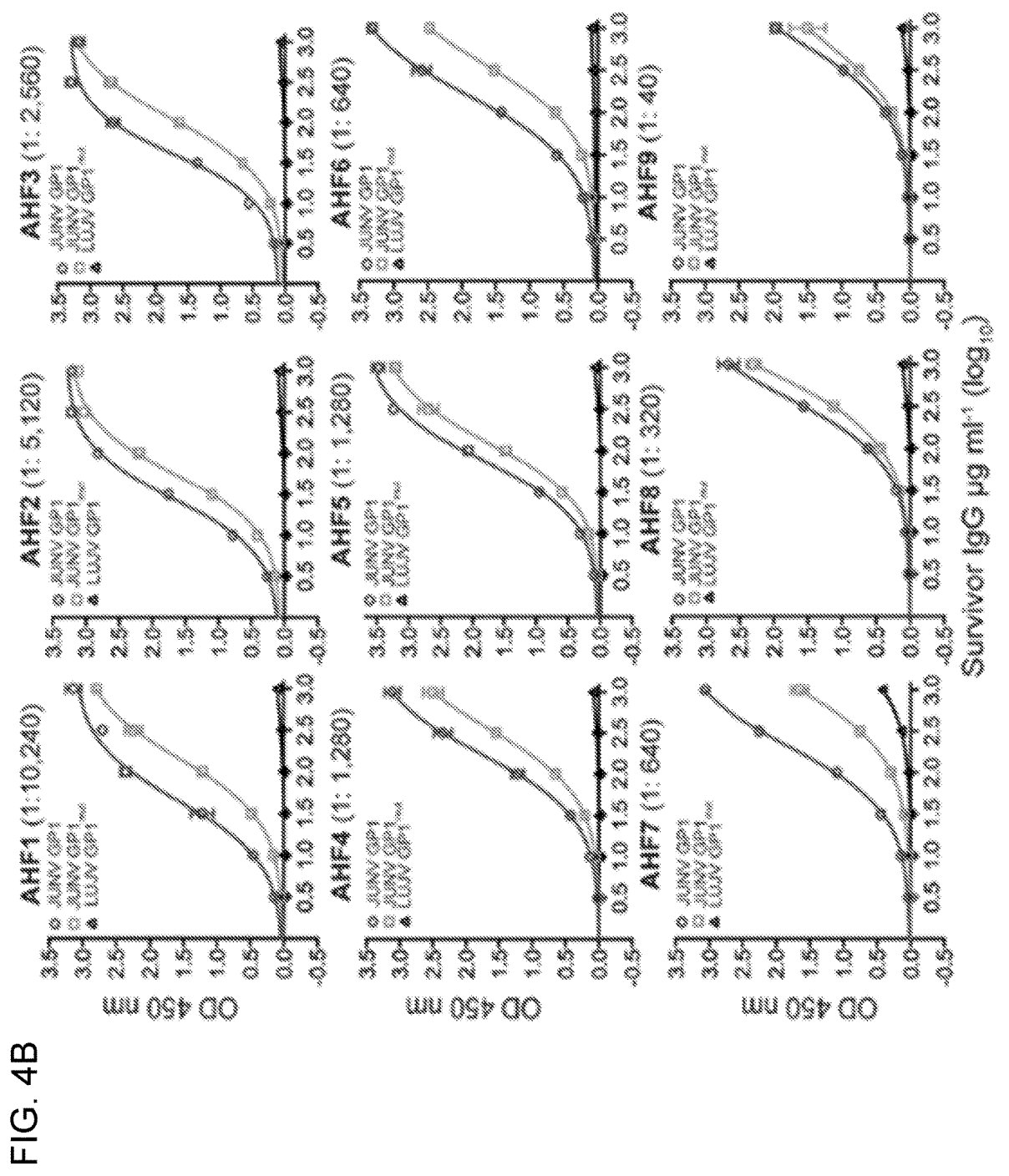
Figure 4C:
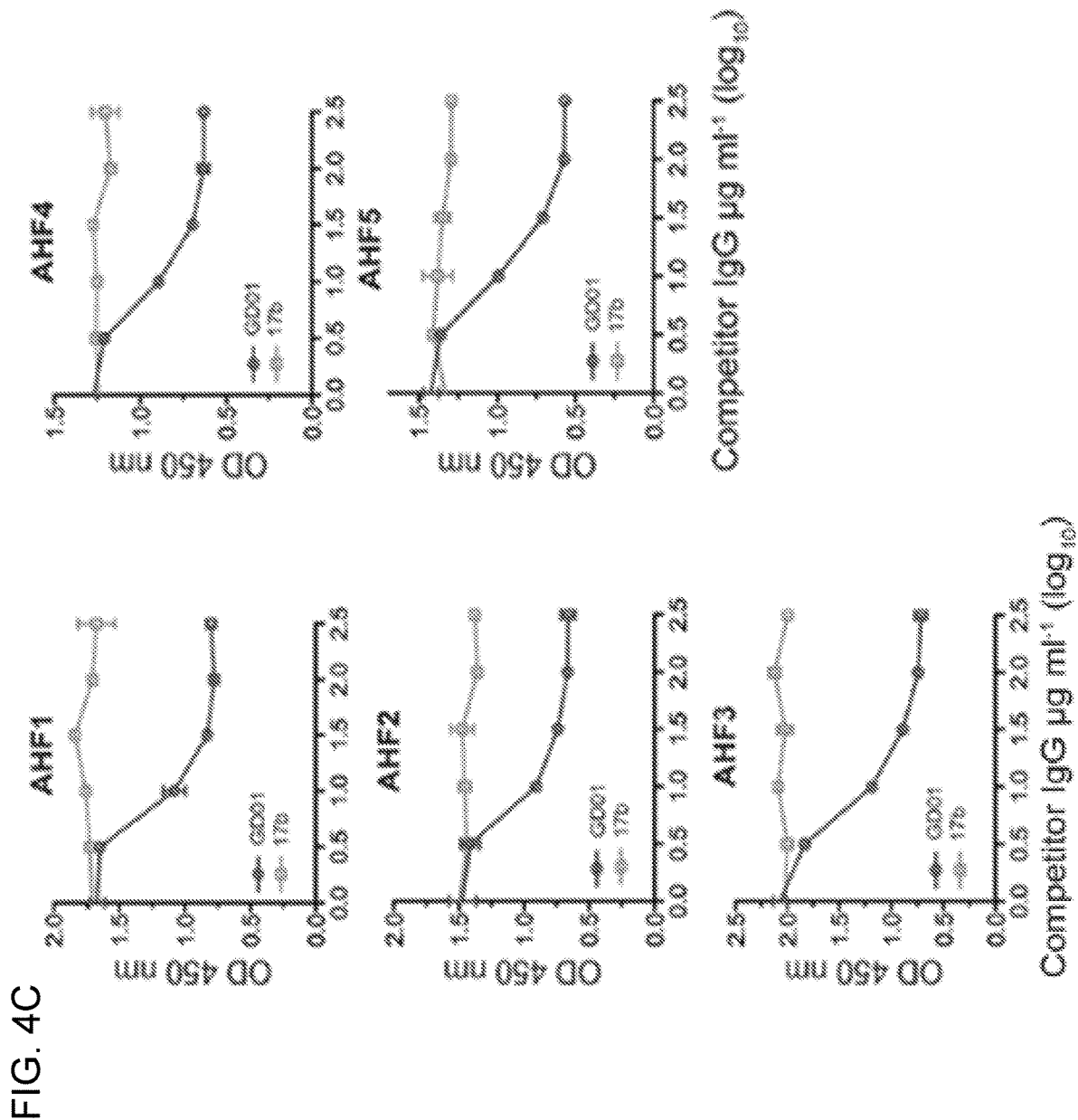

FIGS. 4A-4C show that the GP1 Tyr211-TfR1 pocket is an antibody target. FIG. 4A depicts a comparison of JUNV GP1 interaction with GD01 and MACV GP1 interaction with TfR1. Left panel: Ribbon diagram of JUNV GP1 with GD01 CDR H3 residues 97 to 100a shown as sticks. Residues labeled with an asterisk are mutated in the JUNV GP1$_{mut}$ construct. The refined $2F_o$-$F_c$ electron density at 1 σ for antibody segment is shown. Right panel: Ribbon diagram of MACV GP1 with TfR1 βII-2 strand residues 209 to 212 shown as sticks (from PDB ID: 3KAS[12]). The refined $2F_o$-$F_c$ electron density at 1 σ for receptor segment is shown. FIG. 4B are a set of graphs depicting AHF survivor IgG binding to JUNV GP1 or JUNV GP1$_{mut}$. ELISA of AHF survivor IgG binding to plates coated with JUNV GP1 or JUNV GP1$_{mut}$. Lujo virus (LUJV) GP1 coated wells were included as a control. The pre-determined neutralization titer of each survivor is shown between parentheses. Error bars indicate standard deviation. FIG. 4C shows a set of graphs depicting competition of JUNV infection (Argentine Hemorrhagic Fever, AHF) survivor IgG with GD01 for binding of JUNV GP1. Competition ELISA: GD01 or 17b competitor IgG was added at increasing concentrations to plates coated with JUNV GP1, and the indicated AHF survivor IgG were added at fixed concentrations. Survivor IgG that bound to the plate was detected using a secondary anti-human HRP-conjugated antibody. Error bars indicate standard deviation.

Figure 5A:
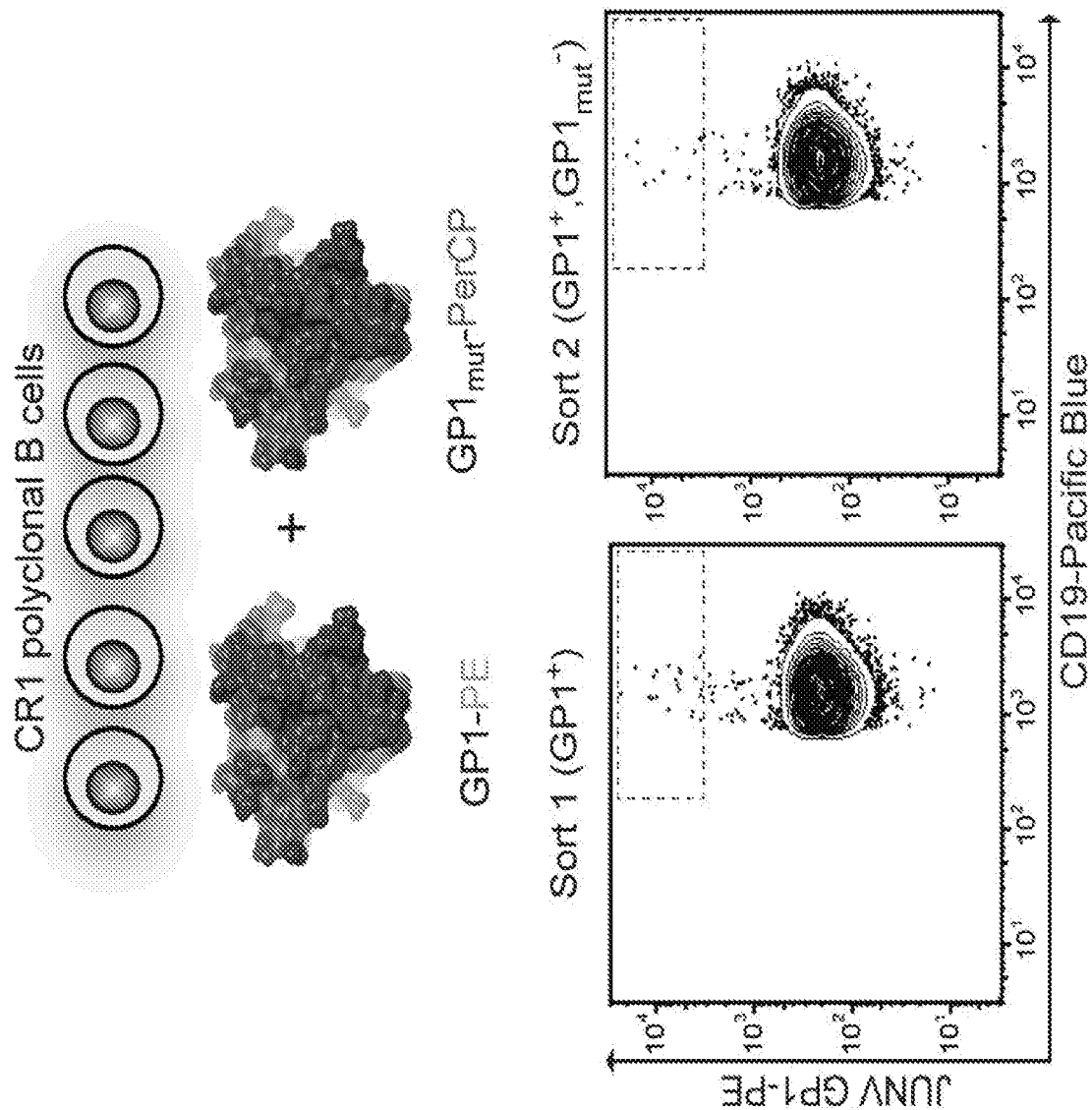
Figure 5B:
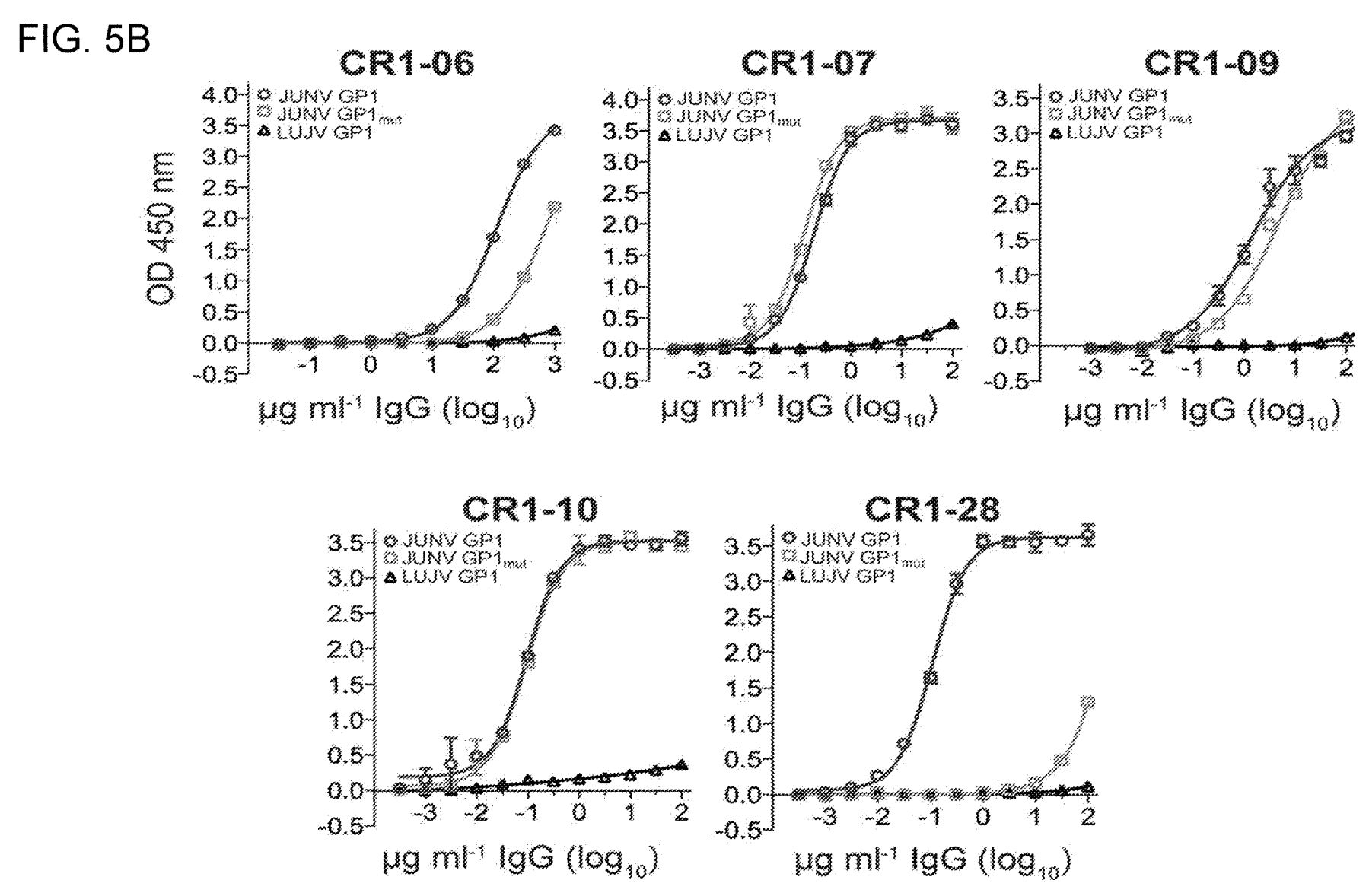
Figure 5C:
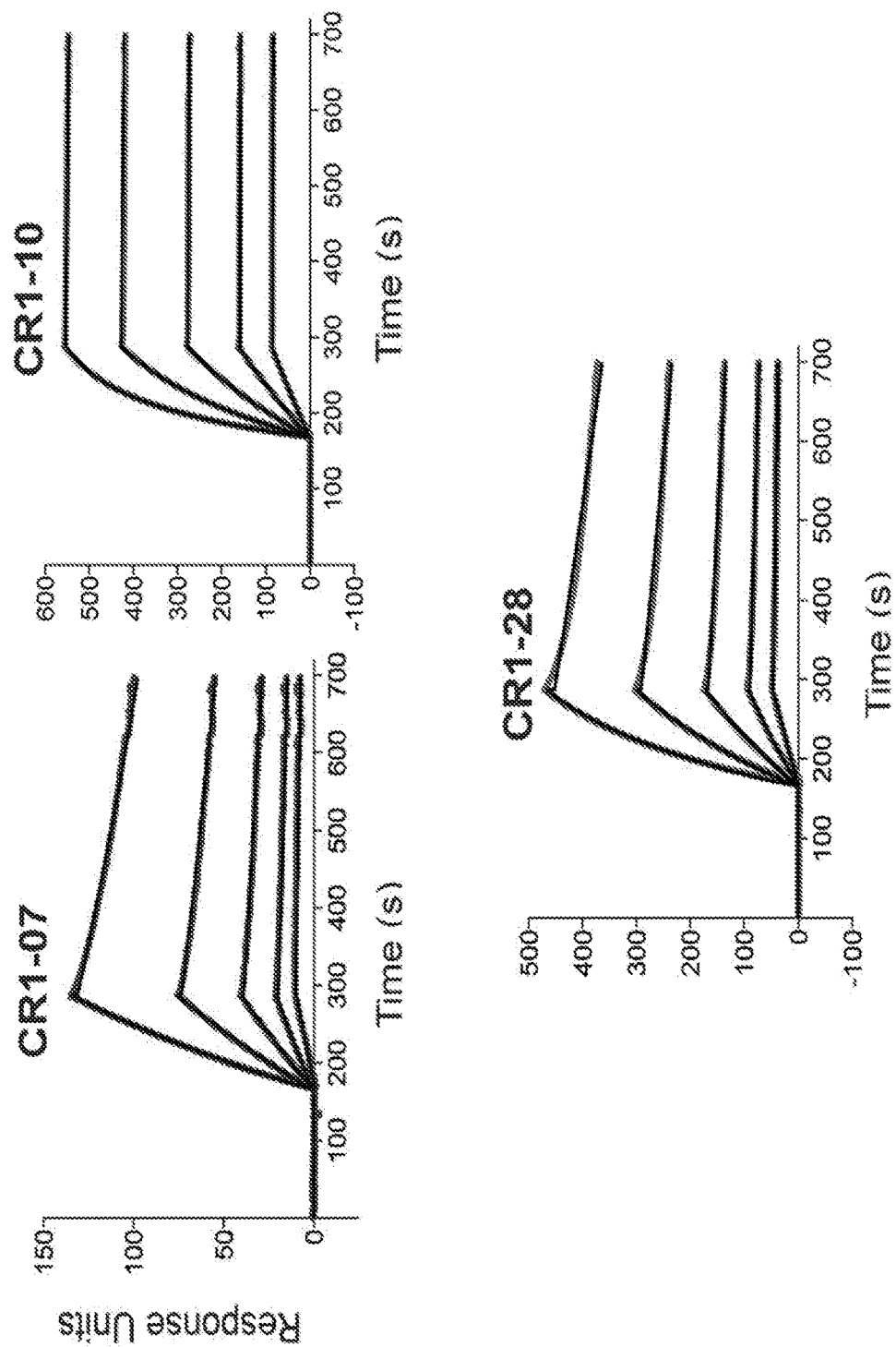
Figures 5D, 5E:
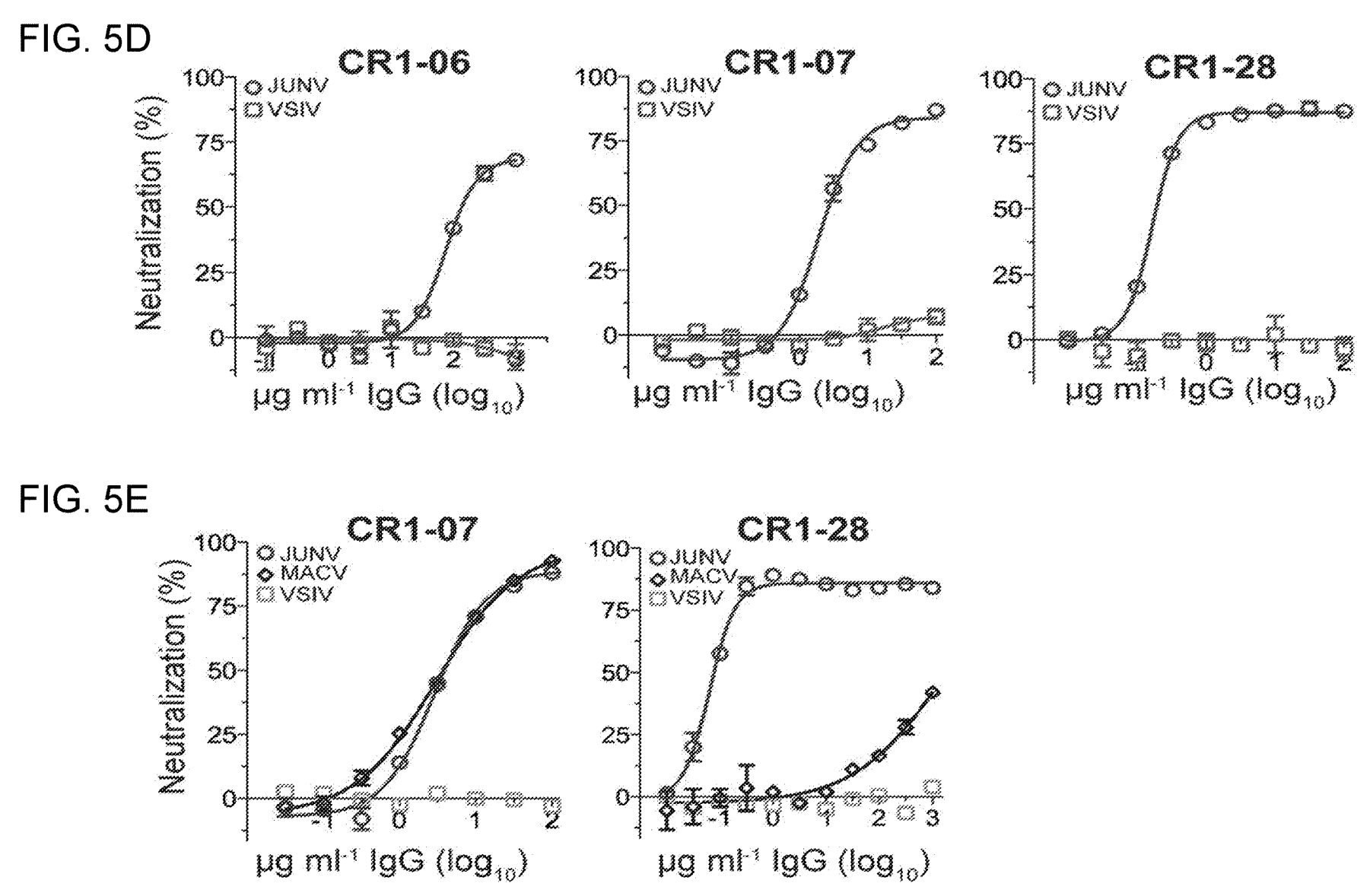

FIGS. 5A-5E show that single B-cell sorting identified JUNV GP1-reactive antibodies. FIG. 5A is a schematic of an experiment to identify JUNV GP1-specific antibodies. PBMCs from CR1 were mixed with fluorescently labeled GP1, or GP1 and GP1$_{mut}$ (Tyr211$_{TfR1}$ pocket mutant). Right panel shows a FACS density plot for memory B cells that stained positive for GP1 (Sort 1), or positive for GP1, but negative for GP1$_{mut}$ (Sort 2). The approximate location of the sorting gate is shown in dashed lines. CD19 is a B-cell marker. PE and PerCP are fluorophores. FIG. 5B are graphs showing ELISA data for the indicated identified monoclonal antibodies binding to JUNV GP1 or GP1$_{mut}$. LUJV GP1 is a control. FIG. 5C are graphs showing kinetic analysis of binding for the Fabs of the indicated antibodies to immobilized JUNV GP1 as measured by SPR. CR1-07, CR1-10, and CR1-28 bind GP1 with affinities of 86.2 nM, 45 pM, 5.3 nM, respectively. Binding of monomeric Fabs for CR1-06 and CR1-09 to GP1 could not be detected (because of low affinity, data not shown). FIG. 5D depicts neutralization profiles of the indicated antibodies for GFP-expressing JUNV pseudotypes (entry levels measured by FACS). CR1-09 did not neutralize JUNV and CR1-10 poorly neutralized JUNV (data not shown). FIG. 5E depicts neutralization profiles of CR1-07 and CR1-28 IgG of JUNV and MACV pseudotypes. VSIV pseudotypes are a control.

Figures 6A, 6B:
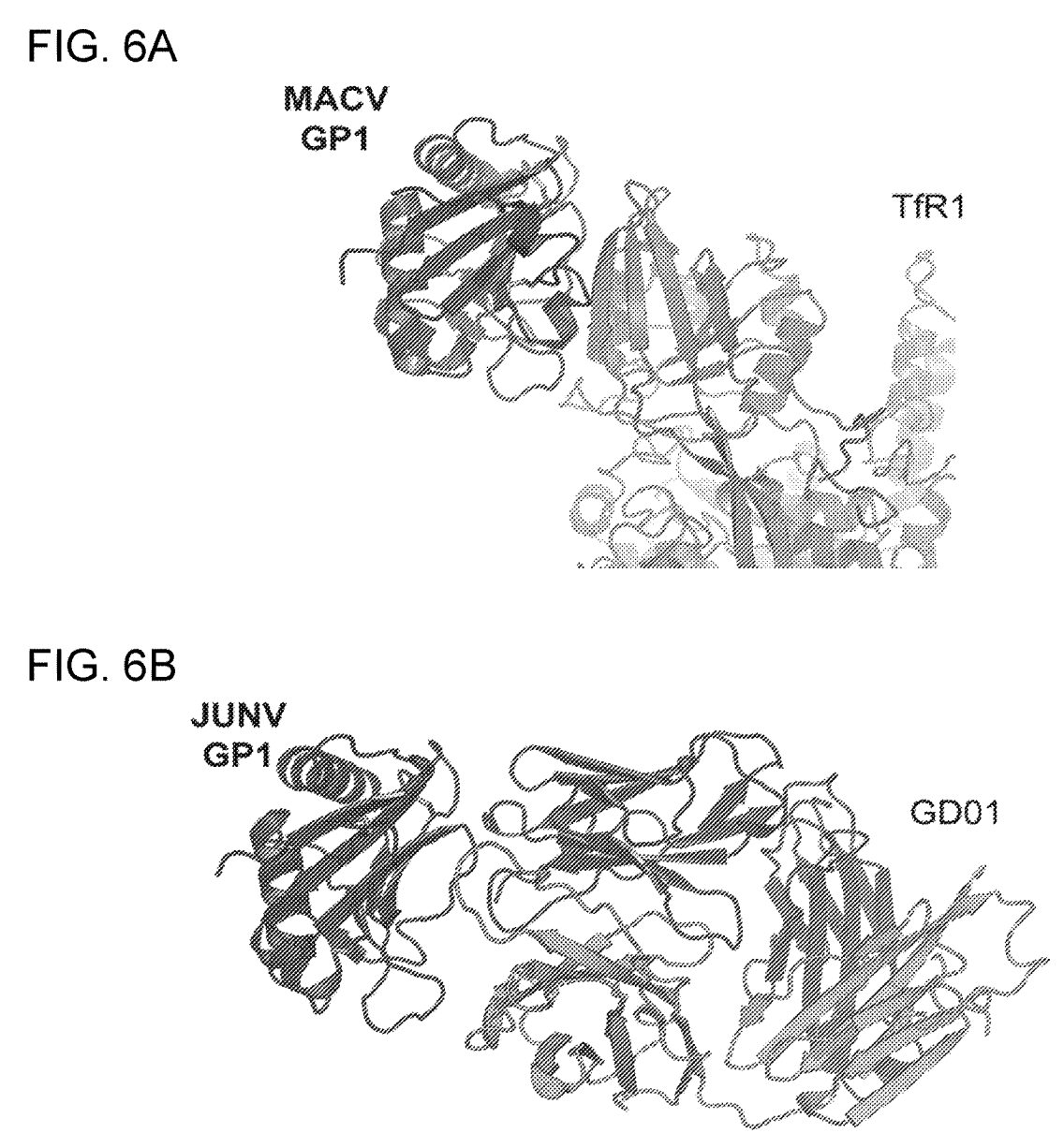
Figure 6C:
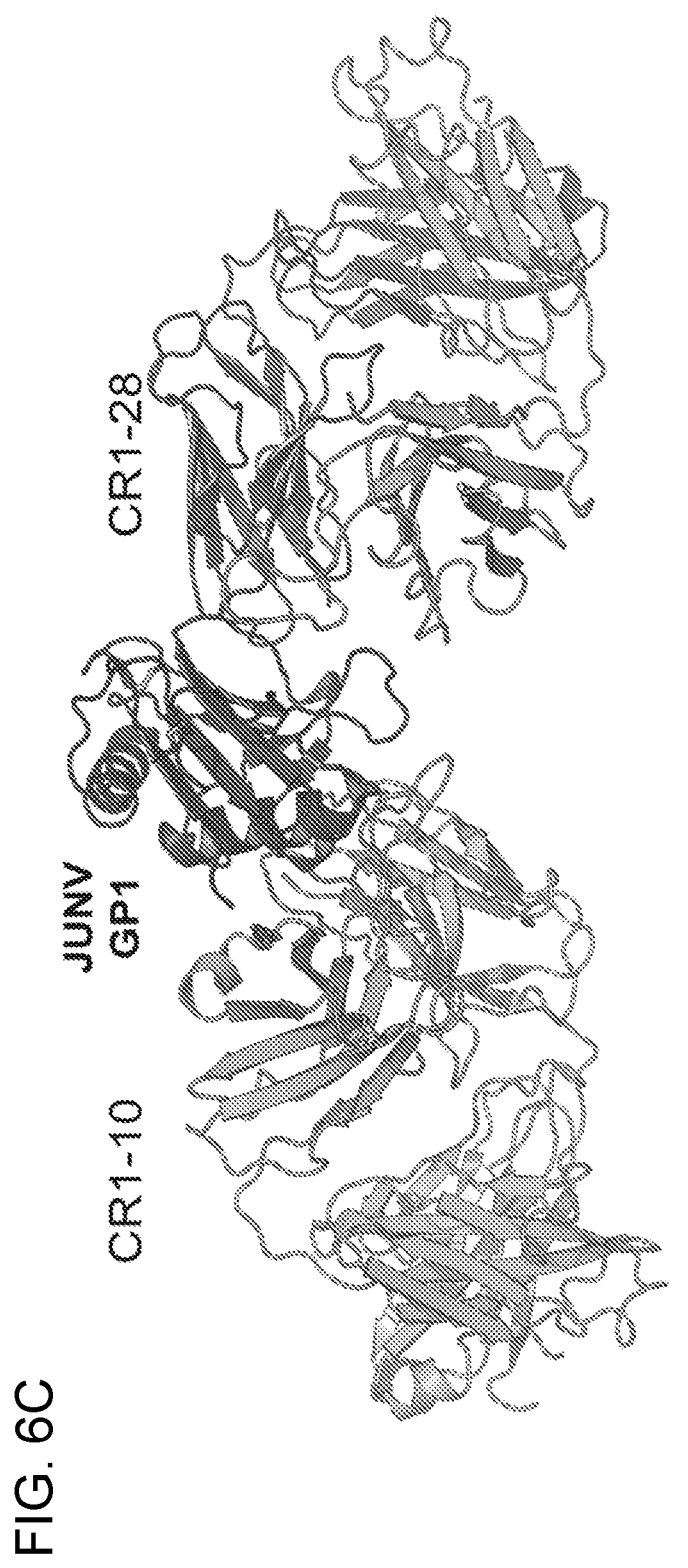
Figure 6D:
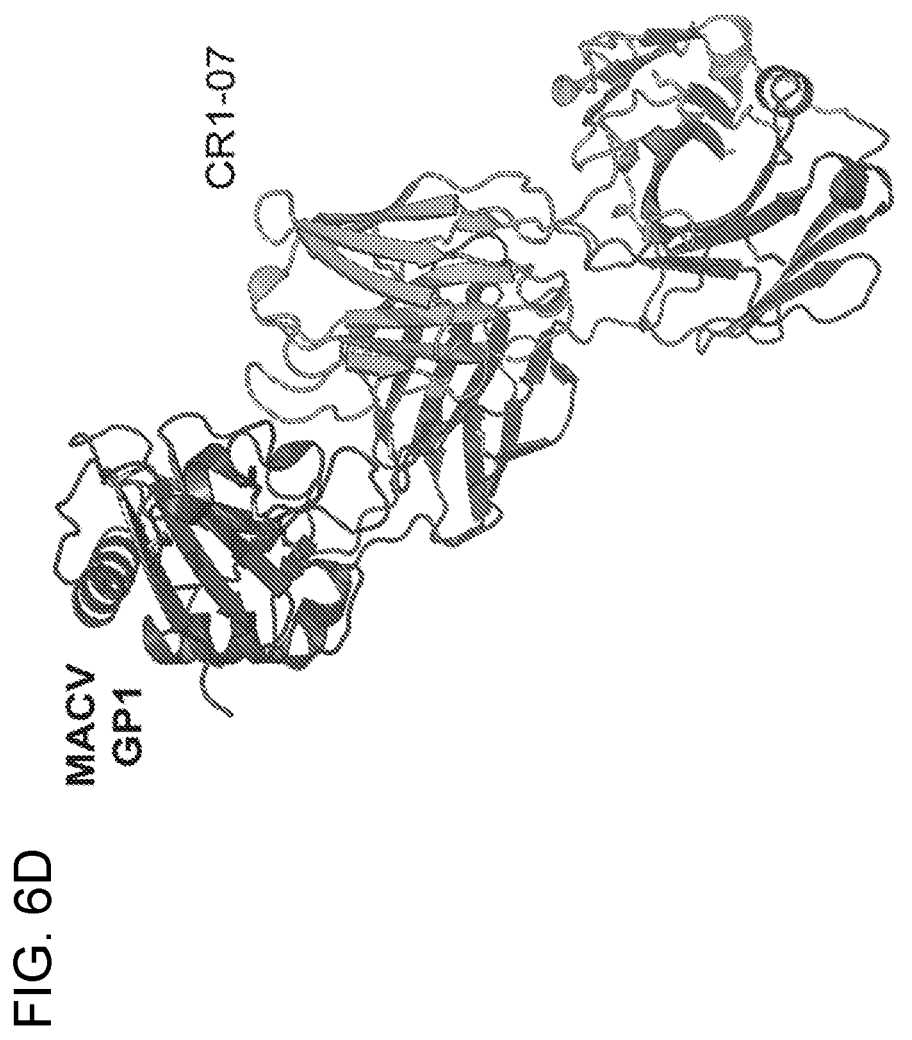

FIGS. 6A-6D depict structures of GP1 complexes. FIG. 6A is a ribbon diagram of MACV GP1 (left in diagram) bound to TfR1 (right in diagram). PDB 3KAS. FIG. 6B is a ribbon diagram of JUNV GP1 (left in diagram) bound to the Fab of a murine neutralizing antibody (GD01). PDB 5EN2. FIG. 6C is a ribbon diagram of JUNV GP1 (middle of diagram) bound to the Fabs of novel fully human neutralizing antibodies CR1-28 (right of diagram) and CR1-10 (left of diagram). FIG. 6D is a ribbon diagram of MACV GP1 (top of diagram) bound to the Fab of novel cross-neutralizing human antibody CR1-07 that has activity against MACV and JUNV. All potent neutralizing antibodies studied thus far bind the receptor-binding surface of GP1. (GD01, CR1-28, CR1-07 or CR1-10).

Figure 7:
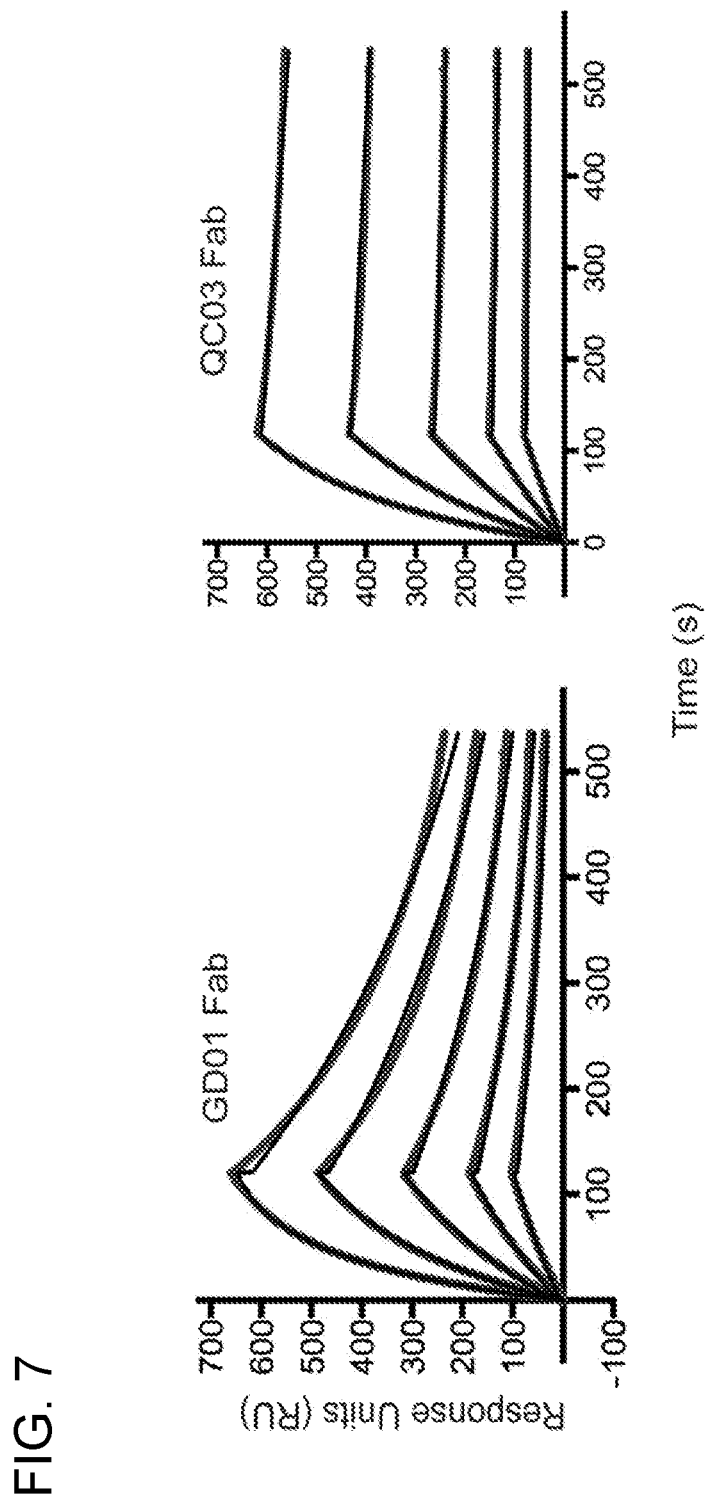

FIG. 7 presents graphs depicting high affinity GD01 and QC03 binding to JUNV GP1. Biotinylated JUNV GP1 was immobilized on the surface of a streptavidin-coated sensor chip. GD01 (left panel) or QC03 (right panel) were passed at 100, 50, 25, 12.5, and 6.25 nM over the sensor chip with regeneration between steps for multi-cycle kinetic analysis. All injections were carried out in duplicate. The recorded sensograms (one of the duplicates) and the fitted curves, calculated using a 1:1 Langmuir binding model, are shown. The recorded sensograms essentially superimpose on the fitted curves. The estimated $K_D$ for GD01 Fab and QC03 Fab for binding to JUNV GP1 are 12.5 and 1.5 nM, respectively. Binding constants are summarized in Table 1.

Figures 8D, 8E:
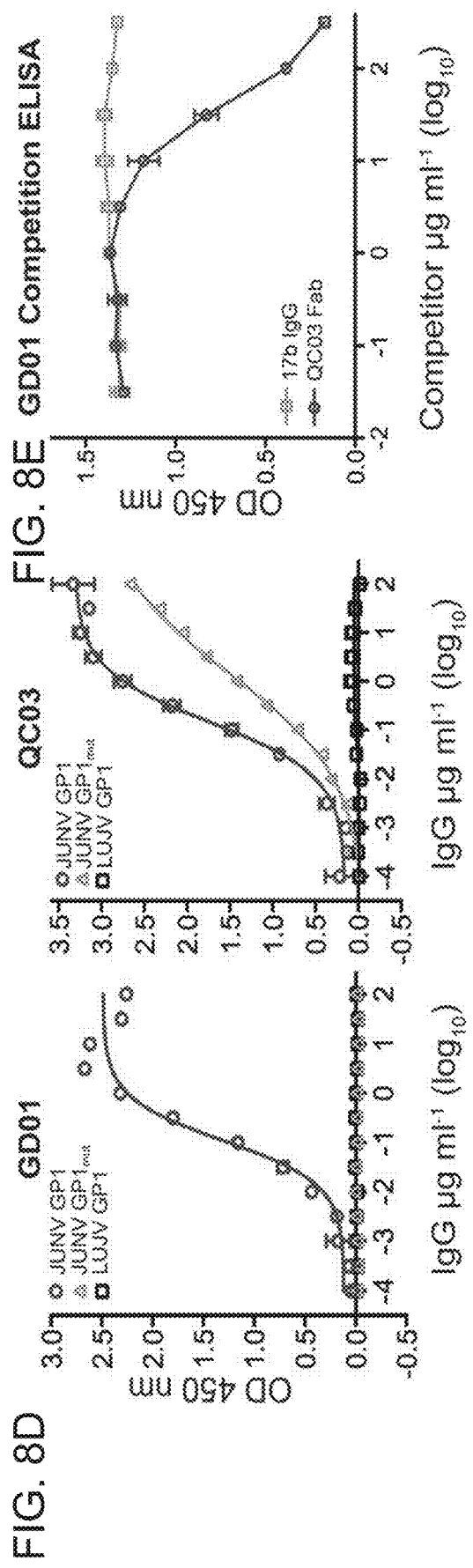

FIGS. 8A-8E depict GP1 sequences of New World hemorrhagic fever arenaviruses and design of receptor-binding site mutant. FIG. 8A is sequence alignment of JUNV GP1 (residues 1-127 and 129-151 of SEQ ID NO: 30) with the corresponding residues of the GP1 proteins of the New World mammarenaviruses MACV (SEQ ID NO: 31), TCRV (SEQ ID NO: 32), GTOV (SEQ ID NO: 33), SABV (SEQ ID NO: 34), and CHAPV (SEQ ID NO: 35). Empty circles indicate JUNV GP1 residues predicted to only contact TfR1, half-filled circles indicate JUNV GP1 residues only contacted by GD01, and filled circles indicate JUNV GP1 residues that are both predicted to contact TfR1 and interact with GD01. Tree diagrams indicate sites of N-linked glycosylation in JUNV GP1. Conserved cysteines and sites of N-linked glycosylation are highlighted in yellow and grey, respectively. The asterisk indicates the site of attachment of a conserved glycan contacted by GD01. FIG. 8B depicts a surface representation of JUNV GP1. The predicted TfR1 footprint is shown, and the Tyr211$_{TfR1}$ pocket is circled. The sites of the substitutions introduced to generate the GP1$_{mut}$ construct are shown in within the circle. FIG. 8C is a size exclusion chromatography profile of JUNV GP1 (solid line) and JUNV GP1$_{mut}$ (dashed lines). Both proteins elute at a similar retention volume when passed over a size exclusion column. The trace shown is for each protein after the nickel affinity purification step and removal of the His6 tag (SEQ ID NO: 26). FIG. 8D are graphs showing ELISA binding data. ELISA binding of GD01 IgG to plates coated with JUNV GP1 or JUNV GP1$_{mut}$ (Left panel). ELISA binding of QC03 IgG to plates coated with JUNV GP1 or JUNV GP1$_{mut}$ (Right panel). LUJV GP1 is a control. Error bars indicate standard deviation. FIG. 8E is a graph depicting GD01 competition ELISA results. QC03 Fab or 17b competitor IgG were added at increasing concentrations to plates coated with JUNV GP1, and GD01 IgG was added at fixed concentrations. GD01 IgG that bound to the plate was detected using a secondary anti-mouse Fc HRP-conjugated antibody. Error bars indicate standard deviation.

Figure 9C:
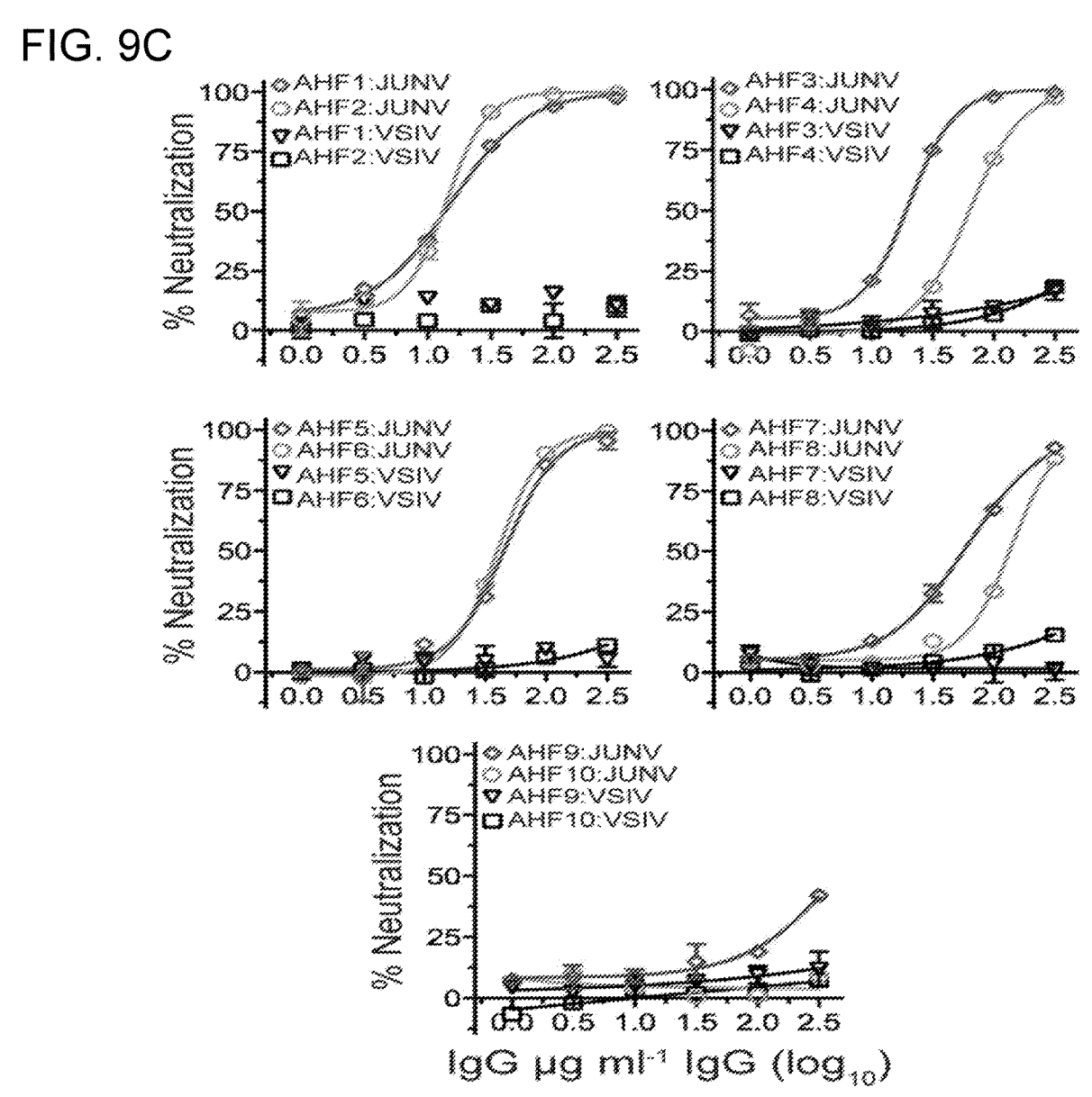
Figure 9D:
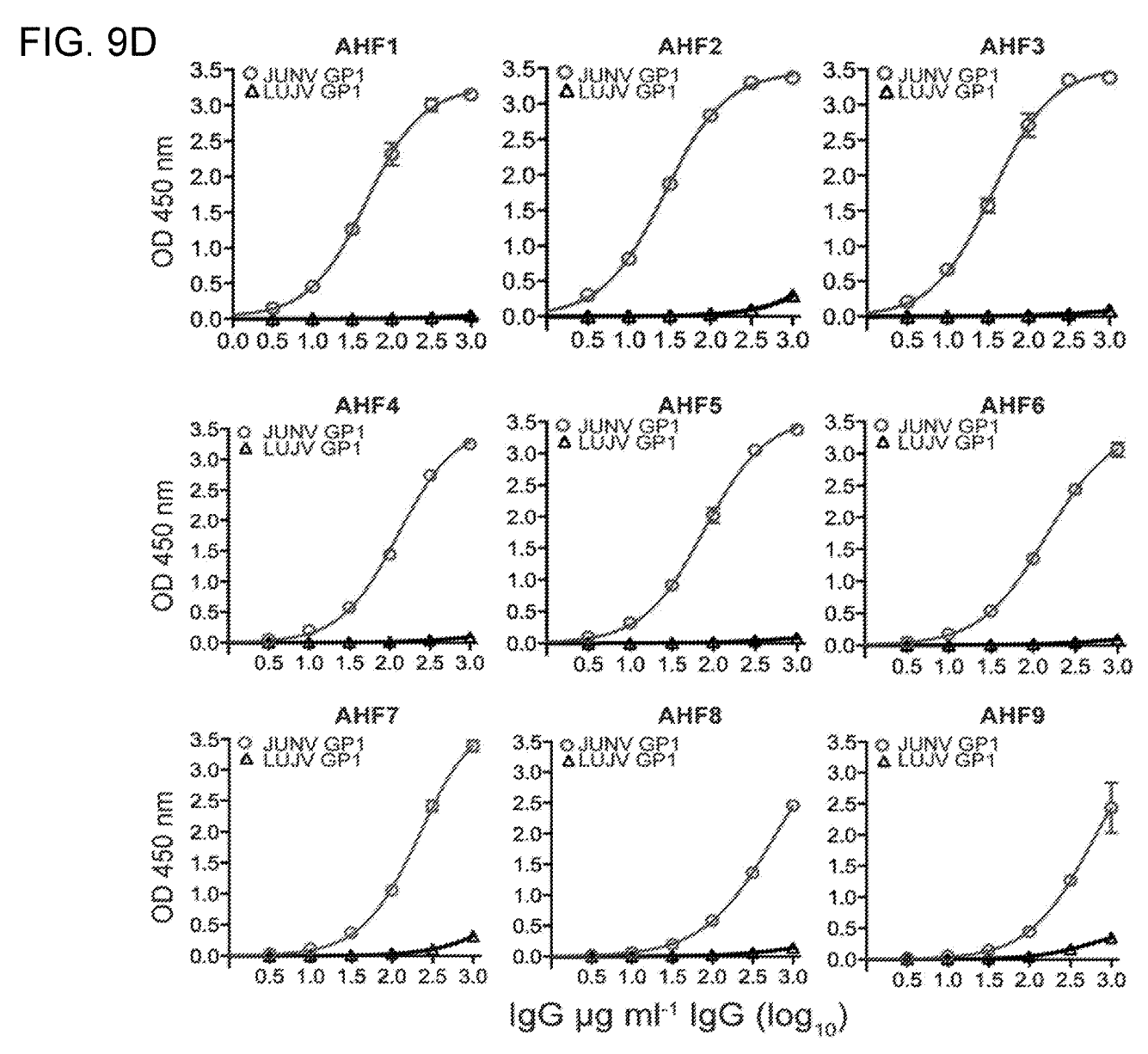

FIGS. 9A-9D show that Survivor plasma contains GP1-directed antibodies, related to FIG. 4. FIG. 9A is a list of pre-determined neutralization titers for survivor plasma samples AHF1 through AHF10. PRNT$_{80}$=plaque neutralization reduction of 80%: N.T.=no titer. FIG. 9B are graphs showing data for HEK293T cells challenged with JUNV pseudotype after pre-incubation with purified IgG for the indicated survivor samples (Left panel). Entry levels were measured by FACS for GFP expression. ELISA data of the indicated survivor IgG samples with JUNV GP1 coated plates (Right panel). LUJV GP1 coated plates are included as a control. Error bars indicate standard deviation. FIG. 9C presents graphs showing HEK293T cells challenged with JUNV pseudotype after pre-incubation with purified IgG for the indicated survivor samples, with entry levels measured as in FIG. 9B. VSIV pseudotype virus is included as a control. FIG. 9D are graphs showing ELISA data of the indicated survivor IgG samples with JUNV GP1 coated plates. LUJV GP1 is included as a control. Error bars indicated standard deviation.

Figure 10:
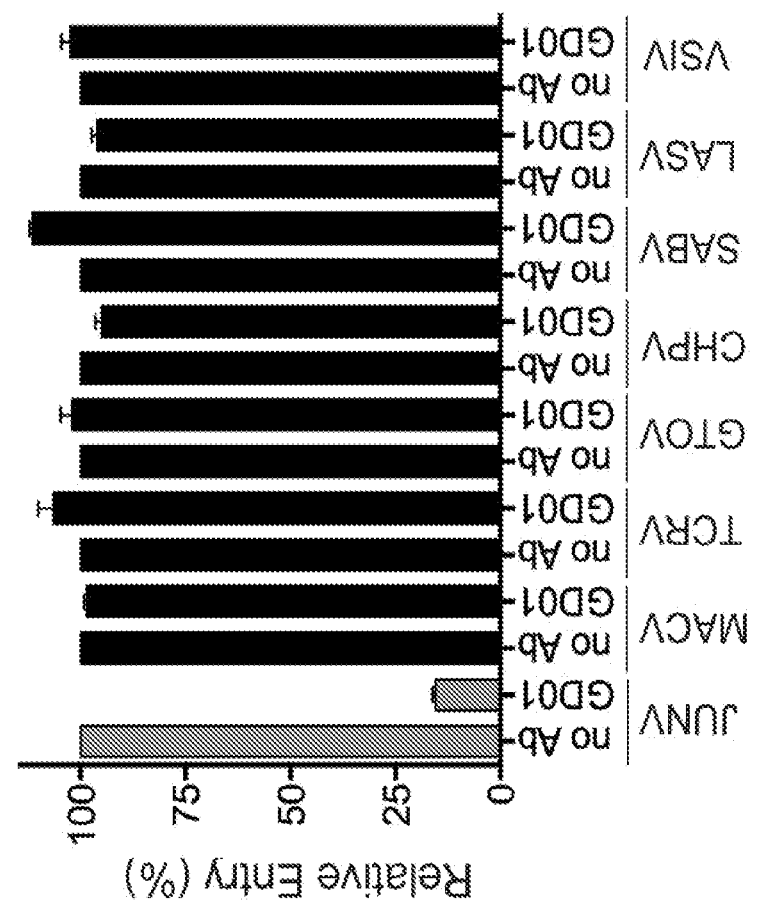

FIG. 10 is a bar graph depicting that GD01 does not neutralize the other New World hemorrhagic fever mammarenaviruses. GD01 was incubated at 100 μg/ml with JUNV, MACV, GTOV, SABV, CHAPV, Tacaribe virus (TCRV) pseudoviruses, or LASV or VSIV control pseudoviruses for 30 minutes. 293T cells were then challenged for 3 hr. Entry levels were measured by FACS for GFP expression 48 hr later, and normalized to levels in the absence of antibody ('No Ab', set at 100%). Error bars indicate standard deviation.

The atomic coordinates of the protein structure of a CR1-10/JUNV/CR1-28 complex are deposited in the Protein Data Bank (PDB) under Accession No. PDB ID 5W1K. The atomic coordinates of the protein structure of a MACV/CR1-07 complex are deposited in the Protein Data Bank (PDB) under Accession No. PDB ID 5W1M. The PDB file for JUNV GP1 bound to GD01 is available at Protein Data Bank Accession No. PDB ID 5EN2. The PDB file for MACV bound to transferrin is available at Protein Data Bank Accession No. PDB ID 3KAS. The atomic coordinates of the protein structure of an unliganded Fab fragment of CR1-07 is deposited at Protein Database (PDB) ID 5W1G. The entire contents of the protein structural data and atomic coordinates of these deposits are incorporated herein.

DETAILED DESCRIPTION OF THE INVENTION

The invention provides compositions and methods for treating or preventing arenavirus infection, as well as methods for the discovery or identification of therapeutic agents useful for inhibiting arenavirus infection. As described herein, the structure of the JUNV surface glycoprotein receptor-binding subunit (GP1) bound to a neutralizing monoclonal antibody was determined. The antibody engages the GP1 site that binds transferrin receptor 1 (TfR1)—the host cell surface receptor for all New World hemorrhagic fever arenaviruses—and mimics an important receptor contact. The invention is based, at least in part, on the discovery that the GP1 receptor-binding site (RBS) with which the New World hemorrhagic fever arenaviruses engage their obligate cell surface receptor, TfR1, is readily accessible to neutralizing antibodies. Several enveloped RNA viruses cause human viral hemorrhagic fevers, but passive immunotherapy has been rigorously shown to be effective in humans only for the treatment of JUNV infection. Without being bound by theory, it is proposed that RBS accessibility explains the effectiveness of convalescent-phase plasma therapy against JUNV. It is proposed that this functionally conserved epitope is a potential target for therapeutics and vaccines to limit infection by all New World hemorrhagic fever arenaviruses and also antibodies with cross-neutralizing activity against various viruses within the group. Thus, deploying and adapting this approach has the potential to limit outbreaks of the New World mammarenaviruses which depend on TfR1 for cellular entry, including the related arenaviruses MACV, GTOV, CHAPV, and SBAV.

Arenaviruses

Arenaviruses are enveloped viruses that carry single-stranded, bi-segmented RNA genomes. They include viruses found in captive alethinophidian snakes (the reptarenaviruses) and viruses that circulate mostly in rodents (the mammarenaviruses) (Radoshitzky et al., 2015). The arenaviruses are divided into two groups—'Old World' and 'New World'—based on their serology and geographic distribution. They cause acute human viral hemorrhagic fevers with high case fatality rates (Paessler and Walker, 2013). The pathogenic Old World arenaviruses include Lassa (LASV) and Lujo (LUJV) viruses (Briese et al., 2009; Charrel and de Lamballerie, 2003). The New World arenaviruses include Junin (JUNV), Machupo (MACV), Guanarito (GTOV), and Sabia (SBAV) viruses, which respectively cause Argentine (AHF), Bolivian, Venezuelan, and "Brazilian" hemorrhagic fever (Charrel and de Lamballerie, 2003; Oldstone, 2002; Salas et al., 1991). The most recently described member, Chapare virus (CHPV), was isolated from a small outbreak in Bolivia from 2003 to 2004 (Delgado et al., 2008). All cause severe human disease associated with hemorrhage and hemodynamic shock. Argentine hemorrhagic fever (AHF) is unique among viral hemorrhagic fevers because infusion of polyclonal neutralizing antibody-containing immune plasma derived from survivors ('passive immunity') is a well-established means of treating acute human infection (Maiztegui et al., 1979; Ruggiero et al., 1986). When provided within 8 days of illness, it decreases the case fatality rate from 15-30% to less than 1% (Maiztegui et al., 1979; Ruggiero et al., 1986). For it to be effective, the immune plasma has to be administered in defined doses of neutralizing activity (Enria et al., 1984). Without being bound by theory, this indicates that antibody-mediated virus neutralization is its main mode of action.

Arenavirus Surface Envelope Glycoprotein (GPC)

The arenavirus surface envelope glycoprotein (GPC) is the target of neutralizing antibodies. GPC comprises three non-covalently associated polypeptides; the stable signal peptide (SSP), GP1, and GP2 (Burri et al., 2012). GP1 binds cellular receptors, and GP2 contains a transmembrane segment and promotes fusion of the viral and host cell membranes. The ubiquitously expressed iron-uptake protein TfR1 is a cellular receptor for all New World hemorrhagic fever arenaviruses (Helguera et al., 2012; Radoshitzky et al., 2007). TfR1 orthologs from the natural hosts of all tested clade B New World arenaviruses are receptors for their corresponding virus, but only the New World arenaviruses that cause human disease bind human TfR1 (Choe et al., 2011).

Previously the structure of a MACV GP1-TfR1 complex was determined (Abraham et al., 2010). MACV GP1 binds TfR1 through an extensive network of contacts with the lateral surface of the apical domain of TfR1. Sequence comparison for the five New World hemorrhagic fever arenavirus GP1s show these to be complementary to the same TfR1 surface. A pocket on GP1 that accepts a tyrosine on the βII-2 strand of the TfR1 apical domain ($Tyr211_{TfR1}$) is a central feature of the GP1 receptor-binding site (RBS) (Abraham et al., 2010). This tyrosine is present on all the TfR1 orthologs that support entry of New World arenaviruses and is an important determinant of host specificity (Abraham et al., 2009; Radoshitzky et al., 2008).

Arenavirus Neutralizing Antibodies

GD01-AG02 (GD01) and QC03-BF11 (QC03) are antibodies that were generated in mice by immunization with inactivated JUNV (Sanchez et al., 1989). They belong to a small group of described monoclonal antibodies that neutralize JUNV, and they are active against infectious virus (Sanchez et al., 1989). However, their epitopes have not previously been characterized. As described herein, the X-ray crystal structure of JUNV GP1 complexed with the antigen-binding fragment (Fab) of GD01 was determined to understand how antibodies neutralize JUNV. The structure reveals that the antibody and receptor have similar modes of GP1 recognition and that the antibody's complementarity-determining region (CDR) H3 mimics the $Tyr211_{TfR1}$ receptor contact. GD01 and QC03 compete for the same GP1 surface. Without being bound by theory, this indicates that both antibodies neutralize the virus by a similar mechanism. It is further shown that survivor immune plasma with neutralizing activity contains antibodies that target the Tyr211 TfR1 pocket and GP1 RBS. The GP1 RBS is thus an accessible target for therapeutics and vaccines to limit infection caused by this important group of emerging human pathogens.

Therapeutic Methods

The methods and compositions provided herein can be used to treat or prevent an arenavirus infection. The methods and compositions provided herein can generate or enhance an immune response in a subject against an arenavirus infection. In general, arenavirus GP1 polypeptides and/or antibodies specific to arenavirus GP1 polypeptides described herein can be administered therapeutically and/or prophylactically to simulate an immune response specific for arenavirus GP1 antigen. The methods include administering an immunologically effective amount of an immunogenic GP1 polypeptide provided herein, and/or an immunologically effective amount of an antibody provided herein (e.g., CR1-07, CR1-28) to an individual in a physiologically acceptable carrier. In certain embodiments, the serum or plasma of an arenavirus immune survivor is used to treat or prevent the infection of another or different species of arenavirus.

The present invention provides methods of treating or preventing an arenavirus infection (e.g., a New World arenavirus infection), and/or disorders or symptoms thereof, which comprise administering a therapeutically effective amount of an anti-arenavirus GP1 agent as described herein (e.g., CR1-07, CR1-28, and/or a compound that specifically binds the TfR1 RBS of GP1), to a subject (e.g., a mammal such as a human). Thus, one embodiment is a method of treating a subject suffering from or susceptible to an arenavirus infection, disease or symptom thereof (e.g., viral hemorrhagic fever). The method includes the step of administering to the mammal a therapeutic amount of an anti-GP1 agent (e.g., anti-GP1 antibody) sufficient to treat the infection, disease or symptom thereof, under conditions such that the infection, disease or disorder is treated.

The present invention also provides methods of treating or preventing an arenavirus infection (e.g., a New World arenavirus infection), and/or disorders or symptoms thereof, which comprise administering a therapeutically effective amount of an immunogenic composition or vaccine as described herein (e.g., comprising a polypeptide comprising the TfR1 RBS of GP1), to a subject (e.g., a mammal such as a human). Thus, one embodiment is a method of preventing an arenavirus infection in a subject susceptible to an arenavirus infection, disease or symptom thereof (e.g., viral hemorrhagic fever). The method includes the step of administering to the mammal a prophylactic amount of an immunogenic GP1 polypeptide (e.g., comprising the TfR1 RBS of GP1) sufficient to prevent the infection, disease or symptom thereof, under conditions such that the infection, disease or disorder is prevent.

Treatment will be suitably administered to subjects, particularly humans, suffering from, having, susceptible to, or at risk for an arenavirus infection, disease or symptom thereof. Determination of those subjects "at risk" can be made by any objective or subjective determination by a diagnostic test or opinion of a subject or health care provider (e.g., genetic test, enzyme or protein marker (such as levels of S100 ligands), family history, and the like). The methods herein also include administering to the subject (including a subject identified as in need of such treatment) an effective amount of an anti-arenavirus GP1 antibody, an immunogenic composition or vaccine as described herein. Identifying a subject in need of such treatment can be in the judgment of a subject or a health care professional and can be subjective (e.g. opinion) or objective (e.g. measurable by a test or diagnostic method).

In some aspects, the invention features methods of treating or preventing an arenavirus arenavirus infection or arenavirus-associated disease or condition (e.g., hemorrhagic fever) in a subject, the methods comprising administering to the subject an effective amount of a composition comprising an anti-arenavirus agent (e.g., an anti-GP1 antibody or therapeutic vaccine as described herein). Optionally, an anti-arenavirus therapeutic of the invention (e.g., an anti-GP1 antibody or therapeutic vaccine as described herein) may be administered in combination with one or more of any other standard anti-arenavirus therapies (see e.g., Vela et al., 2012). For example, an anti-GP1 antibody or therapeutic vaccine as described herein may be administered in combination with other antibodies or antibody cocktails with antiviral activity (including e.g., immune plasma), in combination with a vaccine (including e.g., a therapeutic vaccine), or in combination with a drug with anti-arenavirus activity (Ribavirin). Methods for administering combination therapies (e.g., concurrently or otherwise) are known to the skilled artisan and are described for example in Remington's Pharmaceutical Sciences by E. W. Martin.

Antibodies

As reported herein, antibodies that specifically bind arenavirus GP1 are useful in therapeutic methods. For example, antibodies that inhibit or target the binding of transferrin receptor 1 (TfR1) to glycoprotein 1 (GP1), are particularly useful in the methods of the invention. In particular embodiments, the invention provides methods of using anti-GP1 antibodies for the treatment or prevention of arenavirus infection and/or hemorrhagic disease. Exemplary anti-GP1 antibodies include one or more of GD01, CR1-28, and CR1-07, and antibodies obtained or isolated from survivors of arenavirus infection (e.g., from blood, serum, or plasma).

Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of an intact antibody, clear more rapidly from the circulation, and may have less non-specific tissue binding than an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake. See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In various embodiments, an antibody that binds arenavirus GP1 is monoclonal. Alternatively, the anti-arenavirus GP1 antibody is a polyclonal antibody. In various embodiments, the antibody that binds arenavirus GP1 is obtained from the serum or plasma of an arenavirus immune survivor. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')2" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing soluble polypeptides, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding human arenavirus GP1 or immunogenic fragments thereof, can be provided to the host in a delivery vehicle that is taken up by immune cells of the host. The cells will in turn express the human arenavirus GP1 thereby generating an immunogenic response in the host. Alternatively, nucleic acid sequences encoding human arenavirus GP1 or immunogenic fragments thereof can be expressed in cells in vitro, followed by isolation of the human arenavirus GP1 and administration of the arenavirus GP1 to a suitable host in which antibodies are raised.

Alternatively, antibodies against arenavirus GP1 may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Pharmaceutical Compositions

The present invention features compositions useful for treating or preventing arenavirus infection in a subject. The methods include administering an immunologically effective amount of a polypeptide provided herein, and/or an immunologically effective amount of an antibody provided herein to an individual in a physiologically acceptable carrier. In some embodiments, the composition comprises an anti-GP1 agent, such as an anti-GP1 antibody, or fragment thereof, as described herein. In other embodiments, the composition comprises an immunogenic GP1 polypeptide, such as a polypeptide comprising the TfR1 RBS of GP1, or fragment thereof, as described herein.

Typically, the carrier or excipient for the immunogenic composition or vaccine provided herein is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions ensuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, and the like. Such methods also include administering an adjuvant, such as an oil-in-water emulsion, a saponin, a cholesterol, a phospholipid, a CpG, a polysaccharide, variants thereof, and a combination thereof, with the composition of the invention. Optionally, a formulation for prophylactic administration also contains one or more adjuvants for enhancing the immune response to the GP1 polypeptide antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

The administration of a composition comprising an anti-arenavirus agent herein (e.g., anti-GP1) for the treatment or prevention of an arenavirus infection or arenavirus-associated disease or condition (e.g., hemorrhagic fever) may be by any suitable means that results in a concentration of the therapeutic that, combined with other components, is effective in ameliorating, reducing, or stabilizing the disease symptoms in a subject. The composition may be administered systemically, for example, formulated in a pharmaceutically-acceptable buffer such as physiological saline. Preferable routes of administration include, for example, subcutaneous, intravenous, intraperitoneally, intramuscular, intrathecal, or intradermal injections that provide continuous, sustained levels of the agent in the patient. The amount of the therapeutic agent to be administered varies depending upon the manner of administration, the age and body weight of the patient, and with the clinical symptoms of the arenavirus infection or disease. Generally, amounts will be in the range of those used for other agents used in the treatment of cardiac dysfunction, although in certain instances lower amounts will be needed because of the increased specificity of the agent. A composition is administered at a dosage that ameliorates or decreases effects of the arenavirus infection or disease (e.g., hemorrhagic fever and symptoms thereof) as determined by a method known to one skilled in the art.

The therapeutic or prophylactic composition may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, intrathecally, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the heart; (v) formulations that allow for convenient dosing, such that doses are administered, for example, once every one or two weeks; and (vi) formulations that target a disease using carriers or chemical derivatives to deliver the therapeutic agent to a particular cell type. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, intrathecal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a cardiac dysfunction or disease, the composition may include suitable parenterally acceptable carriers and/or excipients. The active therapeutic agent(s) (e.g., an anti-GP1 agent described herein) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic (i.e., an anti-GP1 antibody herein) is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Methods of Identifying Agents that Inhibit Arenavirus GP1 Binding to Transferrin Receptor In Silico Drug Design The present invention permits the use of virtual design techniques (i.e., computer modeling or "in silico") to design, select, and synthesize compounds capable of specifically binding arenavirus GP1, in particular, GP1-mediated cell attachment. In turn, these compounds may be effective in the treatment of an arenavirus infection or arenavirus-associated disease, such as hemorrhagic fever.

In addition to the more traditional sources of test compounds, computer modeling and searching technologies permit the rational selection of test compounds by utilizing structural information from the ligand binding sites and functional antibody binding sites (e.g., binding sites of arenavirus-inhibitory antibodies) on proteins of the present invention (e.g., arenavirus GP1). Such rational selection of compounds may decrease the number of compounds that may need to be screened to identify a therapeutic candidate compound. In various embodiments, the functional antibody binding site of GP1 is a TfR1 binding site. In some embodiments, the functional site on arenavirus GP1 comprises any one or more of amino acid residues 87-235 (JUNV numbering) of arenavirus GP1 or a corresponding region of an arenavirus GP1 (see, e.g., FIG. 8A). Important motifs include the pocket in the arenavirus GP1 that interacts with residue Tyr211 in transferrin receptor 1, which includes Junin virus GP1 residues Serine 111, Aspartate 113, Isoleucine 115, and Lysine 216, and the analogous residues in the GP1 proteins of MACV, GTOV, SBAV, CHPV, TCRV, and WWAV; and GP1 loop 3 (residues 113-124, JUNV numbering) and GP1 loop 7 (residues 166-174, JUNV numbering), and their respective counterparts in MACV, GTOV, SBAV, CHPV.

Knowledge of the protein sequences of the present invention may allow for generation of models of their binding sites that may be used to screen for potential agent(s) that bind to the binding sites. This process may be accomplished with the skills known in the art. One approach involves generating a sequence alignment of the protein sequence to a template (derived from the crystal structures or NMR-based model of a similar protein(s)), conversion of the amino acid structures and refining the model by molecular mechanics and visual examination. If a strong sequence alignment may not be obtained, then a model may also be generated by building models of the hydrophobic helices. Mutational data that point towards contact residues may also be used to position the helices relative to each other so that these contacts are achieved. During this process, docking of the known ligands into the binding site cavity within the helices may also be used to help position the helices by developing interactions that may stabilize the binding of the ligand. The model may be completed by refinement using molecular mechanics and loop building using standard homology modeling techniques. General information regarding modeling may be found in Schoneberg, T. et. al., *Molecular and Cellular Endocrinology*, 151:181-193 (1999), Flower, D., *Biochim Biophys Acta,* 1422, 207-234 (1999), and Sexton, P. M., *Curr. Opin. Drug Discovery and Development,* 2, 440-448 (1999).

Once the model is completed, it may be used in conjunction with one of several computer programs to narrow the number of compounds to be screened, e.g., the DOCK program (UCSF Molecular Design Institute, San Francisco, Calif. 94143) or FLEXX (Tripos Inc., MO). One may also screen databases of commercial and/or proprietary compounds for steric fit and rough electrostatic complementarity to the binding site. In one embodiment, the docking program is ZDOCK (Pierce et al., *Bioinformatics.* 2014 Jun. 15; 30(12):1771-3). In another embodiment, the docking program is AutoDock Vina (Trott et al., *Journal of Computational Chemistry* 31 (2010) 455-461).

In Silico Screening of Compounds

In one aspect, the invention provides means to carry out virtual screening of compounds using the disclosed atomic coordinates or coordinates derived therefrom. The atomic coordinates of the three-dimensional structure elucidated by the invention are input into a computer so that images of the structure and various parameters are shown on the display. The resultant data are input into a virtual compound library. Since a virtual compound library is contained in a virtual screening software, the above-described data may be input into such a software. Compounds may be searched for, using a three-dimensional structure database of virtual or non-virtual compounds, such as MDDR (Prous Science, Spain).

The potential interactions of a compound may be analyzed prior to its actual synthesis and testing by the use of computer modeling techniques. If the theoretical structure of the given compound suggests insufficient interactions with arenavirus GP1, synthesis and testing of the compound may be obviated. However, if computer modeling indicates sufficient interactions, the molecule may then be synthesized and tested for its ability to regulate arenavirus GP1, using various methods described herein and/or that are known to a person skilled in the art.

Compounds may be computationally evaluated and designed by means of a series of steps in which chemical entities or fragments are screened and selected for their ability to bind with individual binding sites or combinations thereof (e.g., P0, P+1, P−1) or other areas of arenavirus GP1.

One skilled in the art may use any of several methods to screen chemical entities or fragments for their ability to bind to arenavirus GP1 and more particularly with the specific binding sites or functional sites described herein (e.g., Protein Data Bank Accession No. PDB ID 5EN2, 3KAS, or those deposited under Protein Data Bank Accession No. PDB ID 5W1K and Protein Data Bank Accession No. PDB ID 5W1M. Sequences of arenavirus GP1, may also be threaded onto the protein backbone of an arenavirus GP1 crystal structure, with side chain positions optimized using methods known in the art. The resulting structural models may then be used to discover chemical entities or fragments that regulate arenavirus GP1 via in silico docking. The process may begin by visual inspection of, for example, the functional site on the computer screen based on the arenavirus GP1 coordinates presented in Protein Data Bank PDB ID 5EN2, 3KAS, or those deposited under Protein Data Bank Accession No. PDB ID 5W1K and Protein Data Bank Accession No. PDB ID 5W1M. Selected fragments or chemical entities may then be positioned in a variety of orientations, or docked, within a binding site of arenavirus GP1. Docking may be accomplished using software such as QUANTA™, SYBYL™ followed by energy minimization and molecular dynamics with molecular mechanics force-fields softwares, such as CHARMM™ and AIVIBER™.

Specialized computer programs may also assist in the process of selecting fragments or chemical entities. These include, but are not limited to, GRID™ (Goodford, P. J., J. Med. Chem., 28, 849-857 (1985)); MCSS™ (Miranker, A. and M. Karplus, "Proteins: Structure, Function and Genetics, 11, 29-34 (1991)); (3) AUTODOCK™ (Goodsell, D. S. and A. J. Olsen, Proteins: Structure, Function, and Genetics, 8, 195-202 (1990; DOCK™ (Kuntz, I. D. et al., J. Mol. Biol., 161, pp. 269-288 (1982)); GLIDE™ (Schrodinger Inc.); FLEXX™ (Tripos Inc); (7) GOLD™ (Jones et al., J. Mol. Biol., 245, 43-53, 1995).

Once suitable chemical entities or fragments have been selected, they may be assembled in silico or synthesized into a single compound. Chemical syntheses may be carried out by methods known in the art. In silico assembly may proceed by visual inspection of the relationship of the fragments to each other on the three-dimensional image displayed on a computer screen in relation to the structure coordinates of arenavirus GP1. This may be followed by manual model building using softwares such as QUANTA™ or SYBYL™.

Useful programs for connecting the individual chemical entities or fragments include the following: CAVEAT™ (Bartlett, P. A. et al, Royal Chem. Soc., 78, 182-196 (1989)); 3D Database systems such as MACCS-3D™ (MDL Information Systems, San Leandro, Calif.); and HOOK™ (Molecular Simulations, Burlington, Mass.). In addition to building a compound in a step-wise fashion as described above, compounds may be designed as a whole or "de novo" using an empty active site or optionally including some portion(s) of a known compound. Such methods include, but are not limited to, LUDI™ (Bohm, H.-J., J. Com R. Aid. Molec. Design, 6, pp. 61-78 (1992)); LEGEND™ (Nishibata, Y. and A. Itai, Tetrahedron, 47, p. 8985 (1991)), and LEAP-FROG™ (Tripos Inc., St. Louis, Mo.).

Once a compound has been designed or selected, the molecular interactions or affinity with which that compound may bind arenavirus GP1 may be tested and optimized by computational evaluation. For example, a compound may demonstrate a relatively small difference in energy between its bound and unbound states (i.e., a small deformation energy of binding). A compound may interact with arenavirus GP1 in more than one conformation that is similar in overall binding energy. In those cases, the deformation energy of binding is taken to be the difference between the energy of the unbound compound and the average energy of the conformations observed.

A compound that is designed or selected may be further computationally optimized so that in its bound state it may lack repulsive electrostatic interactions. Such interactions include repulsive charge-charge, dipole-dipole, and charge-dipole interactions. The sum of all electrostatic interactions between the compound and arenavirus GP1, may make a neutral or favorable contribution to the enthalpy of binding. Software programs to evaluate compound deformation energy and electrostatic interaction include, e.g., Gaussian 92™ (M. J. Frisch, Gaussian, Inc., Pittsburgh, Pa.); AIV-IBER™ (P. A. Kollman, University of California at San Francisco, Calif.); QUANTA/CHARMM™ (Molecular Simulations, Inc., Burlington, Mass.); and Insight II/Discover™ (Biosysm Technologies Inc., San Diego, Calif.).

Once a compound has been optimally selected or designed, substitutions may be made in some of its atoms or side groups in order to improve or modify its binding properties. Initial substitutions may be conservative, i.e., the replacement group will have approximately the same size, shape, hydrophobicity and charge as the original group. Such substituted compounds may then be analyzed for efficiency of fit to arenavirus GP1 by software programs similar to those described.

Crystallographic Evaluation of Chemical Entities for Binding to Arenavirus GP1

The invention allows one skilled in the art to study the binding of compounds to arenavirus GP1 by exposing either individual compounds or mixtures of compounds (such as may be obtained from combinatorial libraries) into arenavirus GP1 crystals or, alternatively, by co-crystallization of the compounds of interest with arenavirus GP1, using methods known in the art, or those described in the Examples herein. Acquisition and analysis of X-ray diffraction data from these crystals may then be performed using standard methods. If a compound binds to arenavirus GP1 then positive difference electron density will be observed in the Fourier maps calculated using the X-ray diffraction intensities and phases obtained from the arenavirus GP1 model presented herein. Models of the chemical entities may then be built into the electron density using standard methods, and the resulting structures may be refined against the X-ray diffraction data, providing experimental data describing the interaction of the compounds of interest. Those skilled in the art may use these models to design compounds based either on purely structural data; or on combination of structural data, biological/chemical activity based structure-activity relationship, and in silico drug design.

The compounds that are thus designed or selected may further be tested in an in vitro, in vivo, or ex vivo assays to determine if they bind or neutralize arenavirus GP1. Such assays are known to one skilled in the art, including functional assays such as ELISA, gel filtration, immunoprecipitation, plasmon resonance, and the like.

Kits

The invention provides kits for the treatment or prevention of an arenavirus infection. In some embodiments, the kit includes a therapeutic or prophylactic composition containing an effective amount of an anti-GP1 agent (e.g., an anti-GP1 antibody) in unit dosage form. In other embodiments, the kit includes a therapeutic or prophylactic composition containing an effective amount of an immunogenic agent (e.g., a GP1 polypeptide) in unit dosage form. In some embodiments, the kit comprises a device (e.g., a nebulizer, metered-dose inhaler) for dispersal of the composition or a sterile container which contains a pharmaceutical composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a pharmaceutical composition of the invention is provided together with instructions for administering the pharmaceutical composition to a subject having or at risk of contracting or developing an arenavirus infection. The instructions will generally include information about the use of the composition for the treatment or prevention of an arenavirus infection. In other embodiments, the instructions include at least one of the following: description of the therapeutic/prophylactic agent; dosage schedule and administration for treatment or prevention of arenavirus infection or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1. The Structure of the Complex of JUNV GP1 with GD01 was Determined.

Because GP1 is expected to be the most membrane distal subunit of GP on the virion surface, GD01 and QC03 Fabs were tested for JUNV GP1-reactivity. QC03 and GD01 both bound JUNV GP1 with high affinity as measured by surface plasmon resonance (1.5 nM and 12.5 nM, respectively; FIG. 7 and Table 1).

TABLE 1

Binding rate constants of surface plasmon resonance analysis (FIG. 7).

| Analyte | Ligand | $k_a$ (1/Ms) | $k_d$ (1/s) | $K_D$ (M) |
| --- | --- | --- | --- | --- |
| GD01 Fab | JUNV GP1 | 2.08E5 | 2.61E−3 | 1.25E−8 |
| QC03 Fab | JUNV GP1 | 1.49E5 | 2.25E−4 | 1.51E−9 |

The structure of a GP1-neutralizing antibody complex was determined. A complex of JUNV GP1 with the GD01 Fab crystallized in space group P212121. Molecular replacement with MACV GP1 (Abraham et al., 2010) and an unrelated Fab (Aoki et al., 2009) as search models was used and the structure was refined with data extending to 1.8 Å (FIG. 1, and Table 2).

TABLE 2

Data collection and refinement statistics (molecular replacement) (FIG. 1).

| | JUNV GP1:GD01 |
| --- | --- |
| Data collection | |
| Cell dimensions | $P2_12_12_1$ |
| a, b, c (Å) | 52.1, 74.8, 177.6 |
| Resolution (Å) | 68.93 – 1.82 (1.92 – 1.82)* |
| $R_{merge}$ | 0.226 (1.418) |
| Mean I/σI | 6.7 (1.5) |
| Completeness (%) | 99.9 (99.9) |
| Redundancy | 5.9 (5.7) |
| Refinement | |
| Resolution (Å) | 68.93 – 1.82 |
| No. reflections | 63032 |
| $R_{work}/R_{free}$ | 0.181/0.224 (0.239/0.274) |
| No. atoms | 5473 |
| Protein | 4462 |
| Ligand/ion | 125 |
| Water | 886 |
| B-factors | |
| Protein | 21 |
| Ligand/ion | 59 |
| Water | 38 |
| R.m.s. deviations | |
| Bond lengths (Å) | 0.010 |
| Bond angles (°) | 1.06 |

One crystal was used to collect the dataset.
*Values in parentheses are for the highest-resolution shell.

Figure 2:
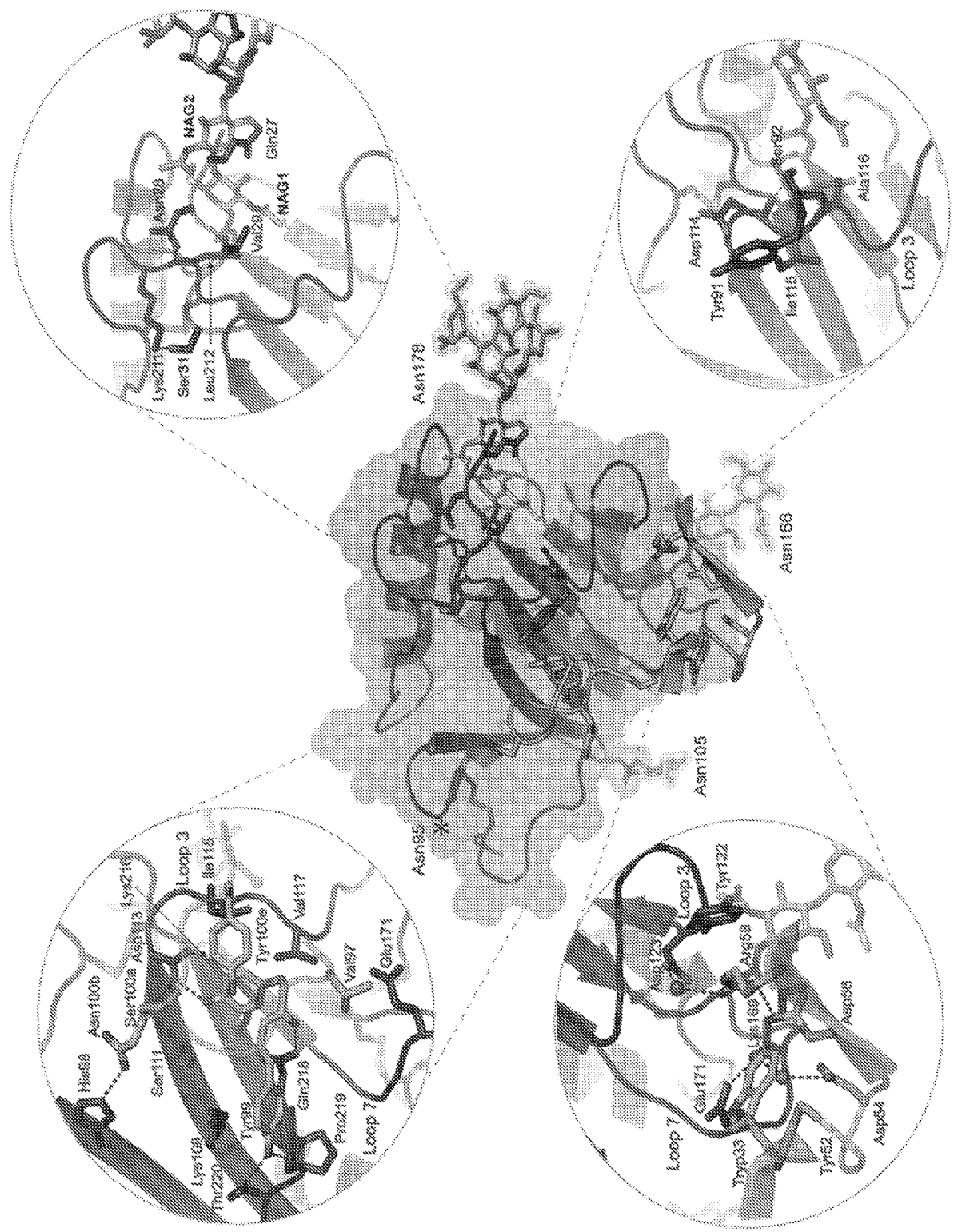

The interface of JUNV GP1 with GD01 includes contacts from heavy-chain CDRs 1, 2 and 3 and light-chain CDRs 1 and 3, with the bulk of the interactions focusing on GP1 loops 3 and 7 (FIG. 1). The tyrosine-rich CDR H3 projects into a shallow cavity created by the curvature of the central β-sheet and loop 3 (FIG. 2, left upper panel), which is sandwiched between the heavy-chain and light-chain CDRs. CDRs H1 and H2 form a network of polar interactions with GP1 loops 3 and 7 (FIG. 2, left lower panel), and CDR L1 contacts the glycan attached at GP1 Asn178 (FIG. 2, right upper panel). This glycan is conserved in the GP1 proteins of all New World hemorrhagic fever mammarenaviruses. CDR L3 provides additional contacts to the N-terminal side of GP1 loop 3 (FIG. 2, right lower panel).

Example 2. Neutralizing Anti-GP1 Antibody and TfR1 Receptor have a Shared Mode of GP1 Recognition JUNV GP1 is very similar to MACV GP1 (rmsd of 1.35 Å for Ca positions for residues 87-219 and 223-227), as expected from their sequences (48% identical for GP1 residues 87-235). However, there is a substantial difference in loop 10, in which MACV GP1 has a disulfide-linked insert with respect to JUNV (FIG. 3A, left panel). Because of this similarity, the JUNV GP1 and MACV GP1-TfR1 structures were superimposed to predict a TfR1 footprint on JUNV GP1 (FIG. 3A right panel and FIG. 3B). All but one of the 13 residues in that footprint are within the contact zone of the antibody, which includes a total of 15 residues (FIG. 8A).

When viewed from the perspective of GP1, the lateral surface of the TfR1 apical domain presents two parallel ridges—one formed by the edge of the αII-2 helix and the βII-6-βII-7a loop, and the other by the βII-2 strand (FIG. 3C). GP1 loop 3 fits between both ridges and crosses to the far side of the αII-2 helix. The antibody likewise presents two parallel ridges that accept GP1 loop 3—one from the heavy chain (parts of CDR H1, CDR H2, and CDR H3), and the other from the light chain (CDR L1 and CDR L3)—but closed off at one end by the C-terminal side of CDR H2. These two ridges superpose approximately onto the receptor βII-2 sheet and αII-2 helix ridges, respectively. The antibody thus resembles the receptor in the overall shape of its CDR surface.

Example 3. GD01 Tyr98 (Kabat) Fits into the Position Occupied in the GP1 Receptor-Glycoprotein Complex by TfR1 Tyr211

Close examination of the antibody-GP1 interface reveals that GD01 Tyr98 (Kabat numbering scheme) in CDR H3 fits precisely into the position occupied in the receptor-glycoprotein complex by $Tyr211_{TfR1}$, even though most of the other specific interactions are different in character (FIGS. 4A and 4B). For example, the contact MACV GP1 Ser113 forms with the hydroxyl group of $Tyr211_{TfR1}$ is replaced by a contact Asp113 in JUNV GP1 makes with the hydroxyl group of GD01 Tyr98. Another change at position 216, where lysine in JUNV GP1 replaces a threonine in MACV GP1, prevents the tyrosine side chain from reaching more deeply into the pocket. The orientation of Tyr98 in the GD01-GP1 complex probably is one that would be observed for $Tyr211_{TfR1}$ in an authentic JUNV GP1-TfR1 complex, with CDR H3 of the antibody mimicking an important receptor contact.

A modified JUNV GP1 (designated JUNV $GP1_{mut}$) was generated, in which the GP1 pocket that accepts $Tyr211_{TfR1}$ was occluded by substituting residues that line it with bulkier ones (S111W, I115Y, and V117Y; FIG. 8B). JUNV $GP1_{mut}$ expressed well in the supernatant of transfected HEK293T cells, and when purified eluted from a size exclusion column at the same retention volume as wild type GP1, indicating that this mutant protein is properly folded (FIG. 8C). As expected from the structure, GD01 did not bind JUNV $GP1_{mut}$ (FIG. 8D, left panel). QC03, another JUNV neutralizing antibody, did bind JUNV $GP1_{mut}$, but considerably more weakly than it did the WT protein (FIG. 8D, right panel), indicating that it likewise contacts the $Tyr211_{TfR1}$ pocket, but probably less centrally than does GD01. QC03 Fab competed with GD01 for binding to JUNV GP1, confirming that both GD01 and QC03 are RBS-directed antibodies (FIG. 8E). Without being bound to theory, it is hypothesized that both neutralizing antibodies neutralize JUNV by interfering with binding to the host cell receptor.

Example 4. AHF Survivor Plasma Contained RBS-Directed Antibodies

Because survivor plasma transfusion is a very effective treatment for AHF (Enria et al., 1984; Maiztegui et al., 1979), it was determined whether immune plasma samples used for passive immunity contained RBS-directed antibodies. Nine survivor plasma samples (AHF1 through 9) were obtained with neutralizing antibody titers ranging from 1:10,240 to 1:40, and a survivor plasma sample with no neutralizing activity at the time of collection (AHF10) was also obtained (FIGS. 9A-9D). Purified survivor IgG bound JUNV GP1, as measured by ELISA, with affinities that roughly correlated with their neutralizing activities (FIGS. 9A-9D).

Single B-cell sorting was used to identify JUNV GP1-reactive antibodies from the blood of a recipient of the live attenuated vaccine Candid #1 (the individual is referred to as Candid #1 Recipient 1, or CR1) (FIGS. 5A-5E). Five CR1 antibodies bound to JUNV GP1 by ELISA, and two antibodies, CR1-06 and CR1-28, bound to $GP1_{mut}$ less tightly than WT GP1 (FIG. 5B). Without being bound by theory, this may indicate that the pocket is part of their epitope. CR1-28 was identified from a sort that included a counter-selection step with $GP1_{mut}$ (Sort 1); the ELISA result therefore validates sensitivity of the platform to 'fish out' epitope specific antibodies. Fabs for three of the CR1 antibodies had high affinity for JUNV GP1 when measured by SPR (FIG. 5C), and three of the six antibodies neutralized JUNV pseudotypes (FIG. 5D). CR1-07 efficiently cross-neutralized MACV (FIG. 5E). CR1-28 at high concentrations (>100 µg/ml) also had activity against MACV.

Structures of GP1 complexes were determined for binding of the antibodies CR1-07, CR1-10, and CR1-28 isolated from single B-cell sorting to JUNV and MACV. The structure of MACV GP1 bound to TfR1 receptor (PDB 3KAS; see FIG. 6A) and the structure of JUNV GP1 bound to antibody GD01 (PDB 5EN2; see FIG. 6B) were determined. Structures of JUNV GP1 bound to CR1-28 and CR1-10 (FIG. 6C) and of CR1-07 bound to MACV GP1 (FIG. 6D) were determined. The JUNV GP1-CR1-28 co-crystal structure also included a poorly-neutralizing antibody (CR1-10) that does not bind the TfR1 receptor binding site in GP1. The structures revealed that CR1-28 neutralizes JUNV by targeting the Tyr211TfR1 pocket and also mimicking a contact made by $Tyr211_{TfR1}$ (this antibody is therefore like GD01), and also binding GP1 loop 3 and GP1 loop 7. The structures also revealed that CR1-07 cross-neutralizes MACV by targeting a small, entirely conserved patch of the RBS that is remote from $Tyr211_{TfR1}$ epitope but still includes GP1 loop 3 and loop 7. The structures thus define the GP1 TfR1 receptor binding site for potent neutralizing antibodies that can cross-neutralize different New World arenaviruses that bind the TfR1 receptor.

To determine if the $Tyr211_{TfR1}$ pocket is a target for antibodies in human immune plasma, survivor IgG was tested for binding to JUNV GP1 and $GP1_{mut}$. IgG purified from the plasma of AHF1 through AHF9 IgG bound JUNV $GP1_{mut}$ more weakly than they bound WT GP1 (FIG. 4B). The difference was less marked for lower activity AHF8 and AHF9 IgG. Survivor IgGs (particularly those with high neutralizing activity) therefore contained antibodies that bind the GP1 $Tyr211_{TfR1}$ pocket.

Although the $Tyr211_{TfR1}$ pocket is a central feature of the GP1 RBS, it is only a small part of the predicted TfR1 footprint (FIG. 8B). Some antibodies that recognize nearby sites in the large RBS, but not the pocket itself, may also have neutralizing activity. An example of one such antibody is CR1-07 (FIG. 6D). Because the GD01 footprint encompasses the entire GP1 RBS, the most potent survivor IgGs were tested for reactivity against the GD01 epitope using a competition ELISA. IgG isolated from the plasma of AHF1 through 5, but not a control antibody (17b), competed with GD01 for binding to JUNV GP1 (FIG. 4C). These data confirmed that the RBS epitope is a target for antibodies generated during natural human infection.

The lack of complete competition of GD01 with survivor IgGs in the ELISA shown in FIG. 4C indicates that antibodies binding epitopes other than the GP1 RBS are present in survivor plasma. While antibodies that target the RBS with reasonable affinity should, in principle, be neutralizing, non-neutralizing antibodies may bind other epitopes in GP1. Potential non-neutralizing epitopes include GP1 surfaces involved in oligomerization that are accessible on soluble GP1, but not accessible on functional, trimeric GPC on the virion surface. These non-neutralizing antibodies could have been generated against shed JUNV GP1; GP1 shedding has been described in acute infection by another arenavirus, LASV (Branco et al., 2010). Without being bound by theory, CR1-10, which binds the non-receptor binding face of GP1 (FIG. 6C), may be one such antibody.

Receptor mimicry is a recurring phenomenon in antibody neutralization of enveloped RNA viruses. Receptor-mimicking antibodies neutralize influenza viruses (Schmidt et al., 2015; Xu et al., 2013) and HIV-1 (Scheid et al., 2011; Zhou et al., 2010). The results here reinforce the concept that host receptor mimicry is a general mode of antibody neutralization for diverse families of viruses.

GD01 does not neutralize the other New World hemorrhagic fever arenaviruses (FIG. 10). In contrast, CR1-28 and CR1-07 have activity against MACV. Sequence differences in the GP1 RBS probably block binding to GD01 but preserve its interaction with TfR1, CR1-28, and CR1-07. These differences result in part from long-term co-adaptation of viruses with their natural rodent hosts, including an "arms race" between the various rodent TfR1 orthologs and the mammarenavirus GP1s (Demogines et al., 2013). The lateral edge and tip of the TfR1 apical domain (FIGS. 3A and 3C, right panels), a site engaged by all New World mammarenaviruses, is a "hot spot" for mutations with strong evidence of selective pressure in rodents (Demogines et al., 2013). Without being bound by theory, a large RBS may allow GP1 to tolerate variation in host receptor sequences in a virus-host arms race, but also leaves it exposed for immune recognition. Neutralizing antibodies targeting this site could then more readily select for viral escape mutations, and thus account for RBS diversity as New World mammarenaviruses circulate in their respective rodent hosts.

Because GD01 and TfR1 recognize GP1 similarly, the structure could serve as a template for in vitro or in silico design of antibodies that more faithfully mimic the receptor and neutralize some or all of the other viruses in this group. For example, the relatively prominent CDR H3 (17 residues) of GD01 projects substantially farther from the contact surface with GP1 than does the βII-2 strand of TfR1, and residues at its tip would collide with the MACV GP1-specific loop 10 insert (FIG. 4B). An engineered antibody with a similar contact surface but a shorter CDR H3 might in principle neutralize both JUNV and MACV. Interestingly, both CR1-28 and CR1-07 avoid MACV GP1 loop 10. Without being bound by theory, this in part explains their ability to cross-react with MACV.

A less accessible RBS might explain why treatment with convalescent phase survivor plasma may be less effective against other viral hemorrhagic fevers. In the GP of the filoviruses Ebola virus (EBOV) and Sudan virus, for example, the GP1 RBS is hidden beneath a heavily glycosylated mucin-like domain that contains both O-linked and N-linked carbohydrates and becomes exposed only after this domain has been cleaved by cathepsin in acidified endosomes (Chandran et al., 2005; Lee et al., 2008). Neutralizing antibodies that target other sites, such as the GP1-GP2 interface (which lies near the viral membrane), appear to have a larger role in limiting these infections (Dias et al., 2011; Murin et al., 2014). The GP1 RBS for another filovirus that causes human hemorrhagic fevers, Marburg virus (MARV), is more exposed, and antibodies binding this site may be more important in controlling infection by this virus (Flyak et al., 2015). A MARV neutralizing antibody that probably mimics a viral glycoprotein-receptor contact has been described (Flyak et al., 2015; Hashiguchi et al., 2015).

Like filoviruses, arenaviruses that are endemic to South America all lack adequate and rapidly scalable treatment options. Antibodies like GD01, CR1-28, and CR1-07 could eventually replace immune plasma in the treatment of AHF and perhaps of other New World hemorrhagic fevers. The findings described herein further indicate that a recombinant GP1 subunit-based immunization strategy, which focuses the immune response on the RBS by hiding other sites, has the potential to effectively protect against infection caused by these lethal agents.

The results described herein were obtained using the following materials and methods.

Cells and Plasmids

HEK293T (human embryonic kidney cells, ATCC CRL-1268) were maintained in Dulbecco's modified Eagle's medium (DMEM) supplemented with 10% (v/v) fetal bovine serum (FBS). $GnTI^{-/-}$ 293S cells were maintained in serum free medium (FreeStyle™ 293 Expression Medium, Life Technologies). GP-expressor plasmids for JUNV, MACV, GTOV, SABV, CHAPV, TCRV, and LASV, and an expressor plasmid for vesicular stomatitis virus (VSIV) G, have been previously described (Abraham et al., 2009; Radoshitzky et al., 2007) (Helguera et al., 2012). LUJV GP (GenBank: NC_023776.1) was synthesized as a codon-optimized gene for mammalian expression, and subcloned into the pCAGGS vector. Hybridomas producing monoclonal antibodies GD01 and QC03 (clones GD01-AG02 and QC03-BF11, respectively) (Sanchez et al., 1989) were obtained from the NIAID Biodefense and Emerging Infections (BEI) repository. These cells in Hybridoma-SFM expression medium (Life Technologies). The pHLSec vector (Aricescu et al., 2006) was used to express secreted glycoproteins.

Pseudotype Transduction

Pseudotypes were packaged in 293T cells by transfecting plasmids encoding murine leukemia virus gag/pol, the arenaviral GP, and the pQCXIX transduction vector (BD Biosciences) expressing eGFP in a 1:1:1 ratio, as previously described (Radoshitzky et al., 2007). Virus-containing culture supernatant was harvested 24 hr and 48 hr later. Supernatants were filtered through a 0.45 µm membrane, and pseudotypes were stored at −80° C. until later use. For antibody neutralization experiments, pseudotypes were pre-incubated with polyclonal IgG or monoclonal antibodies for 30 min at 37° C. The pseudotypes and antibody mixture were then added to cells, and the media changed with 10% (v/v) FBS-supplemented DMEM 3 hr post transduction. Entry levels were measured by flow cytometry 48 hr post transduction.

Protein Expression and Purification

To generate biotinylated proteins, JUNV GP1 (residues 87-235), MACV GP1 (residues 87-250), and LUJV GP1 (residues 59-217), were each subcloned along with an N-terminal His6-tag (SEQ ID NO: 26), followed by a Tobacco Etch Virus (TEV) protease site, a BirA ligase site (amino acids: GLNDIFEAQKIEWHE (SEQ ID NO: 27)), and a seven residue linker (amino acid sequence: GTGSGTG (SEQ ID NO: 28)), into the pHLSEC expression vector (Aricescu et al., 2006). JUNV $GP1_{mut}$, which encodes JUNV GP1 residues 87-235 and contains the S111W, I115Y and V117Y mutations was generated by site directed mutagenesis. Proteins were produced by transfection using linear polyethylenimine in HEK293T cells grown in suspension, and the proteins purified using nickel affinity chromatography. The His6-tag (SEQ ID NO: 26) was removed with TEV protease and reverse nickel-affinity purification, and then site specific biotinylation was performed with BirA ligase followed by size-exclusion chromatography on a Superdex 200 column (GE Healthcare Sciences) to remove free biotin. For crystallography, JUNV GP1 (residues 87-235) was subcloned with the addition of N-terminal His6-Tag (SEQ ID NO: 26), a TEV protease site, and a short linker (amino acids: SGSG (SEQ ID NO: 29)), into the pHLSEC vector. The protein was produced in $GnTI^{-/-}$ 293S cells grown in suspension and purified by nickel affinity chromatography, and the tag was removed with TEV digestion, reverse nickel-affinity purification, and size exclusion on a Superdex 200 column. GD01 and QC03 Fabs were produced using a Pierce™ Fab Preparation Kit (Thermo scientific) from Protein G Ultralink® Resin (Thermo scientific) following the manufacturer's protocol.

Surface Plasmon Resonance Binding Assays

Binding experiments were performed in duplicate with a Biacore 3000 (GE Health Care Sciences), using streptavidin coated sensor chips, and biotinylated JUNV GP1. Approximately 600-800 response units of biotinylated JUNV GP1 were captured onto the chips to avoid rebinding events. Experiments were carried out in HBS-EP (10 mM HEPES pH 7.5, 150 mM NaCl, 3 mM EDTA, and 0.005% P-20). GD01, QC03, CR1-07, CR1-10, and CR1-28 Fabs were passed over the surface at various concentrations, and GP1-Fab interactions were analyzed using multi-cycle kinetic analysis with 2 min association and 5 min dissociation phases with a flow rate of 50 μL/min. Between each cycle, the surface was regenerated with two 5 μl injections of 35 mM NaOH, 1.3 M NaCl at 100 μL/min, and 2 minute stabilization after regeneration. For analysis, injections over blank surfaces were subtracted from the data, and the data was fit using a 1:1 Langmuir binding model in the BiaEvaluation software (GE Health Care Sciences).

Data Collection and Structure Determination

The JUNV GP1-GD01 Fab complex crystallized in the P212121 space group. X-ray diffraction data were collected at wavelength of 0.9789 and temperature of 100° K at NE-CAT beam line ID-24C at the Advanced Photon Source (Argonne National Laboratory). Data were processed using MOSFLM (Leslie and Powell, 2007), and the structure of the complex was determined by molecular replacement with PHASER (McCoy et al., 2007) with MACV GP1 (PBD ID: 3KAS) (Abraham et al., 2010) and the 4F8 Fab (PDB ID: 3FMG) (Aoki et al., 2009) as search models. Electron density was observed for residues 87-227 for JUNV GP1, residues 1 to 213 with the exception of residues 128-132 in the GD01 HC, and residues 1 to 212 in the GD01 LC. We could form a ternary complex of JUNV GP1 bound to the Fabs of CR1-28 and CR1-10. This complex yielded crystals in space group P1211 that diffracted to 3.99 Å. We determined its structure using molecular replacement, and identified four copies of the complex in the asymmetric unit (ASU). We obtained crystals of a complex of a MACV GP1-CR1-07 in space group P42212 that diffracted to 3.9 Å. Initial molecular replacement searches with MACV GP1 (PDB 3KAS). We determined the structure of the unliganded CR1-07 Fab, and used these coordinates along with MACV GP1 as search models to solve the structure of the complex. The model includes 4 copies of the complex per ASU.

Sequence for the GD01 Fab was obtained using a previously described protocol for antibody gene recovery from the parent hybridoma (Fields et al., 2013), and performed iterative model building with COOT (Emsley et al., 2010) and refinement with PHENIX (Adams et al., 2010), yielding a final $R_{work}$ of 18.1% and $R_{free}$ of 22.4% (Table S2), with Ramachandran favored: 97.7% and Ramachandran outliers: 0.18%. The JUNV GP1 CR1-28/CR1-10 structure has $R_{work}$ 22.4% and $R_{free}$ of 28.1%, and the MACV GP1 CR1-07 structure has $R_{work}$ of 26.3% and $R_{free}$ of 27.8%. Figures were made with the PyMol Molecular Graphics System, Schrödinger, LLC.

Human Immunoglobulin Purification

Five (5) de-identified plasma samples from Argentine hemorrhagic fever survivors were obtained from the immune plasma bank at the Instituto Nacional de Enfermedades Virales Humanas (INEVH), based in Pergamino, Argentina, where these samples are routinely stored. Provision of the previously collected survivor plasma samples was approved by the INEVH Ethics Committee, and the Harvard University Faculty of Medicine Committee on Human Studies (identified as not involving human subjects under 45CFR46.102(f)). An additional 5 plasma survivor samples were obtained through INEVH under a Boston Children's Hospital Institutional Review Board and INEVH Ethics Committee approved protocol (IRB: IRB-P00007578) after informed consent was obtained from all subjects. Neutralizing antibody titers from the donors at the time of plasma collection had previously been determined by the fixed-virus/variable serum technique, with Vero cell monolayers infected with the XJC13 attenuated strain of JUNV virus, and defined as a plaque neutralization reduction of 80% ($PRNT_{80}$). Because the heparin that is contained in the plasma samples could interfere with the interpretation of the results of the pseudotype assay, IgG from these samples were purified using Protein G Ultralink® Resin (Thermo scientific), according to manufacturer's instructions.

ELISA Experiments Streptavidin-coated ELISA plates (Thermo scientific) were used. Wells were coated with biotinylated antigens at concentration of 0.2 µg/ml in PBS containing 2% bovine serum albumin. For ELISA-based competition assays, GD01 or 17b IgG were added at increasing concentrations during a pre-incubation step of 30 minutes, then the AHF survivor IgG was added at fixed concentrations (to obtain a baseline signal of 1.5-2 OD 450 nm). Bound antibody was detected with horse-radish peroxidase (HRP)-coupled anti-human antibody.

Single B Cell Sorting

Written informed consent was obtained from a healthy participant previously immunized with Candid #1 more than 2 years prior to study enrollment. This study was approved by the Boston Children's Hospital Institutional Review Board (IRB). Antigen-tetramers were prepared, and peripheral blood mononuclear cells were stained and washed as previously described (Franz et al., 2011), with the exception that phycoerythrein (PE)-labeled JUNV GP1 (Sort 1) and PE-labeled JUNV GP1 and PerCP-labeled JUNV GP1$_{mut}$ (Sort 2) were used for tetramer preparation and cell staining. The mRNA pre-amplification, RT-PCR, and nested PCR steps were carried out as previously described (Franz et al., 2011), with the exception that oligo-dT primers were used in the RT-PCR step.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following references are cited herein:

Abraham, J., Corbett, K. D., Farzan, M., Choe, H., and Harrison, S. C. (2010). Structural basis for receptor recognition by New World hemorrhagic fever arenaviruses. Nature structural & molecular biology 17, 438-444.

Abraham, J., Kwong, J. A., Albarifio, C. G., Lu, J. G., Radoshitzky, S. R., Salazar-Bravo, J., Farzan, M., Spiropoulou, C. F., and Choe, H. (2009). Host-species transferrin receptor 1 orthologs are cellular receptors for nonpathogenic new world clade B arenaviruses. PLoS pathogens 5, e1000358.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta crystallographica Section D, Biological crystallography 66, 213-221.

Aoki, S. T., Settembre, E. C., Trask, S. D., Greenberg, H. B., Harrison, S. C., and Dormitzer, P. R. (2009). Structure of rotavirus outer-layer protein VP7 bound with a neutralizing Fab. Science 324, 1444-1447.

Aricescu, A. R., Lu, W., and Jones, E. Y. (2006). A time- and cost-efficient system for high-level protein production in mammalian cells. Acta crystallographica Section D, Biological crystallography 62, 1243-1250.

Branco, L. M., Grove, J. N., Moses, L. M., Goba, A., Fullah, M., Momoh, M., Schoepp, R. J., Bausch, D. G., and Garry, R. F. (2010). Shedding of soluble glycoprotein 1 detected during acute Lassa virus infection in human subjects. Virology journal 7, 306.

Briese, T., Paweska, J. T., McMullan, L. K., Hutchison, S. K., Street, C., Palacios, G., Khristova, M. L., Weyer, J., Swanepoel, R., Egholm, M., et al. (2009). Genetic detection and characterization of Lujo virus, a new hemorrhagic fever-associated arenavirus from southern Africa. PLoS pathogens 5, e1000455.

Burri, D. J., da Palma, J. R., Kunz, S., and Pasquato, A. (2012). Envelope glycoprotein of arenaviruses. Viruses 4, 2162-2181.

Chandran, K., Sullivan, N.J., Felbor, U., Whelan, S. P., and Cunningham, J M (2005). Endosomal proteolysis of the Ebola virus glycoprotein is necessary for infection. Science 308, 1643-1645.

Charrel, R. N., and de Lamballerie, X. (2003). Arenaviruses other than Lassa virus. Antiviral research 57, 89-100.

Choe, H., Jemielity, S., Abraham, J., Radoshitzky, S. R., and Farzan, M. (2011). Transferrin receptor 1 in the zoonosis and pathogenesis of New World hemorrhagic fever arenaviruses. Current opinion in microbiology 14, 476-482.

Delgado, S., Erickson, B. R., Agudo, R., Blair, P. J., Vallejo, E., Albarifio, C. G., Vargas, J., Comer, J. A., Rollin, P. E., Ksiazek, T. G., et al. (2008). Chapare virus, a newly discovered arenavirus isolated from a fatal hemorrhagic fever case in Bolivia. PLoS pathogens 4, e1000047.

Demogines, A., Abraham, J., Choe, H., Farzan, M., and Sawyer, S. L. (2013). Dual host-virus arms races shape an essential housekeeping protein. PLoS biology 11, e1001571.

Dias, J. M., Kuehne, A. I., Abelson, D. M., Bale, S., Wong, A. C., Halfmann, P., Muhammad, M. A., Fusco, M. L., Zak, S. E., Kang, E., et al. (2011). A shared structural solution for neutralizing ebolaviruses. Nature structural & molecular biology 18, 1424-1427.

Emsley, P., Lohkamp, B., Scott, W. G., and Cowtan, K. (2010). Features and development of Coot. Acta crystallographica Section D, Biological crystallography 66, 486-501.

Enria, D. A., Briggiler, A. M., Fernandez, N.J., Levis, S. C., and Maiztegui, J. I. (1984). Importance of dose of neutralising antibodies in treatment of Argentine haemorrhagic fever with immune plasma. Lancet 2, 255-256.

Fields, C., O'Connell, D., Xiao, S., Lee, G. U., Billiald, P., and Muzard, J. (2013). Creation of recombinant antigen-binding molecules derived from hybridomas secreting specific antibodies. Nature protocols 8, 1125-1148.

Flyak, A. I., Ilinykh, P. A., Murin, C. D., Garron, T., Shen, X., Fusco, M. L., Hashiguchi, T., Bornholdt, Z. A., Slaughter, J. C., Sapparapu, G., et al. (2015). Mechanism of human antibody-mediated neutralization of Marburg virus. Cell 160, 893-903.

Franz, B., May, K. F. Jr., Dranoff G., Wucherpfennig K., et al. (2011). Ex vivo characterization and isolation of rare memory B cells with antigen tetramers. Blood 118, 348-357

Hashiguchi, T., Fusco, M. L., Bornholdt, Z. A., Lee, J. E., Flyak, A. I., Matsuoka, R., Kohda, D., Yanagi, Y., Hammel, M., Crowe, J. E., Jr., et al. (2015). Structural basis for Marburg virus neutralization by a cross-reactive human antibody. Cell 160, 904-912.

Helguera, G., Jemielity, S., Abraham, J., Cordo, S. M., Martinez, M. G., Rodriguez, J. A., Bregni, C., Wang, J. J., Farzan, M., Penichet, M. L., et al. (2012). An antibody recognizing the apical domain of human transferrin receptor 1 efficiently inhibits the entry of all New World hemorrhagic fever arenaviruses. Journal of virology 86, 4024-4028.

Lee, J. E., Fusco, M. L., Hessell, A. J., Oswald, W. B., Burton, D. R., and Saphire, E. O. (2008). Structure of the Ebola virus glycoprotein bound to an antibody from a human survivor. Nature 454, 177-182.

Leslie, A. G. W., and Powell, H. R. (2007). Evolving Methods for Macromolecular Crystallography, Vol 245 (Springer Netherlands).

Maiztegui, J. I., Fernandez, N.J., and de Damilano, A. J. (1979). Efficacy of immune plasma in treatment of Argentine haemorrhagic fever and association between treatment and a late neurological syndrome. Lancet 2, 1216-1217.

McCoy, A. J., Grosse-Kunstleve, R. W., Adams, P. D., Winn, M. D., Storoni, L. C., and Read, R. J. (2007). Phaser crystallographic software. Journal of applied crystallography 40, 658-674.

Murin, C. D., Fusco, M. L., Bornholdt, Z. A., Qiu, X., Olinger, G. G., Zeitlin, L., Kobinger, G. P., Ward, A. B., and Saphire, E. O. (2014). Structures of protective antibodies reveal sites of vulnerability on Ebola virus. Proceedings of the National Academy of Sciences of the United States of America 111, 17182-17187.

Oldstone, M. B. (2002). Arenaviruses. I. The epidemiology molecular and cell biology of arenaviruses. Introduction. Current topics in microbiology and immunology 262, V-XII.

Paessler, S., and Walker, D. H. (2013). Pathogenesis of the viral hemorrhagic fevers. Annual review of pathology 8, 411-440.

Radoshitzky, S. R., Abraham, J., Spiropoulou, C. F., Kuhn, J. H., Nguyen, D., Li, W., Nagel, J., Schmidt, P. J., Nunberg, J. H., Andrews, N.C., et al. (2007). Transferrin receptor 1 is a cellular receptor for New World haemorrhagic fever arenaviruses. Nature 446, 92-96.

Radoshitzky, S. R., Bao, Y., Buchmeier, M. J., Charrel, R. N., Clawson, A. N., Clegg, C. S., DeRisi, J. L., Emonet, S., Gonzalez, J. P., Kuhn, J. H., et al. (2015). Past, present, and future of arenavirus taxonomy. Archives of virology 160, 1851-1874.

Radoshitzky, S. R., Kuhn, J. H., Spiropoulou, C. F., Albarifto, C. G., Nguyen, D. P., Salazar-Bravo, J., Dorfman, T., Lee, A. S., Wang, E., Ross, S. R., et al. (2008). Receptor determinants of zoonotic transmission of New World hemorrhagic fever arenaviruses. Proceedings of the National Academy of Sciences of the United States of America 105, 2664-2669.

Ruggiero, H. A., Perez Isquierdo, F., Milani, H. A., Barri, A., Val, A., Maglio, F., Astarloa, L., Gonzalez Cambaceres, C., Milani, H. L., and Tallone, J. C. (1986). [Treatment of Argentine hemorrhagic fever with convalescent's plasma. 4433 cases]. Presse medicale 15, 2239-2242.

Salas, R., de Manzione, N., Tesh, R. B., Rico-Hesse, R., Shope, R. E., Betancourt, A., Godoy, O., Bruzual, R., Pacheco, M. E., Ramos, B., et al. (1991). Venezuelan haemorrhagic fever. Lancet 338, 1033-1036.

Sanchez, A., Pifat, D. Y., Kenyon, R. H., Peters, C. J., McCormick, J. B., and Kiley, M. P. (1989). Junin virus monoclonal antibodies: characterization and cross-reactivity with other arenaviruses. The Journal of general virology 70 (Pt 5), 1125-1132.

Scheid, J. F., Mouquet, H., Ueberheide, B., Diskin, R., Klein, F., Oliveira, T. Y., Pietzsch, J., Fenyo, D., Abadir, A., Velinzon, K., et al. (2011). Sequence and structural convergence of broad and potent HIV antibodies that mimic CD4 binding. Science 333, 1633-1637.

Schmidt, A. G., Therkelsen, M. D., Stewart, S., Kepler, T. B., Liao, H. X., Moody, M. A., Haynes, B. F., and Harrison, S. C. (2015). Viral receptor-binding site antibodies with diverse germline origins. Cell 161, 1026-1034.

Vela E. (2012). Animal models, prophylaxis, and therapeutics for arenavirus infections. Viruses, 4, 1802-1829.

Xu, R., Krause, J. C., McBride, R., Paulson, J. C., Crowe, J. E., Jr., and Wilson, I. A. (2013). A recurring motif for antibody recognition of the receptor-binding site of influenza hemagglutinin. Nature structural & molecular biology 20, 363-370.

Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. Science 329, 811-817.

What is claimed is:

1. An isolated antibody or an antigen-binding fragment thereof that specifically binds to arenavirus glycoprotein 1 (GP1), wherein the antibody or the antigen binding fragment thereof comprises a heavy chain comprising three complementary determining region (CDR) sequences as follows:

```
CDR H1 sequence
                                           (SEQ ID NO: 1)
GFTFGTSI CDR H2 sequence
                                           (SEQ ID NO: 2)
ISHDESRK CDR H3 sequence
                                           (SEQ ID NO: 3)
AKDLSPPYSYAWDIFQYW
``` and a light chain comprising three CDR sequences as follows:

```
CDR L1 sequence
                                           (SEQ ID NO: 4)
QSVLYSSRSDNKY CDR L2 sequence
                                          (SEQ ID NO: 36)
WAS CDR L3 sequence
                                           (SEQ ID NO: 5)
QQYYSSPPTF;
``` or wherein the antibody or the antigen binding fragment thereof comprises a heavy chain comprising three CDR sequences as follows:

```
CDR H1 sequence
                    (SEQ ID NO: 6)
GFTFSSA

CDR H2 sequence
                    (SEQ ID NO: 7)
IWSDGSNE

CDR H3 sequence
                    (SEQ ID NO: 8)
ATDKTYVSGYTSTWYYFNY
``` and a light chain comprising three CDR sequences as follows:

```
CDR L1 sequence
                    (SEQ ID NO: 9)
QSIDNW

CDR L2 sequence
                    (SEQ ID NO: 37)
KAS; and

CDR L3 sequence
                    (SEQ ID NO: 10)
QHRT.
```

2. The isolated antibody or antigen-binding fragment thereof of claim 1, wherein the antibody comprises the heavy chain sequence

```
                                              (SEQ ID NO: 11)
QVQLVESGGGVVQPGRSLRLSCAASGFTFSSSAMHWVRQAPGKGLE

WVAVIWSDGSNENYADSVKGRFTISRDNSKNTLYLQMSSLRAEDTAVYY

CATDKTYVSGYTSTWYYFNYWGQGTLVTVS
``` and the light chain sequence

```
                                              (SEQ ID NO: 12)
DIQMTQSPSTLSASVGDRVTITCRASQSIDNWLAWYQQKPGKAPKLLIY

TASRLESGVPSRFSGSGSGTEFTLTISSLQPDDFATYYCQHRTFGQG

TKVEIK
``` or an antibody comprises the heavy chain sequence

```
                                              (SEQ ID NO: 13)
QVQLVESGGGVVHPGRSLRLSCAASGFTFGTSIMHWVRQAPGKGM

QWVAQISHDESRKFYSDSVKGRFTVSRDNSKNTLFLEMSSLRIEDTA

VYYCAKDLSPPYSYAWDIFQYWGQGSLVTVS
``` and the light chain sequence

```
                                              (SEQ ID NO: 14)
DIVMTQSPESLAVSLGERATINCKSSQSVLYSSRSDNKDYLAWYQQK

PGQSPKLLIYWASTRESGVPERFTGSGSGTDFTLSISSLQAEDVAVY

YCQQYYSSPPTFGGGTKVELK.
```

3. The isolated antibody or antigen-binding fragment thereof of claim 1, that inhibits binding of GP1 and a transferrin receptor 1 (TfR1).

4. The isolated antibody or antigen-binding fragment thereof of claim 1, that binds a TfR1 receptor binding site of GP1.

5. The isolated antibody or antigen-binding fragment thereof of claim 1, wherein the TfR1 receptor binding site comprises amino acids 87-235 of JUNV GP1 as shown in FIG. 8A and set forth in SEQ ID NO: 30, or corresponding amino acids of an arenavirus GP1.

6. The isolated antibody or antigen-binding fragment thereof of claim 1, wherein the TfR1 receptor binding site comprises one or more of amino acids Serine 111, Aspartate 113, Isoleucine 115, and Lysine 216, amino acids 113-124 (JUNV GP1 loop 3), and amino acids 166-174 (JUNV GP1 loop 3) of JUNV GP1 as shown in FIG. 8A and set forth in SEQ ID NO: 30, or corresponding amino acids of an arenavirus GP1 7-13.

7. The isolated antibody or antigen-binding fragment thereof of claim 1, wherein the antibody or the antigen-binding fragment thereof binds to an arenavirus glycoprotein 1 (GP1) in a subject who is infected or at risk of infection with a New World arenavirus.

8. The isolated antibody or antigen-binding fragment thereof of claim 1, wherein the antibody or the antigen-binding fragment thereof binds to an arenavirus glycoprotein 1 (GP1) of a New World arenavirus selected from Junin (JUNV), Machupo (MACV), Guanarito (GTOV), Sabiá (SBAV), Chapare virus (CHPV), Tacaribe virus (TCRV), or White Water Arroyo virus (WWAV).

9. A method of inhibiting or preventing binding of a transferrin receptor 1 (TfR1) and an arenavirus glycoprotein 1 (GP1), the method comprising contacting a TfR1 with the isolated antibody or the antigen-binding fragment thereof of claim 1.

10. A method of treating or preventing a New World arenavirus infection, the method comprising administering to a subject in need thereof the isolated antibody or the antigen-binding fragment thereof of claim 1.

11. A kit comprising the antibody or antigen-binding fragment thereof of claim 1.

12. The method of claim 9, wherein the method is in vivo or in vitro.

13. The method of claim 9, wherein the antibody or the antigen-binding fragment thereof binds a TfR1 receptor binding site of GP1.

14. The method of claim 13, wherein the PRI receptor binding site comprises amino acids 87-235 of JUNV GP1 or corresponding amino acids of an arenavirus GP1.

15. The method of claim 13, wherein the TfR1 receptor binding site comprises one or more of amino acids Serine 111, Aspartate 113, Isoleucine 115, and Lysine 216, amino acids 113-124 (JUNV GP1 loop and amino acids 166-174 (JUNV GP1 loop 3) of JUNV GP1 or corresponding amino acids of an arenavirus GP1.

16. The method of claim 13, wherein the TfR1 receptor binding site interacts with Tyr211 of TfR1.

17. The method of claim 9, wherein the arenavirus GP1 is from a New World arenavirus selected from Junin (JUNV), Machupo (MACV), Guanarito (GTOV), Sabia (SBA Chapare virus (CHPV), Tacaribe virus (TCRV), or White Water Arroyo virus (WWAV).

18. The method of claim 10, wherein the subject has or is at risk of developing viral hemorrhagic fever.

19. The method of claim 10, wherein the isolated antibody or the antigen-binding fragment thereof has neutralizing activity against New World arenavirus in the subject.

* * * * *